US012667262B2

(12) United States Patent
　　Abreu

(10) Patent No.: US 12,667,262 B2
(45) Date of Patent: Jun. 30, 2026

(54) DEVICES, APPARATUSES AND SYSTEMS FOR MEASURING TEMPERATURE OF AN ABTT TERMINUS

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 0 days.

(21) Appl. No.: 18/820,998

(22) Filed: Aug. 30, 2024

(65) Prior Publication Data

US 2024/0415391 A1　　Dec. 19, 2024

Related U.S. Application Data

(62) Division of application No. 18/389,313, filed on Nov. 14, 2023, now Pat. No. 12,102,413, which is a division of application No. 15/066,779, filed on Mar. 10, 2016, now Pat. No. 11,872,018.

(60) Provisional application No. 62/131,131, filed on Mar. 10, 2015.

(51) Int. Cl.
　　*A61B 5/01*　　　　(2006.01)
　　*A61B 5/00*　　　　(2006.01)
　　*A61B 5/1172*　　　(2016.01)
　　*A61B 90/00*　　　(2016.01)

(52) U.S. Cl.
　　CPC .............. *A61B 5/01* (2013.01); *A61B 5/4064* (2013.01); *A61B 5/6898* (2013.01); *A61B 5/7425* (2013.01); *A61B 5/0008* (2013.01);

*A61B 5/1172* (2013.01); *A61B 2090/065* (2016.02); *A61B 2503/12* (2013.01);
(Continued)

(58) Field of Classification Search
CPC ....... A61B 5/01; A61B 5/4064; A61B 5/6898; A61B 5/7425; A61B 5/0008; A61B 5/1172; A61B 2503/12; A61B 2562/0247; A61B 2562/0271; A61B 2562/08; A61B 2090/065
See application file for complete search history.

(56) References Cited

U.S. PATENT DOCUMENTS

| | | | |
|---|---|---|---|
| 3,463,885 | A | 8/1969 | Upton |
| 3,531,642 | A | 9/1970 | Barnes et al. |
| 3,545,260 | A | 12/1970 | Lichtenstein et al. |
| | | (Continued) | |

FOREIGN PATENT DOCUMENTS

| | | |
|---|---|---|
| CN | 2398565 Y | 9/2000 |
| CN | 2446955 Y | 9/2001 |
| | (Continued) | |

OTHER PUBLICATIONS

International Preliminary Report on Patentability dated Sep. 21, 2017, issued in International Application No. PCT/US2016/021806; 7pp.

(Continued)

*Primary Examiner* — Chao Sheng
(74) *Attorney, Agent, or Firm* — Studebaker Brackett PLLC

(57) ABSTRACT

Apparatuses, systems, devices, mechanisms, and methods are used to locate an ABTT terminus and then to measure the temperature of the ABTT terminus.

19 Claims, 70 Drawing Sheets

(52) U.S. Cl.
CPC ................ *A61B 2562/0247* (2013.01); *A61B 2562/0271* (2013.01); *A61B 2562/08* (2013.01)

(56) References Cited

U.S. PATENT DOCUMENTS

| | | | |
|---|---|---|---|
| 3,585,849 A | 6/1971 | Grolman |
| 3,626,757 A | 12/1971 | Benzinger |
| 3,724,263 A | 4/1973 | Rose et al. |
| 3,769,961 A | 11/1973 | Fatt et al. |
| 3,897,272 A | 7/1975 | Medlar |
| 3,897,790 A | 8/1975 | Magilton et al. |
| 3,963,019 A | 6/1976 | Quandt |
| 4,186,184 A | 1/1980 | Zaffaroni |
| 4,231,052 A | 10/1980 | Day et al. |
| 4,297,685 A | 10/1981 | Brainard, II |
| 4,305,399 A | 12/1981 | Beale |
| 4,312,358 A | 1/1982 | Barney |
| 4,321,261 A | 3/1982 | Ellis et al. |
| 4,330,299 A | 5/1982 | Cerami |
| 4,331,161 A | 5/1982 | Patel |
| 4,344,315 A | 8/1982 | Moxon et al. |
| 4,344,438 A | 8/1982 | Schultz |
| 4,386,831 A | 6/1983 | Grounauer |
| 4,444,990 A | 4/1984 | Villar |
| 4,485,820 A | 12/1984 | Flower |
| 4,488,558 A | 12/1984 | Simbruner et al. |
| 4,595,020 A | 6/1986 | Palti |
| 4,597,392 A | 7/1986 | Opitz et al. |
| 4,628,938 A | 12/1986 | Lee |
| 4,629,424 A | 12/1986 | Lauks et al. |
| 4,771,792 A | 9/1988 | Seale |
| 4,784,149 A | 11/1988 | Berman et al. |
| 4,830,014 A | 5/1989 | Goodman et al. |
| 4,846,196 A | 7/1989 | Wiksell et al. |
| 4,860,755 A | 8/1989 | Erath |
| 4,922,913 A | 5/1990 | Waters, Jr. et al. |
| 4,944,303 A | 7/1990 | Katsuragi |
| 4,947,849 A | 8/1990 | Takahashi et al. |
| 4,951,671 A | 8/1990 | Coan |
| 4,979,831 A | 12/1990 | Schertz et al. |
| 5,005,577 A | 4/1991 | Frenkel |
| 5,046,482 A | 9/1991 | Everest |
| 5,062,432 A | 11/1991 | James et al. |
| 5,076,274 A | 12/1991 | Matsumoto |
| 5,109,852 A | 5/1992 | Kaye et al. |
| 5,115,815 A | 5/1992 | Hansen |
| 5,148,807 A | 9/1992 | Hsu |
| 5,165,409 A | 11/1992 | Coan |
| 5,179,953 A | 1/1993 | Kursar |
| 5,183,044 A | 2/1993 | Nishio et al. |
| 5,190,039 A | 3/1993 | Takeuchi et al. |
| 5,209,231 A | 5/1993 | Cote et al. |
| 5,217,015 A | 6/1993 | Kaye et al. |
| 5,222,495 A | 6/1993 | Clarke et al. |
| 5,222,809 A | 6/1993 | Ehrenkranz |
| 5,246,867 A | 9/1993 | Lakowicz et al. |
| 5,251,627 A | 10/1993 | Morris |
| 5,255,979 A | 10/1993 | Ferrari |
| 5,295,495 A | 3/1994 | Maddess |
| 5,297,554 A | 3/1994 | Glynn et al. |
| 5,341,805 A | 8/1994 | Stavridi et al. |
| 5,342,283 A | 8/1994 | Good |
| 5,342,789 A | 8/1994 | Chick et al. |
| 5,352,411 A | 10/1994 | Khuri |
| 5,356,780 A | 10/1994 | Robinson et al. |
| 5,375,595 A | 12/1994 | Sinha et al. |
| 5,383,452 A | 1/1995 | Buchert |
| 5,433,197 A | 7/1995 | Stark |
| 5,435,307 A | 7/1995 | Friauf et al. |
| 5,441,476 A | 8/1995 | Kitado et al. |
| 5,503,770 A | 4/1996 | James et al. |
| 5,522,662 A | 6/1996 | Shiokawa |
| 5,636,635 A | 6/1997 | Massie et al. |
| 5,653,239 A | 8/1997 | Pompei et al. |
| 5,664,578 A | 9/1997 | Boczan |
| 5,673,692 A | 10/1997 | Schulze et al. |
| 5,711,915 A | 1/1998 | Siegmund et al. |
| 5,796,341 A | 8/1998 | Stratiotis |
| 5,813,982 A | 9/1998 | Baratta |
| 5,817,008 A | 10/1998 | Rafert et al. |
| 5,820,557 A | 10/1998 | Hattori et al. |
| 5,830,139 A | 11/1998 | Abreu |
| 5,833,633 A | 11/1998 | Sarvazyan |
| 5,854,078 A | 12/1998 | Asher et al. |
| 5,860,934 A | 1/1999 | Sarvazyan |
| 5,862,803 A | 1/1999 | Besson et al. |
| 5,898,004 A | 4/1999 | Asher et al. |
| 5,984,880 A | 11/1999 | Lander et al. |
| 5,994,701 A | 11/1999 | Tsuchimoto et al. |
| 6,011,984 A | 1/2000 | Van Antwerp et al. |
| 6,028,323 A | 2/2000 | Liu |
| 6,040,194 A | 3/2000 | Chick et al. |
| 6,042,266 A | 3/2000 | Cheslock et al. |
| 6,047,203 A | 4/2000 | Sackner et al. |
| 6,072,180 A | 6/2000 | Kramer et al. |
| 6,120,460 A | 9/2000 | Abreu |
| 6,123,668 A | 9/2000 | Abreu |
| 6,126,595 A | 10/2000 | Amano et al. |
| 6,135,968 A | 10/2000 | Brounstein |
| 6,152,875 A | 11/2000 | Hakamata |
| 6,178,346 B1 | 1/2001 | Amundson et al. |
| 6,181,957 B1 | 1/2001 | Lambert et al. |
| 6,187,599 B1 | 2/2001 | Asher et al. |
| 6,196,714 B1 | 3/2001 | Bellifemine et al. |
| 6,197,534 B1 | 3/2001 | Lakowicz et al. |
| 6,197,928 B1 | 3/2001 | Tsien et al. |
| 6,203,193 B1 | 3/2001 | Egawa |
| 6,213,943 B1 | 4/2001 | Abreu |
| 6,256,522 B1 | 7/2001 | Schultz |
| 6,290,658 B1 | 9/2001 | Kolich |
| 6,292,685 B1 | 9/2001 | Pompei |
| 6,300,871 B1 | 10/2001 | Irwin et al. |
| 6,312,393 B1 | 11/2001 | Abreu |
| 6,319,540 B1 | 11/2001 | Van Antwerp et al. |
| 6,385,473 B1 | 5/2002 | Haines et al. |
| 6,385,474 B1 | 5/2002 | Rather et al. |
| 6,423,001 B1 | 7/2002 | Abreu |
| 6,432,050 B1 | 8/2002 | Porat et al. |
| 6,470,893 B1 | 10/2002 | Boesen |
| 6,529,617 B1 | 3/2003 | Prokoski |
| 6,536,945 B2 | 3/2003 | Rolston |
| 6,542,081 B2 | 4/2003 | Torch |
| 6,543,933 B2 | 4/2003 | Stergiopoulos et al. |
| 6,544,193 B2 | 4/2003 | Abreu |
| 6,681,127 B2 | 1/2004 | March |
| 6,731,976 B2 | 5/2004 | Penn et al. |
| 6,789,901 B1 | 9/2004 | Kormos |
| 6,791,087 B1 | 9/2004 | Okumura |
| 6,846,106 B1 | 1/2005 | Chen et al. |
| 7,187,960 B2 | 3/2007 | Abreu |
| 7,340,293 B2 | 3/2008 | McQuilkin |
| 7,346,386 B2 | 3/2008 | Pompei |
| 7,515,054 B2 | 4/2009 | Torch |
| 7,597,668 B2 | 10/2009 | Yarden |
| 7,621,877 B2 | 11/2009 | Schnall |
| 7,689,437 B1 | 3/2010 | Teller et al. |
| 7,706,673 B1 * | 4/2010 | Staudinger .......... G03B 17/561 396/428 |
| 7,756,559 B2 | 7/2010 | Abreu |
| 7,787,938 B2 | 8/2010 | Pompei |
| 7,837,623 B2 | 11/2010 | Aubry et al. |
| 8,103,071 B2 | 1/2012 | Schnell et al. |
| 8,172,242 B1 * | 5/2012 | Crandall .............. A61B 5/0059 378/197 |
| 8,172,459 B2 | 5/2012 | Abreu |
| 8,500,271 B2 | 8/2013 | Howell et al. |
| 8,527,022 B1 | 9/2013 | Lash et al. |
| 8,721,562 B2 | 5/2014 | Abreu |
| 8,834,020 B2 | 9/2014 | Abreu |
| 8,849,379 B2 | 9/2014 | Abreu |
| 9,355,612 B1 | 5/2016 | Shepard et al. |
| 2001/0028309 A1 | 10/2001 | Torch |
| 2002/0026119 A1 | 2/2002 | Pompei |
| 2002/0035340 A1 | 3/2002 | Fraden et al. |

(56)  References Cited

U.S. PATENT DOCUMENTS

| | | | |
|---|---|---|---|
| 2002/0049374 A1 | 4/2002 | Abreu | |
| 2002/0049389 A1 | 4/2002 | Abreu | |
| 2002/0068876 A1 | 6/2002 | Pompei et al. | |
| 2002/0111657 A1 | 8/2002 | Dae et al. | |
| 2002/0126731 A1 | 9/2002 | Stergiopoulos et al. | |
| 2003/0055473 A1 | 3/2003 | Ramsden et al. | |
| 2003/0060863 A1 | 3/2003 | Dobak | |
| 2003/0067958 A1 | 4/2003 | Jang | |
| 2003/0108223 A1 | 6/2003 | Prokoski | |
| 2003/0111605 A1 | 6/2003 | Sato et al. | |
| 2003/0179094 A1 | 9/2003 | Abreu | |
| 2003/0210146 A1 | 11/2003 | Tseng | |
| 2003/0212340 A1 | 11/2003 | Lussier et al. | |
| 2004/0028226 A1 | 2/2004 | Saar et al. | |
| 2004/0039298 A1 | 2/2004 | Abreu | |
| 2004/0059212 A1 | 3/2004 | Abreu | |
| 2004/0076316 A1 | 4/2004 | Fauci | |
| 2004/0082862 A1 | 4/2004 | Chance | |
| 2004/0125996 A1 | 7/2004 | Eddowes et al. | |
| 2004/0152991 A1 | 8/2004 | Pompei | |
| 2004/0154550 A1 | 8/2004 | McQuilkin | |
| 2004/0170216 A1 | 9/2004 | Russak et al. | |
| 2004/0210159 A1 | 10/2004 | Kibar | |
| 2004/0242976 A1* | 12/2004 | Abreu .................... A61B 5/746 | |
| | | | 600/315 |
| 2004/0246548 A1 | 12/2004 | Papuchon et al. | |
| 2005/0250996 A1 | 11/2005 | Shirai et al. | |
| 2006/0122473 A1 | 6/2006 | Kill et al. | |
| 2006/0215728 A1 | 9/2006 | Jang | |
| 2006/0264726 A1 | 11/2006 | Mannheimer et al. | |
| 2007/0055171 A1 | 3/2007 | Fraden | |
| 2007/0120879 A1 | 5/2007 | Kanade et al. | |
| 2007/0217659 A1* | 9/2007 | Harada ................... G06V 40/10 | |
| | | | 382/115 |
| 2007/0219434 A1 | 9/2007 | Abreu | |
| 2008/0043809 A1 | 2/2008 | Herbert | |
| 2008/0121442 A1 | 5/2008 | Boer et al. | |
| 2008/0200830 A1 | 8/2008 | Pompei | |
| 2008/0214949 A1 | 9/2008 | Stivoric et al. | |
| 2008/0219318 A1 | 9/2008 | Yue | |
| 2009/0105605 A1* | 4/2009 | Abreu ................... A61B 5/4076 | |
| | | | 600/549 |
| 2009/0157056 A1 | 6/2009 | Ferren et al. | |
| 2009/0309711 A1 | 12/2009 | Adappa et al. | |
| 2010/0022909 A1 | 1/2010 | Padiy | |
| 2010/0113894 A1 | 5/2010 | Padiy | |
| 2010/0204765 A1 | 8/2010 | Hall et al. | |
| 2011/0024626 A1 | 2/2011 | O'Donnell et al. | |
| 2011/0040161 A1 | 2/2011 | Abreu | |
| 2011/0077546 A1 | 3/2011 | Fabian | |
| 2011/0092822 A1 | 4/2011 | Pompei | |
| 2011/0282735 A1 | 11/2011 | Kordis et al. | |
| 2012/0031405 A1 | 2/2012 | Geist et al. | |
| 2012/0127127 A1 | 5/2012 | Large et al. | |
| 2012/0136285 A1 | 5/2012 | Korb et al. | |
| 2013/0014182 A1 | 1/2013 | Nussel et al. | |
| 2013/0124039 A1 | 5/2013 | Abreu | |
| 2013/0135198 A1 | 5/2013 | Hodge et al. | |
| 2013/0215928 A1 | 8/2013 | Bellifemine | |
| 2013/0292571 A1 | 11/2013 | Mukherjee et al. | |
| 2014/0267716 A1* | 9/2014 | Child .................... H04N 7/186 | |
| | | | 348/143 |
| 2016/0033319 A1* | 2/2016 | Kovacs ................ A61B 5/0205 | |
| | | | 177/25.13 |

FOREIGN PATENT DOCUMENTS

| | | | |
|---|---|---|---|
| CN | 1328432 A | 12/2001 | |
| DE | 4433104 C1 | 5/1996 | |
| EP | 0236028 A2 | 9/1987 | |
| EP | 0411121 A2 | 2/1991 | |
| EP | 2 120 681 B1 | 7/2011 | |
| EP | 1 951 110 B1 | 10/2012 | |
| JP | S61-48369 A | 3/1986 | |
| JP | H10-075934 A | 3/1998 | |
| JP | H10-239158 A | 9/1998 | |
| JP | H11-164826 A | 6/1999 | |
| JP | 2001500394 A | 1/2001 | |
| JP | 2001/031151 A | 2/2001 | |
| JP | 2002-525132 A | 8/2002 | |
| JP | 3885024 B2 | 2/2007 | |
| WO | 93/01745 A1 | 2/1993 | |
| WO | 97/19188 A1 | 5/1997 | |
| WO | 98/22820 A1 | 5/1998 | |
| WO | 99/51142 A2 | 10/1999 | |
| WO | 00/10007 A2 | 2/2000 | |
| WO | 00/13580 A1 | 3/2000 | |
| WO | 00/16051 A1 | 3/2000 | |
| WO | 00/16099 A1 | 3/2000 | |
| WO | 00/18237 A1 | 4/2000 | |
| WO | 00/64492 A1 | 11/2000 | |
| WO | 02/03855 A1 | 1/2002 | |
| WO | 02/28271 A2 | 4/2002 | |
| WO | 02/067688 A1 | 9/2002 | |
| WO | 2005/015163 A2 | 2/2005 | |
| WO | 2010-042738 A2 | 4/2010 | |

OTHER PUBLICATIONS

International Search Report and Written Opinion of the International Searching Authority dated Jul. 25, 2016, issued in International Application No. PCT/US2016/021806.

An Examiner's First Report; issued by the Australian Government, IP Australia dated Apr. 21, 2009, which corresponds to Australian Patent Application No. 2006306422.

An Examiner's Report No. 2; issued by the Australian Government, IP Australia dated Nov. 10, 2010, which corresponds to Australian Patent Application No. 2006306422.

English translation of an Office Action; issued by the Korean Intellectual Property Office dated Jun. 21, 2013, which corresponds to Korean Patent Application No. 10-2008-7012335.

English translation of an Office Action; issued by the Japanese Patent Office dated Nov. 17, 2011, which corresponds to Japanese Patent Application No. 2008-537828.

English translation of a Second Office Action; issued by the Japanese Patent Office dated Nov. 13, 2012, which corresponds to Japanese Patent Application No. 2008-537828.

English translation of a Third Office Action; issued by the Japanese Patent Office dated Nov. 26, 2013, which corresponds to Japanese Patent Application No. 2008-537828.

Overton, Staci. "Brain Temperature Tunnel Discovered." Medical Breakthroughs Reported by Ivanhoe, Jun. 2, 2003.

International Search Report; PCT/US2014/060199; dated Jan. 8, 2015.

International Search Report; PCT/US2014/060201; dated Mar. 3, 2015.

Dittmar, A. et al., A Non Invasive Wearable Sensor for the Measurement of Brain Temperature. Proceedings of the 28th IEEE EMBS Annual International Conference. Aug. 30-Sep. 3, 2006. pp. 900-902, New York City, USA.

An Office Action and Examination Search Report issued by the Canadian Intellectual Property Office dated Mar. 26, 2015, which corresponds to Canadian Patent Application No. 2,627,278.

International Search Report; PCTUS2015/010873; dated Apr. 10, 2015.

English translation of an Unfavorable Technical Opinion; issued by the National Institute of Industrial Property, which corresponds to Brazilian Patent Application BR122013001249-4.

RCA Technical Notes, Contact Lens Tonometer by Robert E. Morey, RCA TN No. 602, dated Dec. 1964, 2 pages.

Ophthal. Physiol. Opt., 1989, vol. 9, April, Research Note, Multiple Applications of the NCT: An Assessment of Instrument's Effect on IOP by G.E Russell and J.P.G. Bergmanson, pp. 212-214.

Arch Ophthalmol—vol. 97, Mar. 1979, The Pneumatonograph—A Laboratory Study, by Robert A. Moses, M.D. and Walter J. Grodzki Jr., D.D.S., pp. 547-552.

(56) References Cited

OTHER PUBLICATIONS

IEEE Transactions on bio-Medical Engineering, vol. BME-14, No. 2, Apr. 1967, Miniature Passive Pressure Transensor for Implanting in the Eye, by C.C. Collins, pp. 74-83.

Trans. Amer. Acad. of O. & O., Jan.-Feb. 1957, Tonometer Calibration, An Attempt to Remove Discrepancies Found in the 1954 Calibration Scale for Schiotz Tonometers by Jonas S. Friedenwald, M.D., pp. 108-123.

Investigative Ophthalmology, Feb. 1962, The Relationship Between Pressure and Volume Changes in Living and Dead Rabbit Eyes, by John E. Eisenlohr and Maurice E. Langham, pp. 63-77.

Investigative Ophthalmology, Sep. 1971, vol. 10, No. 9, Theory and Calibration of the Schiotz Tonometer VII. Experimental Results of Tonometric Measurements: Scale Reading Versus Indentation Volume by Robert A. Moses and Walter J. Grodzki, pp. 716-723.

The British Journal of Ophthalmology, Jun. 1920, Communications—Tonometry, by HJ. Schiotz, pp. 249-261.

American Journal of Opthalmology, vol. 20, No. 10, Oct. 1937, Contribution to the Theory and Practice of Tonometry by Jonas S. Friedenwald, M.D., pp. 985-1024.

Ophthalmologica vol. 150, No. 5, (1965), Rheology of the Human Sclera, Unifying Formulation of Ocular Rigidity, by W.K. McEwen and Roger St. Helen, pp. 321-346.

A.M.A. Archives of Ophthalmology, vol. 57, Apr. 1957, Tonometer Calibration, by Earle H. McBain, M.D., pp. 520-531.

The Photonics Dictionary, 1996 Book 4, 42nd Edition, pp. D-24, D153.

Manual of Skin Diseases, Fifth Edition, Gordon C. Sauer, MD., 1985, pp. 204, 373.

FM-2 Fluorotron™ Master Ocular Fluorophotometer, 1994 OcuMetrics, Inc.

Textbook of Biochemistry With Clinical Correlations, Second Edition, Thomas M. Devlin, Ph.D., 1986, pp. 118, 139.

Physical Optics, Third Revised Edition, Robert W. Wood, 1961, pp. 650-651.

An Examiner's First Report; issued by the Australian Government, IP Australia dated Dec. 18, 2008, which corresponds to Australian Patent Application No. 2004263812.

An Examiner's First Report; issued by the Australian Government, IP Australia dated Mar. 10, 2010, which corresponds to Australian Patent Application No. 2009212808.

An Examiner's First Report; issued by the Australian Government, IP Australia dated Feb. 19, 2010, which corresponds to Australian Patent Application No. 2009212861.

An Examiner's First Report; issued by the Australian Government, IP Australia dated Nov. 4, 2013, which corresponds to Australian Patent Application No. 2012247045.

An Office Action issued by the Canadian Intellectual Property Office dated May 3, 2012, which corresponds to Canadian Patent Application No. 2,517,869.

English translation of a First Office Action and Search Report; issued by the State Intellectual Property Office of the People's Republic of China dated Jul. 21, 2014, which corresponds to Chinese Patent Application No. 201310097177.3.

English translation of a First Office Action and Search Report; issued by the State Intellectual Property Office of the People's Republic of China dated Jul. 22, 2014, which corresponds to Chinese Patent Application No. 201310097142.X.

A supplementary European Search Report; issued by the European Patent Office dated Oct. 17, 2008, which corresponds to European Patent Application No. 04785841.0-1265.

A "Communication pursuant to Article 94(3) EPC," issued by the European Patent Office dated Jan. 27, 2009, which corresponds to European Patent Application No. 04785841.0-1265.

A "Communication pursuant to Article 94(3) EPC," issued by the European Patent Office dated Sep. 12, 2013, which corresponds to European Patent Application No. 04785841.0-1657.

English Translation of Relevant Portion of Office Action; issued by the State of Israel Department of Justice, Patent Office dated Jul. 3, 2013, which corresponds to Israeli Patent Application No. 1704896.

English translation of Notification of Reasons for Refusal; issued by the Japanese Patent Office dated Jun. 11, 2009, which corresponds to Japanese Patent Application No. 2006-508817.

English translation of Notification of Reasons for Refusal; issued by the Japanese Patent Office dated Jan. 12, 2010, which corresponds to Japanese Patent Application No. 2006-508817.

A Summarized English Translation of Office Action; issued by the Instituto Mexicano de la Propiedad Industrial dated Jul. 4, 2008, which corresponds to Mexican National Phase Patent Application No. PA/a/2005/009159.

An Office Action; issued by the Instituto Mexicano de la Propiedad Industrial dated Sep. 25, 2009, which corresponds to Mexican National Phase Patent Application No. PA/a/2005/009159.

International Search Report & Written Opinion; PCT/US2004/005496; dated May 6, 2005.

English translation of an Office Action; issued by the Japanese Patent Office dated Jan. 22, 2009, which corresponds to Japanese Patent Application No. 2004-515642.

English translation of an Office Action; issued by the National Institute of Industrial Property dated Jul. 1, 2013, which corresponds to Brazilian Patent Application PI0309578-9.

English translation of an Office Action; issued by the National Institute of Industrial Property, which corresponds to Brazilian Patent Application PI0309578-9.

English translation of the "First Office Action," and "Search Report," issued by the State Intellectual Property Office of the People's Republic of China dated Jun. 4, 2014, which corresponds to Chinese Application No. 201210361917.5.

A "Communication pursuant to Article 94(3) EPC," issued by the European Patent Office dated Jan. 27, 2009, which corresponds to European Patent Application No. 03 754 363.4-1265.

A second "Communication pursuant to Article 94(3) EPC," issued by the European Patent Office dated Sep. 13, 2013, which corresponds to European Patent Application No. 03 754 363.4-1657.

A third "Communication pursuant to Article 94(3) EPC," issued by the European Patent Office dated Mar. 4, 2014, which corresponds to European Patent Application No. 03 754 363.4-1657.

A fourth "Communication pursuant to Article 94(3) EPC," issued by the European Patent Office dated Sep. 24, 2014, which corresponds to European Patent Application No. 03 754 363.4-1657.

English translation of an Office Action; issued by the State of Israel Department of Justice, Patent Office dated Nov. 26, 2008, which corresponds to Israeli Patent Application No. 164685.

English translation of an Office Action; issued by the Korean Intellectual Property Office dated Dec. 26, 2011, which corresponds to Korean Patent Application No. 10-2010-7018173.

International Search Report; PCT/US03/12382; dated May 13, 2005.

International Search Report; PCT/US2006/041238; dated Aug. 31, 2007.

An Office Action issued by the Canadian Intellectual Property Office dated Aug. 2, 2011, which corresponds to Canadian Patent Application No. 2,627,278.

A Second Office Action issued by the Canadian Intellectual Property Office dated Mar. 14, 2012, which corresponds to Canadian Patent Application No. 2,627,278.

A "Communication pursuant to Particle 94(3) EPC," issued by the European Patent Office dated May 13, 2011, which corresponds to European Patent Application No. 06 826 452.2-2319.

English translation of an Office Action; issued by the State of Israel Department of Justice, Patent Office dated Jun. 23, 2011, which corresponds to Israeli Patent Application No. 191039.

An Examiner's First Report; issued by the Australian Government, IP Australia dated Jan. 13, 2012, which corresponds to Australian Patent Application No. 2011202015.

Patent Examination Report No. 1; issued by the Australian Government, IP Australia dated Dec. 13, 2013, which corresponds to Australian Patent Application No. 2012203667.

* cited by examiner

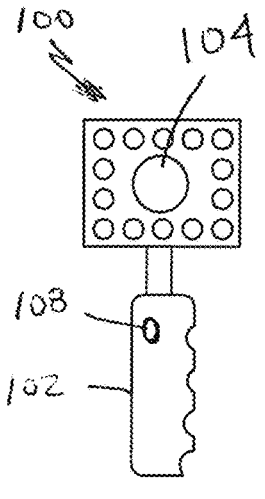
FIG. 6
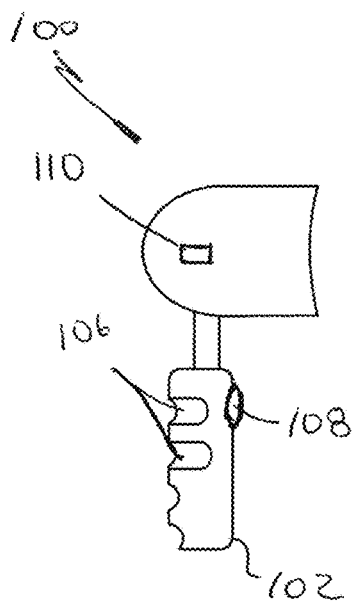
FIG. 7

FIG. 7A
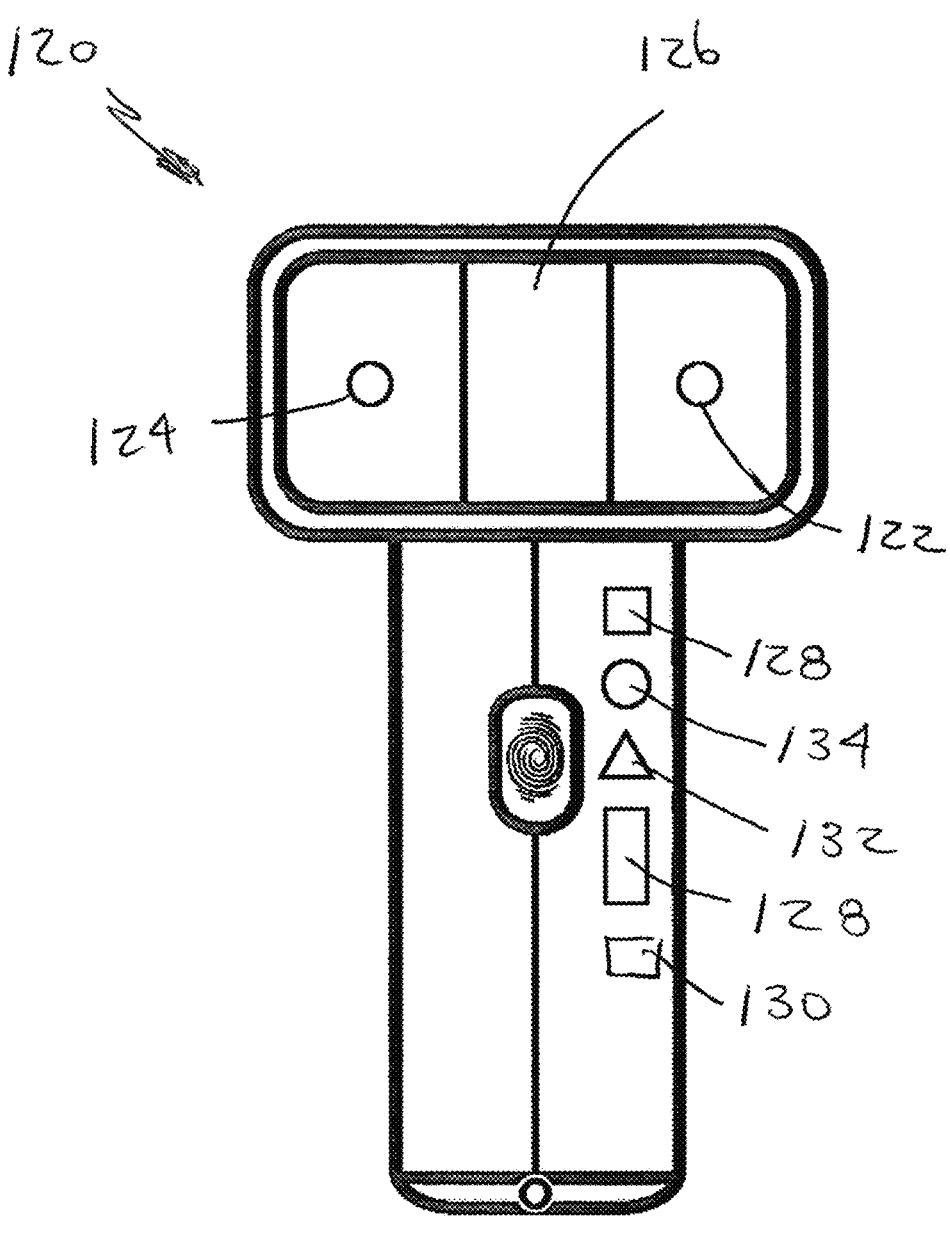

FIG. 7B
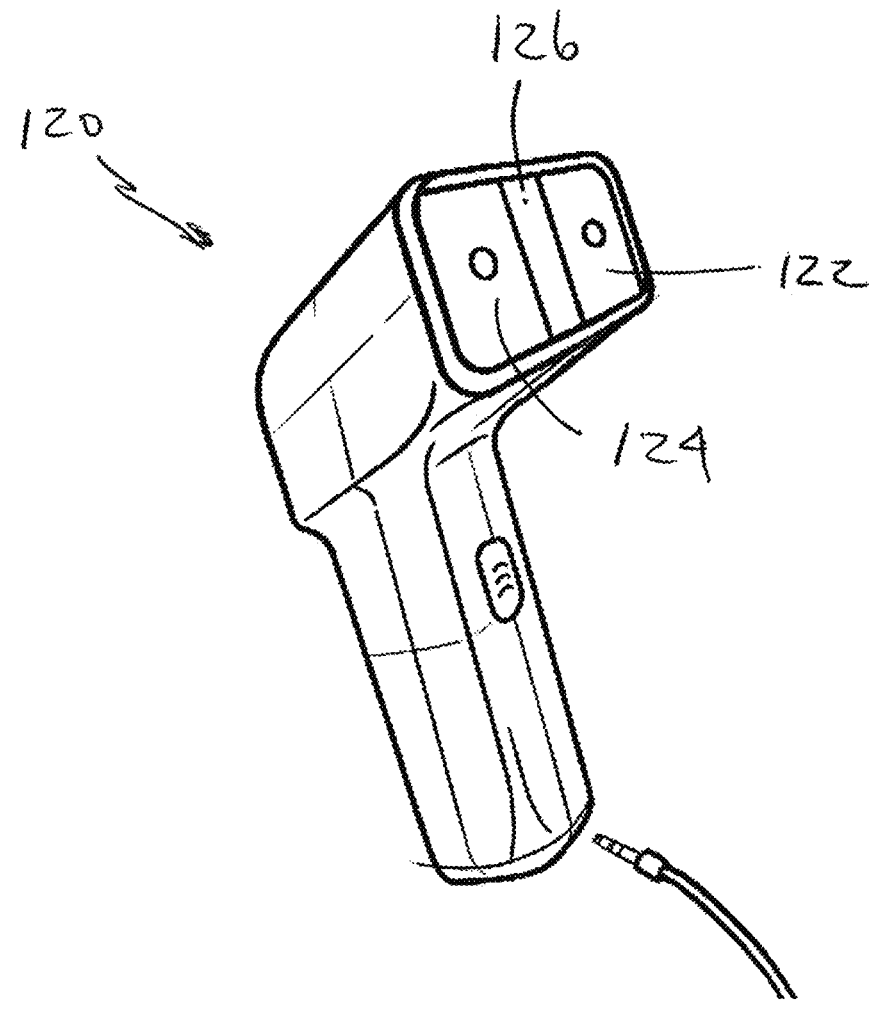

FIG. 7C
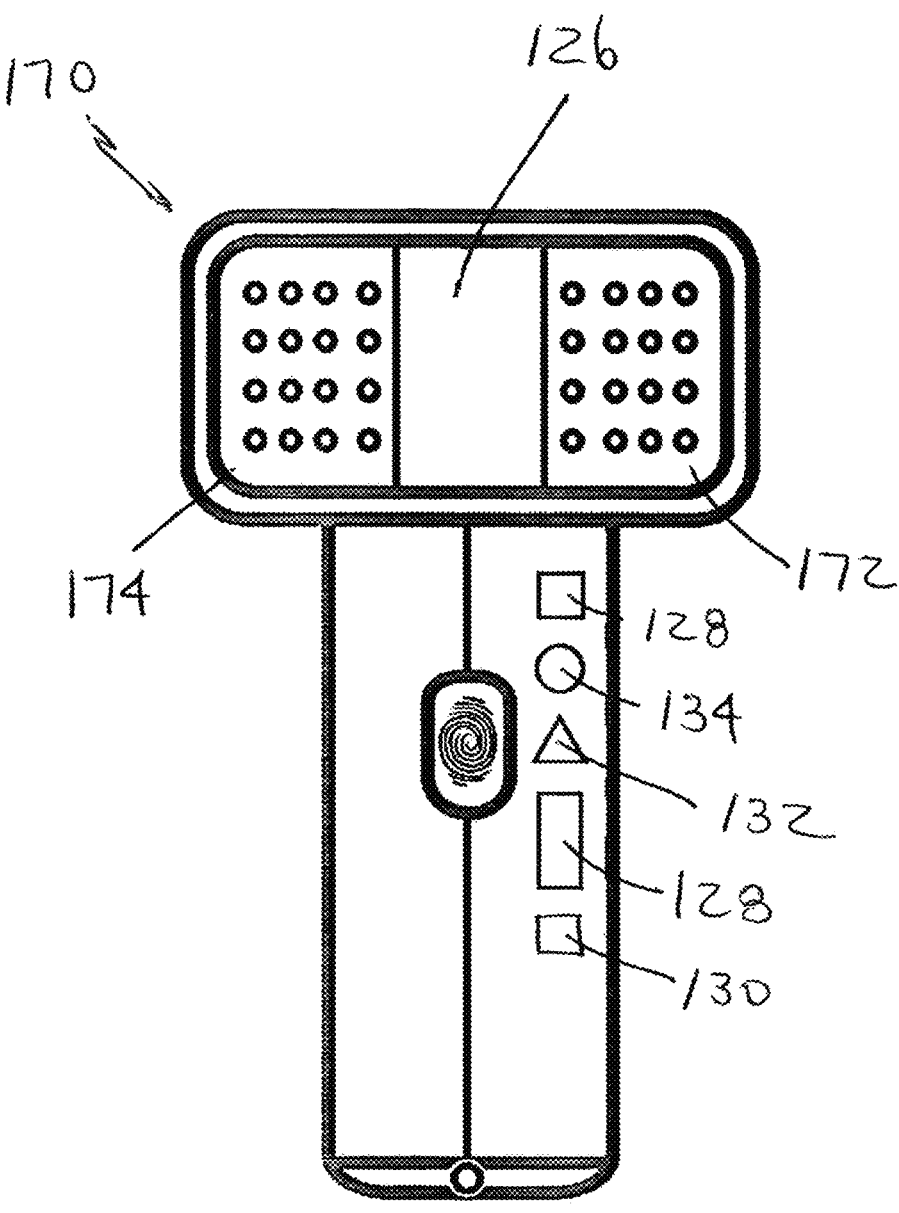

FIG. 7F
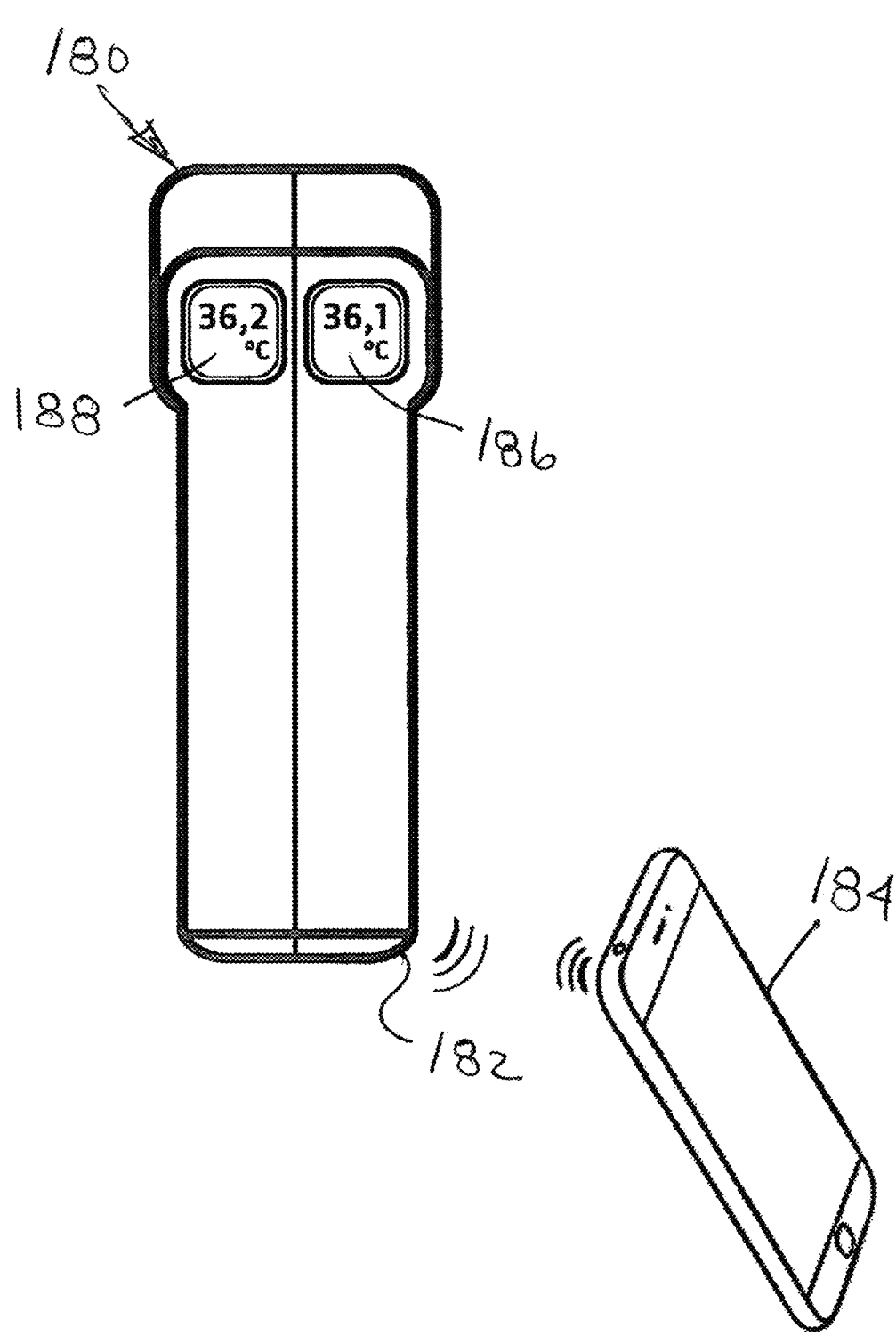

FIG. 7G
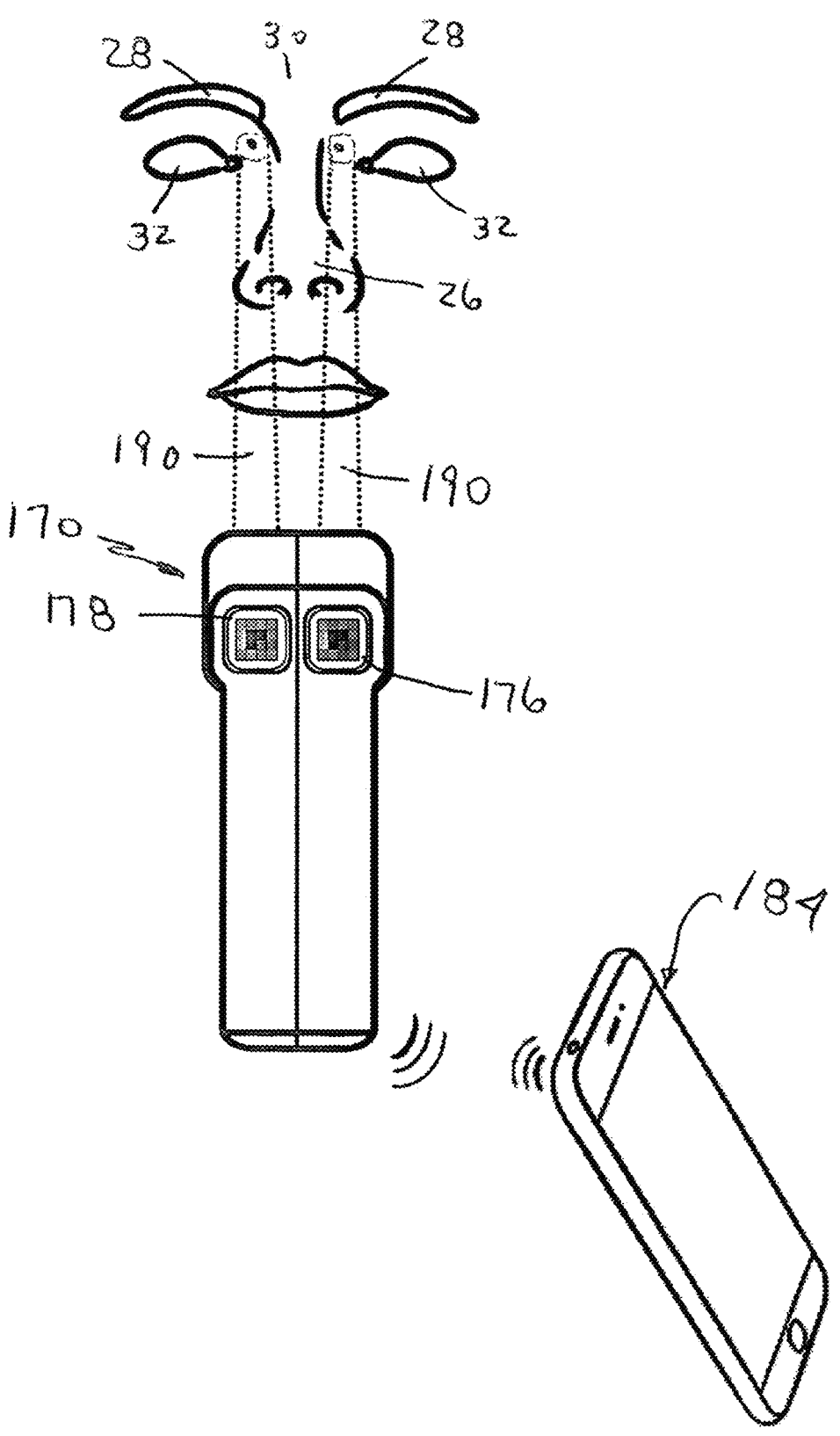

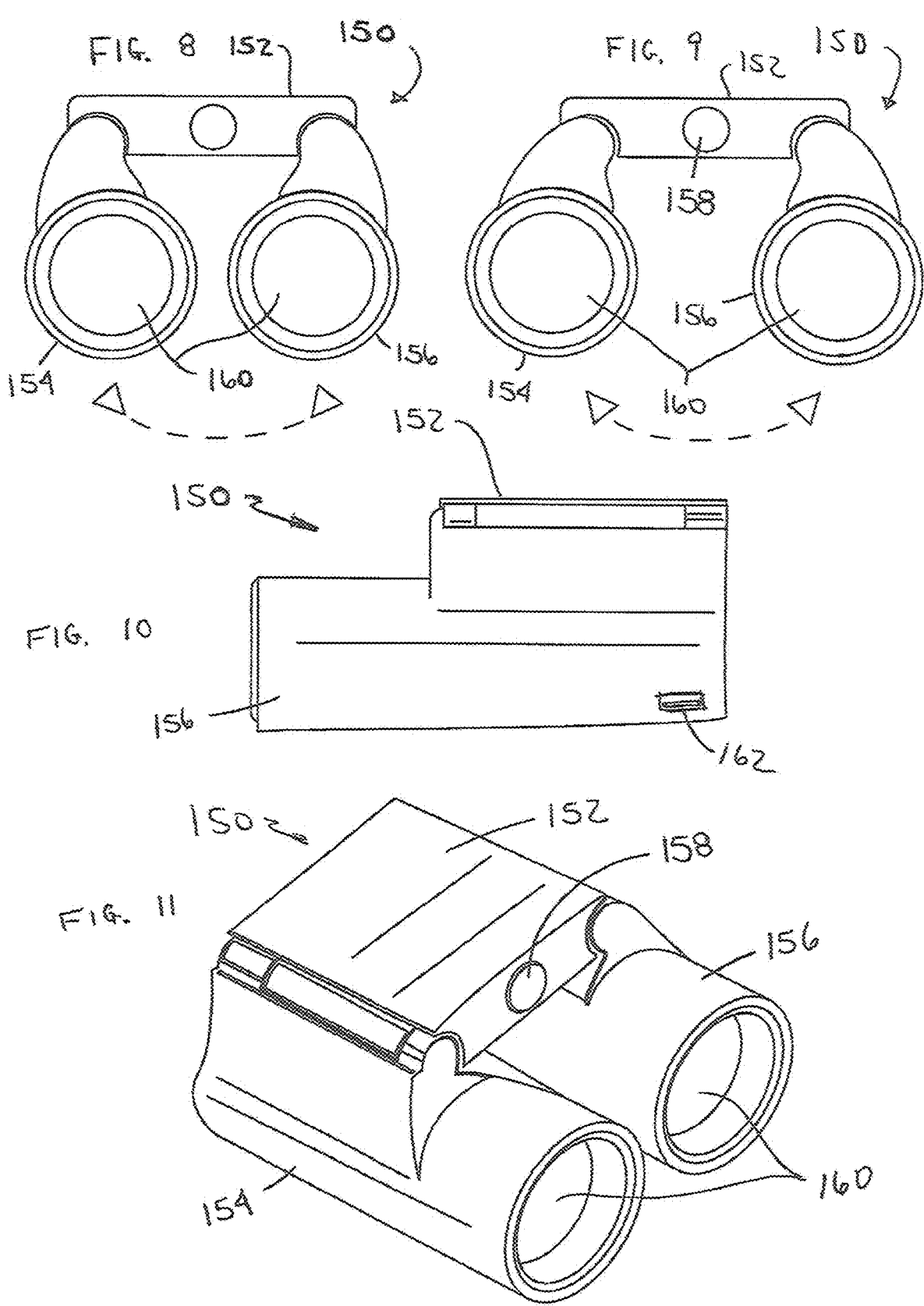

FIG. 8A
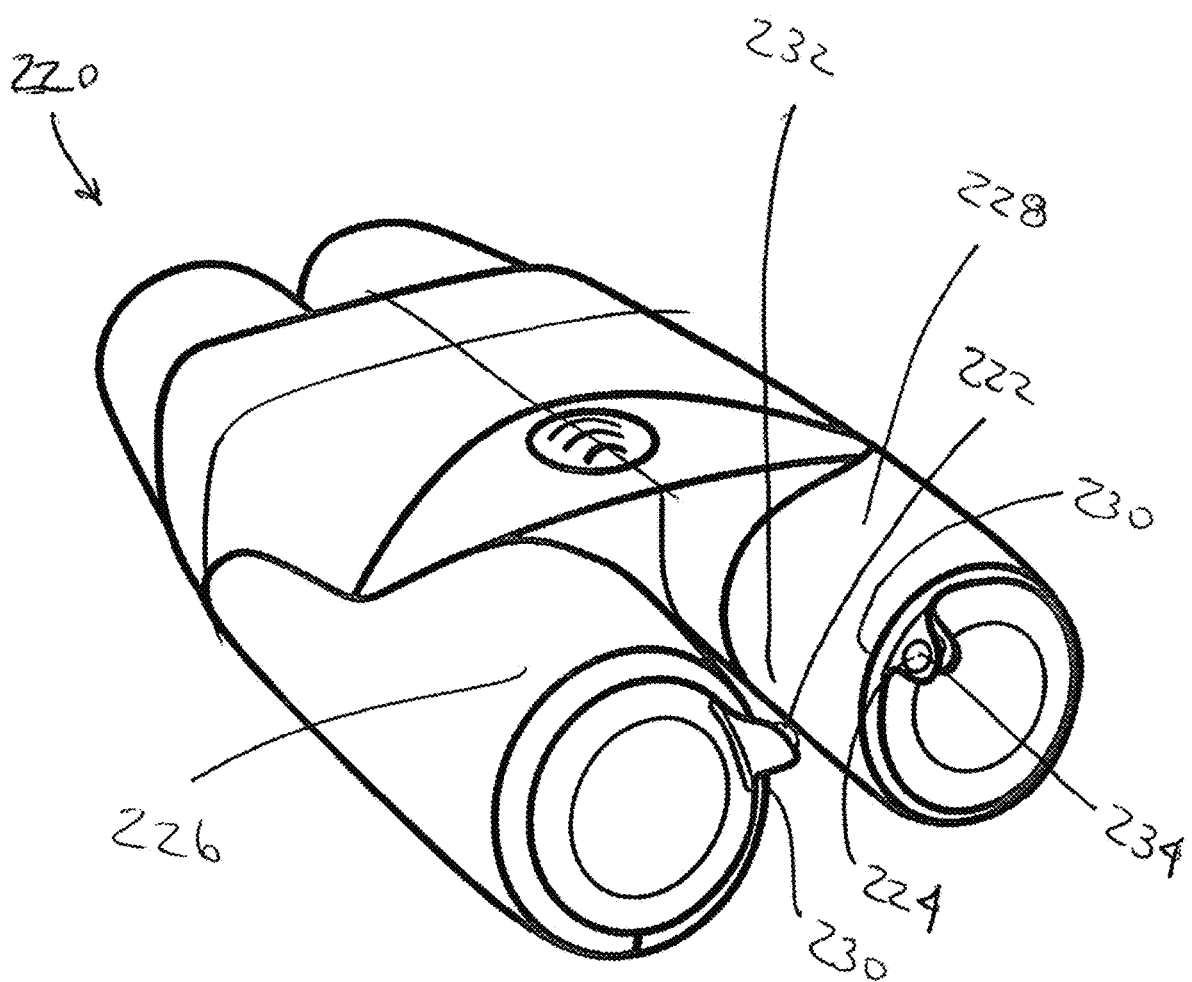

FIG. 8B
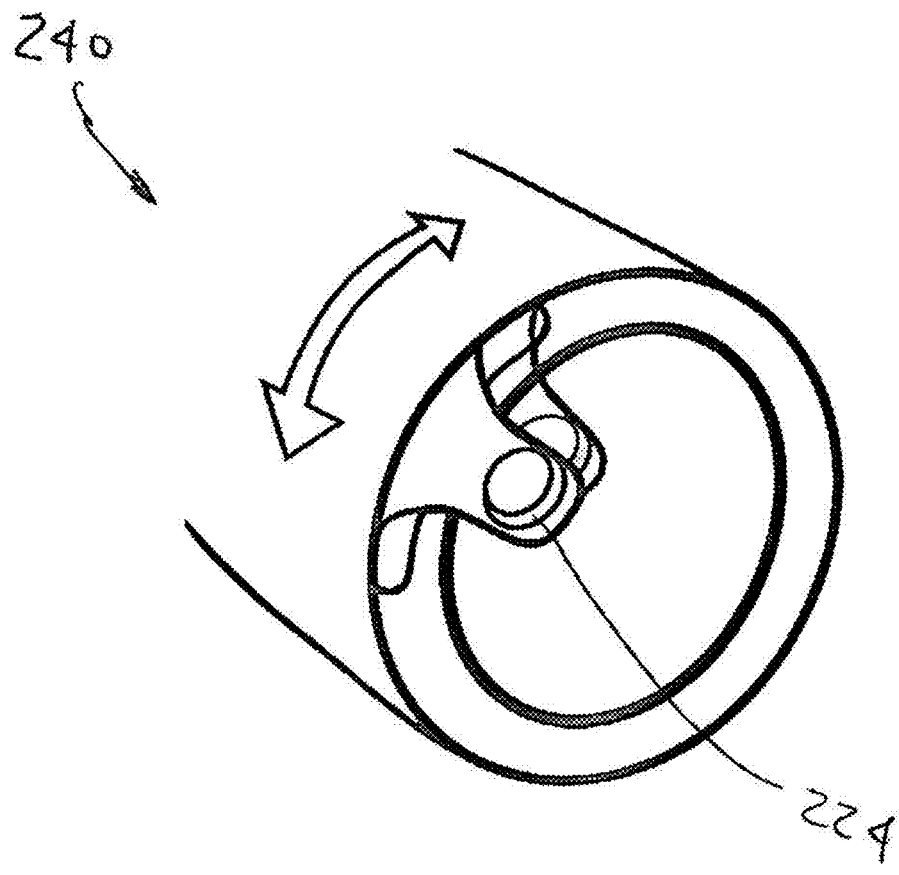

250

250

FIG. 30A
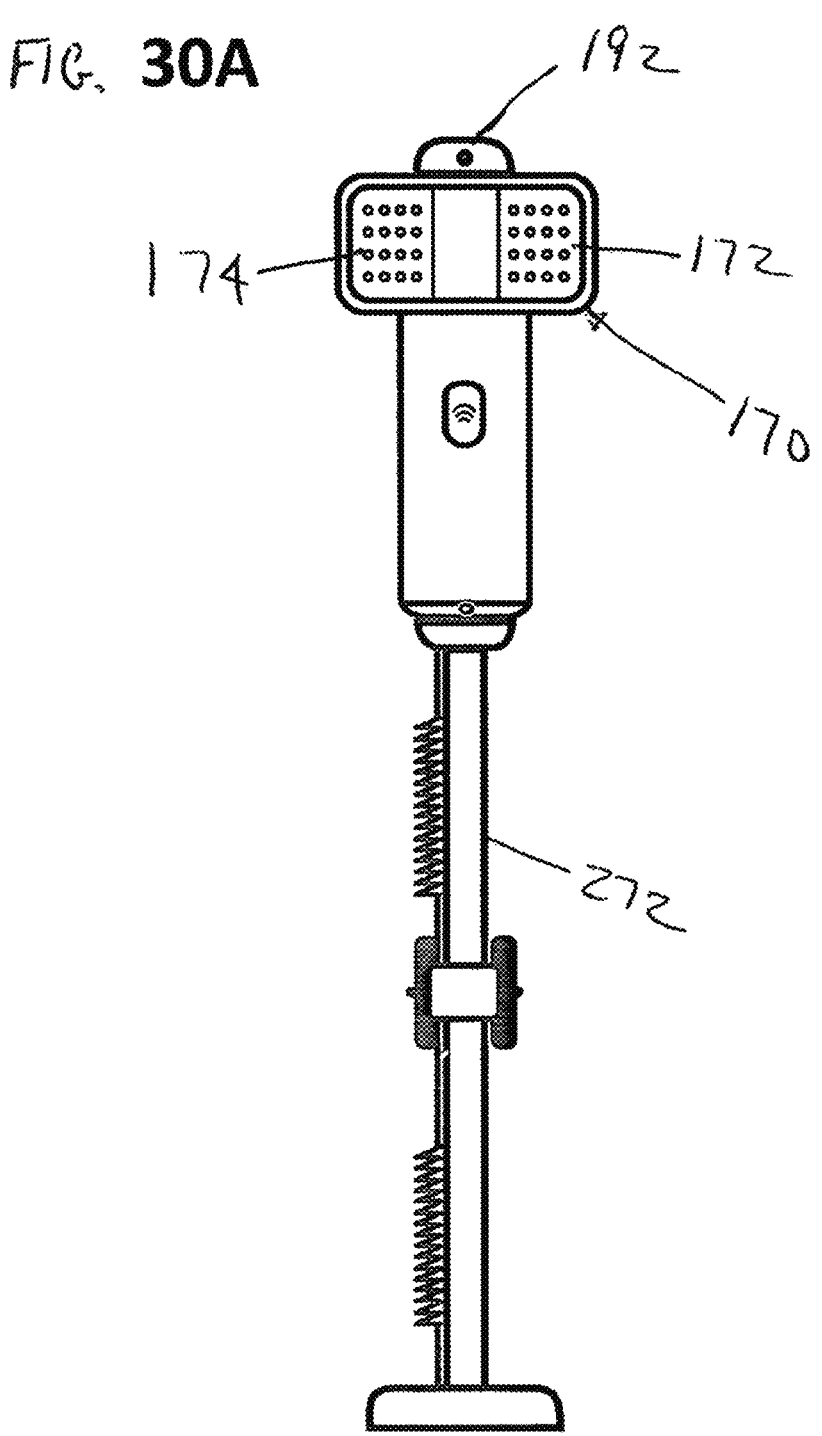

FIG. 30C
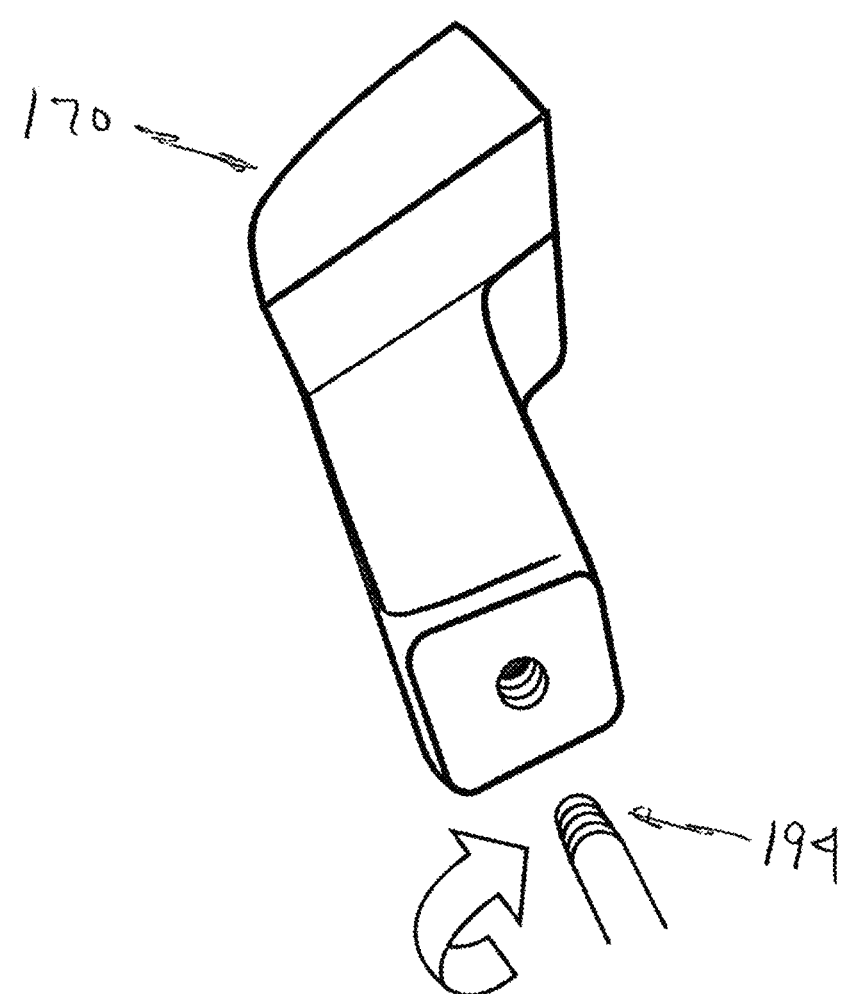

*FIG.* 33B
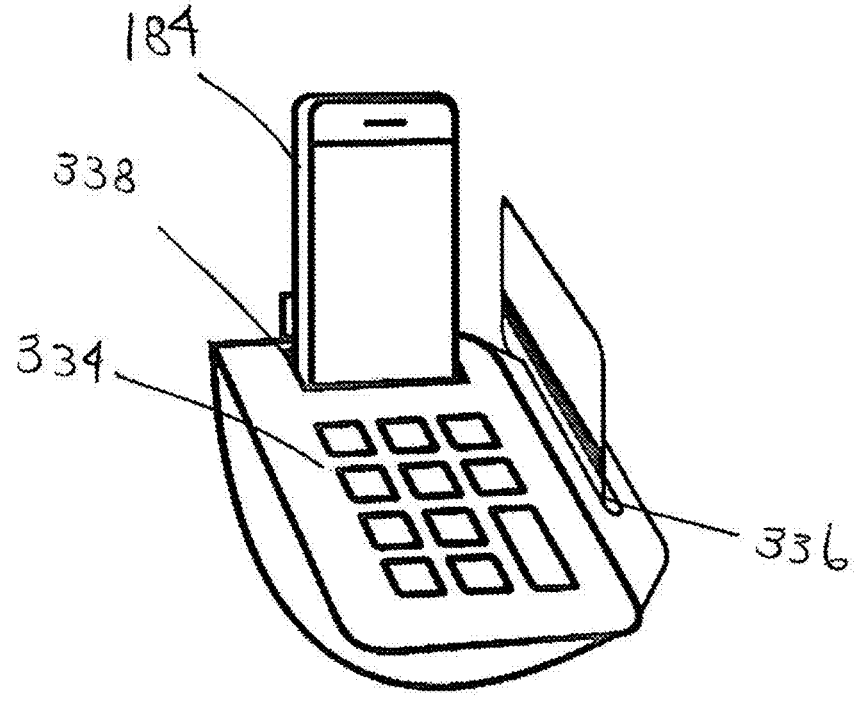

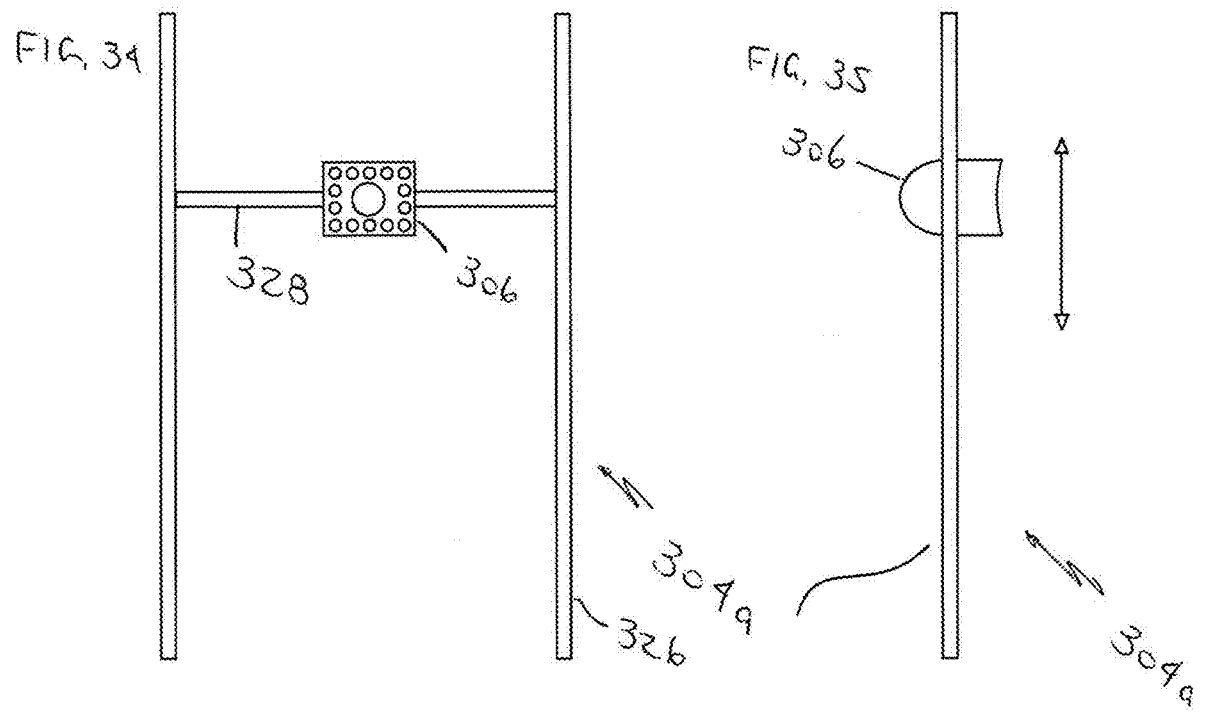
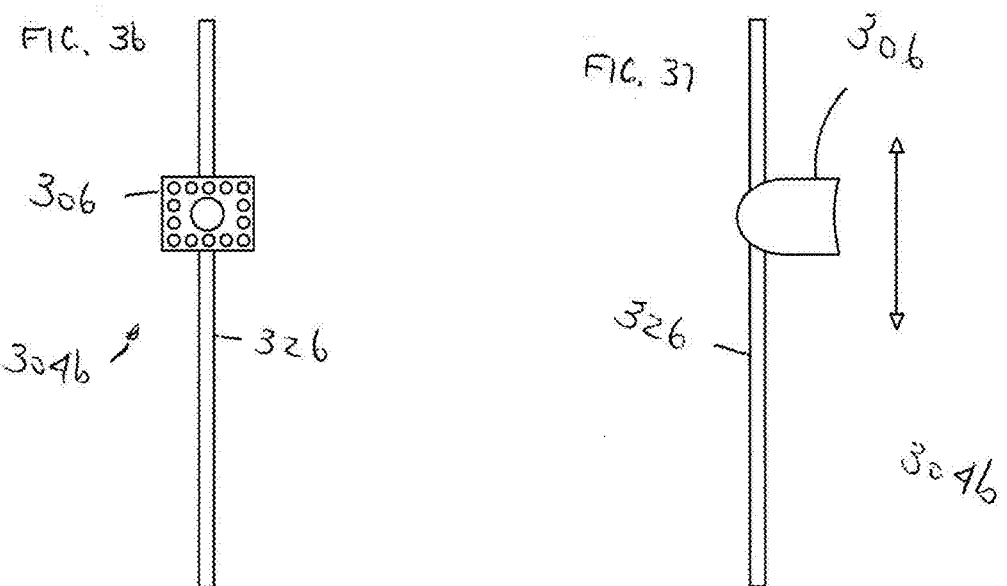

FIG. 40
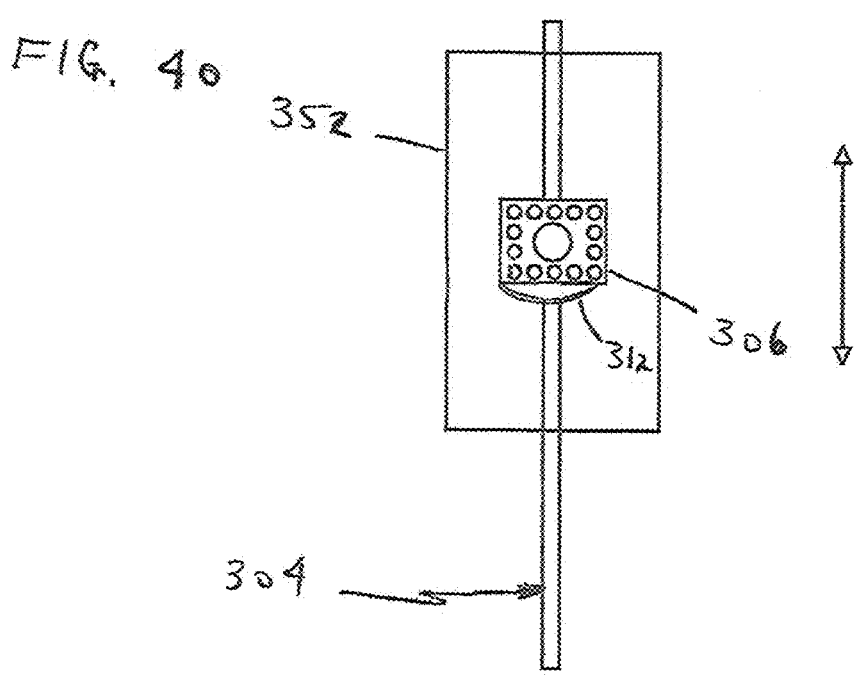
FIG. 41
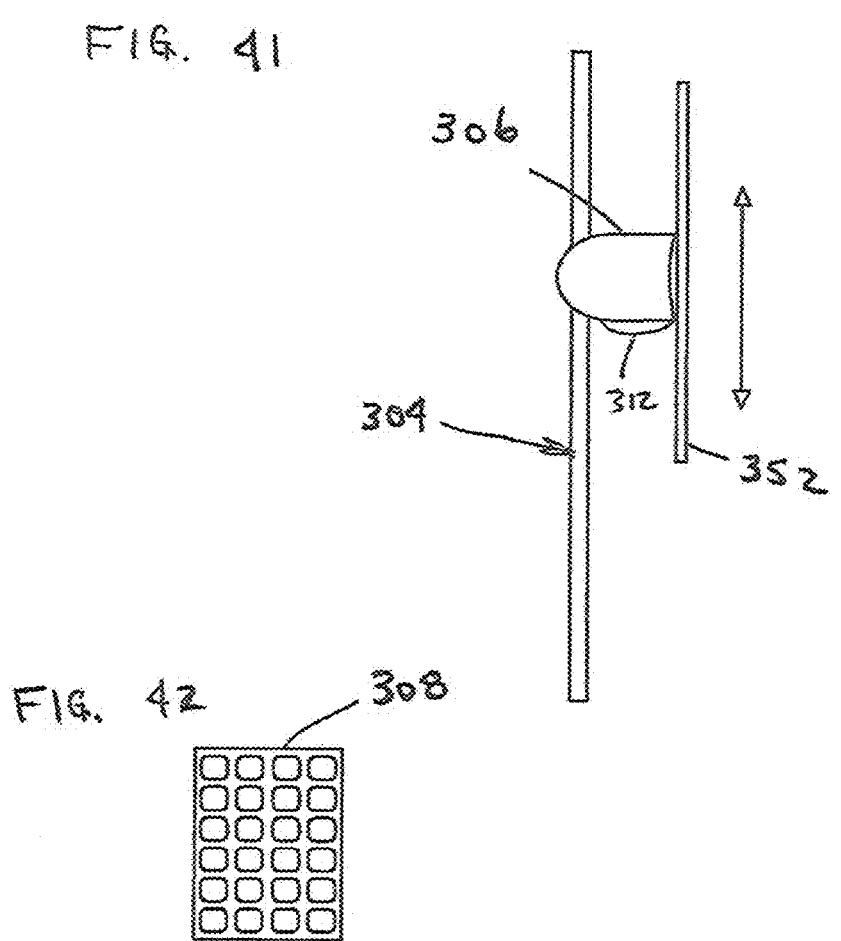
FIG. 42

FIG. 46
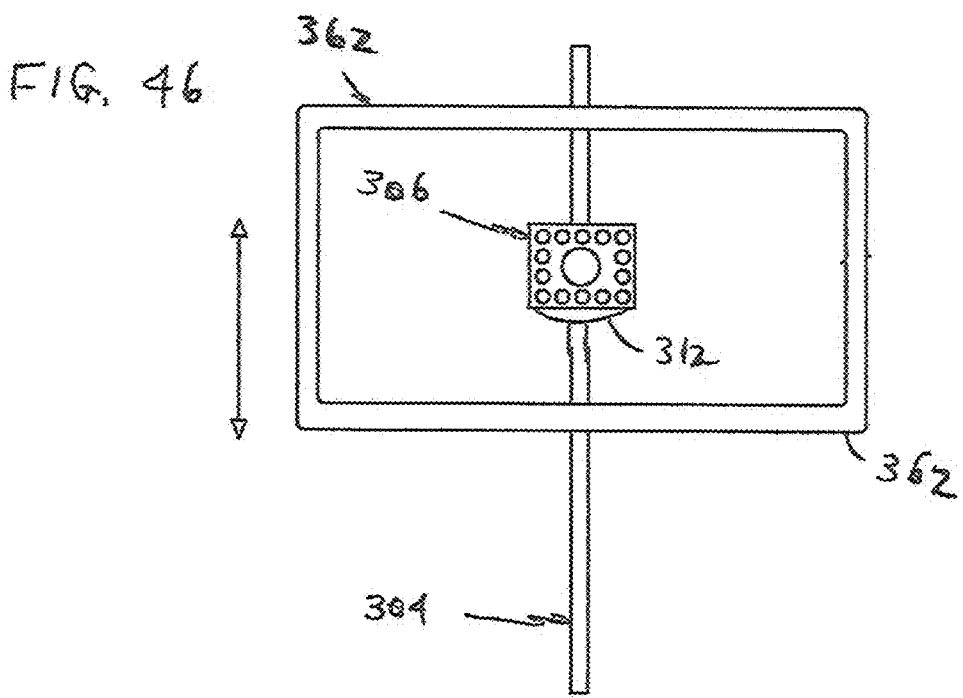
FIG. 47
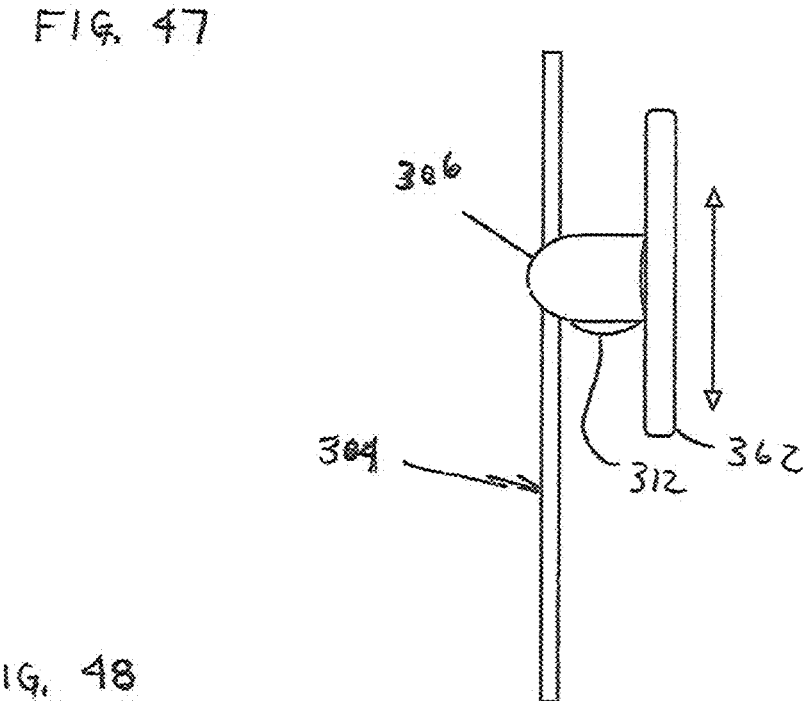
FIG. 48

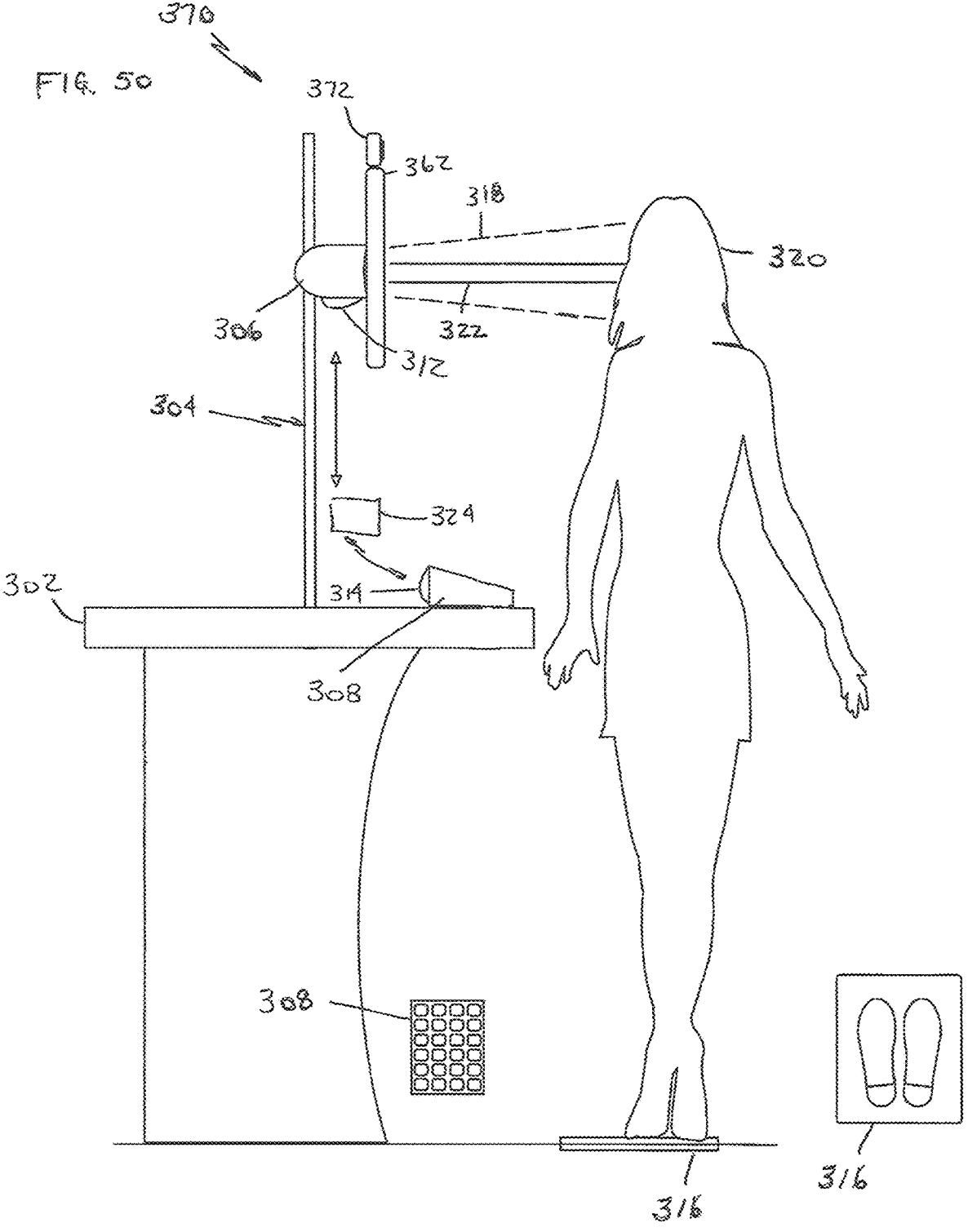

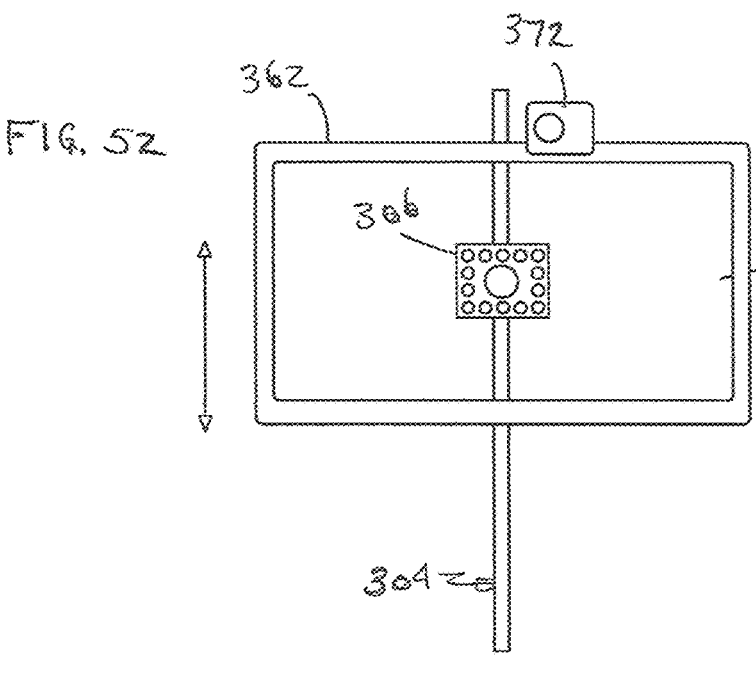
FIG. 52
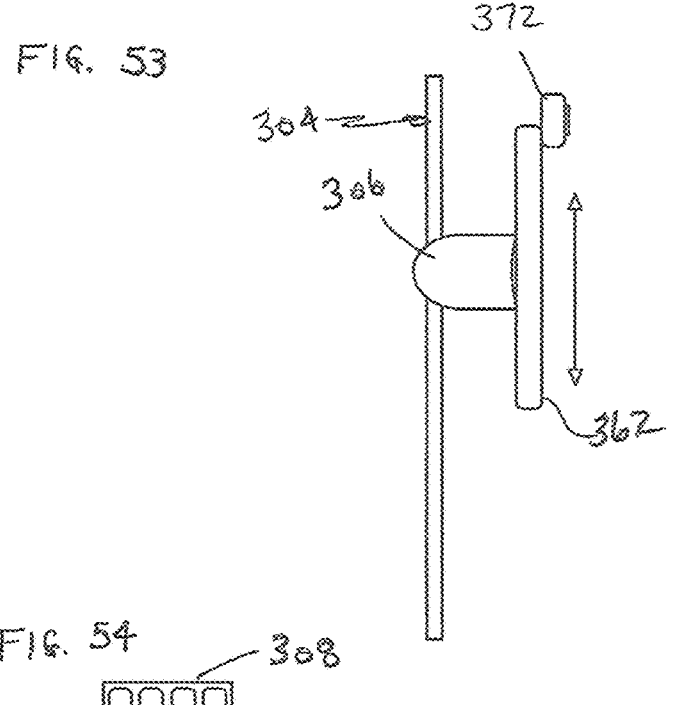
FIG. 53
FIG. 54
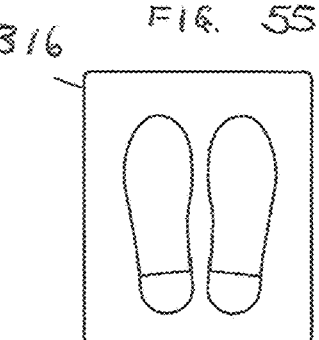
FIG. 55

FIG. 59
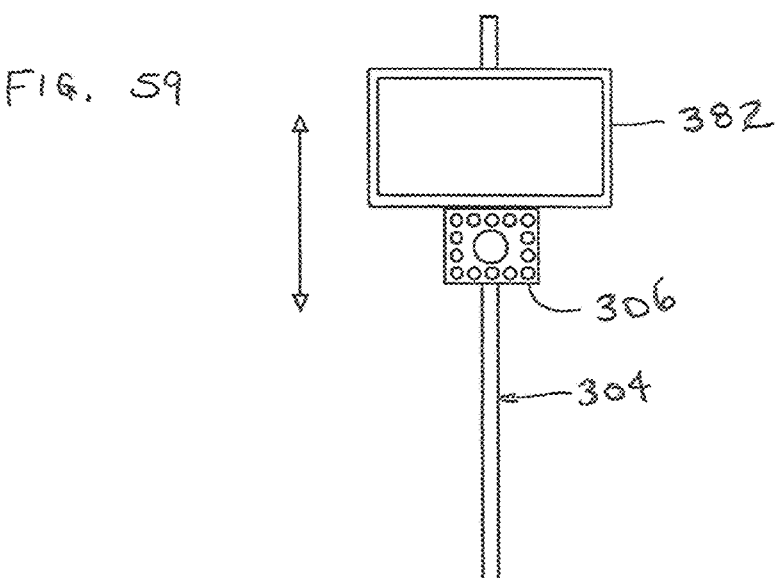
382
306
304
FIG. 60
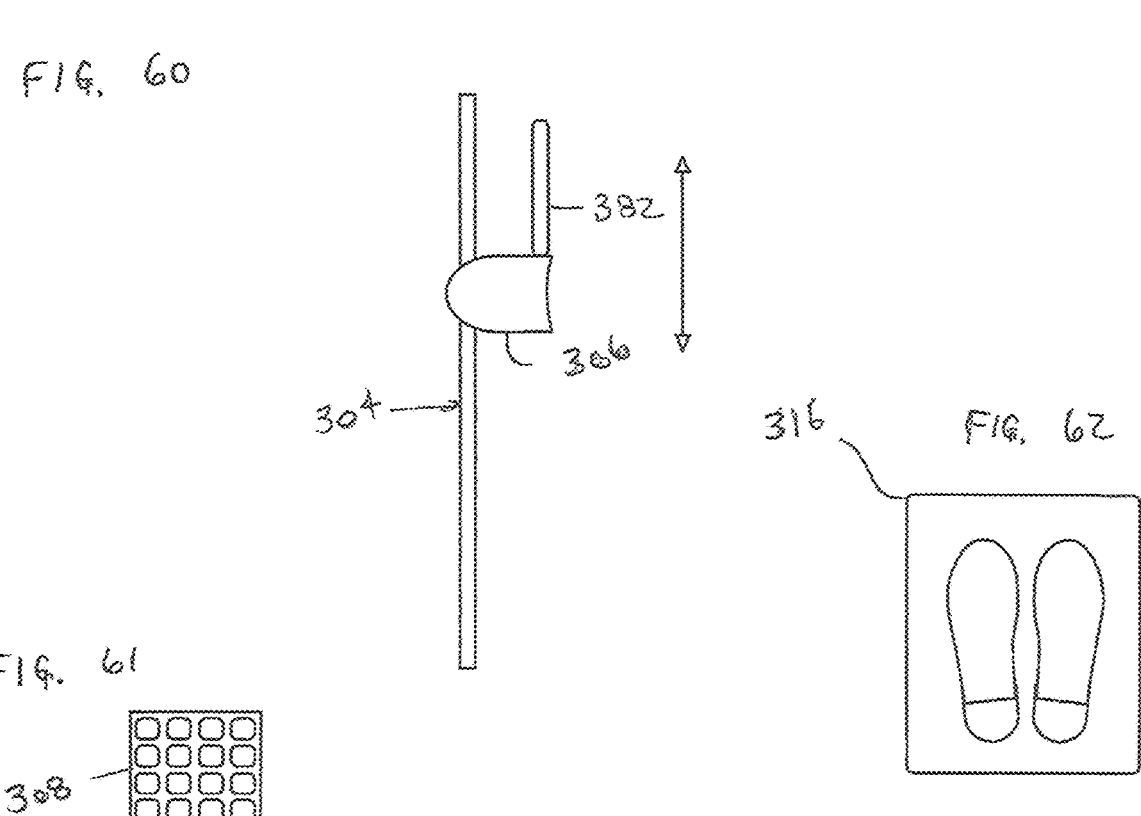
382
306
304
316
FIG. 62
FIG. 61
308

FIG. 66
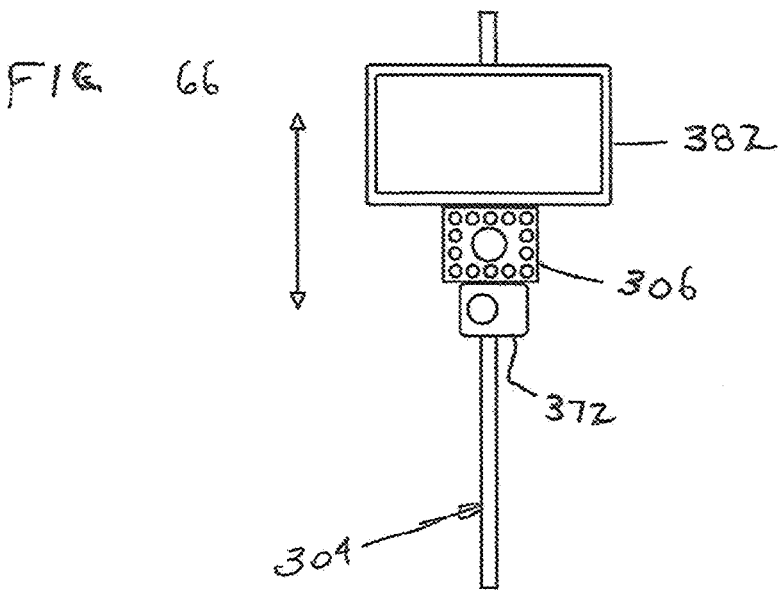
382
306
372
304
FIG. 67
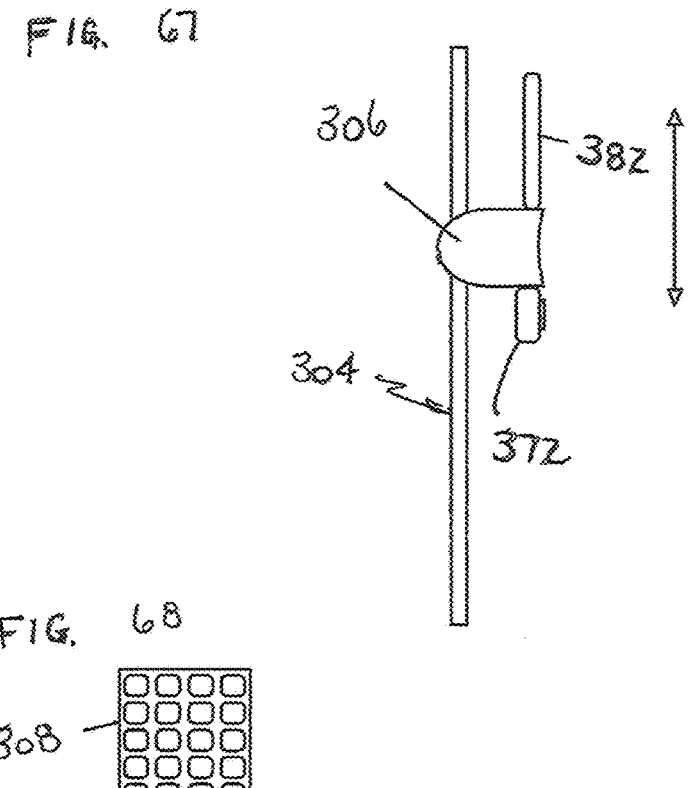
306
382
304
372
FIG. 68
308
FIG. 69
316
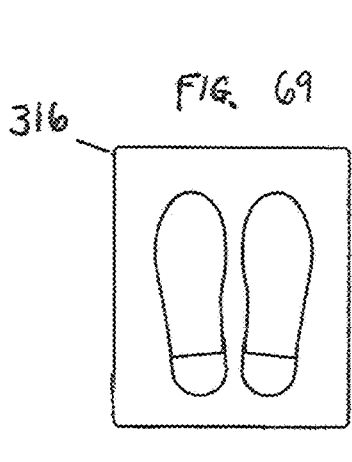

FIG. 70A
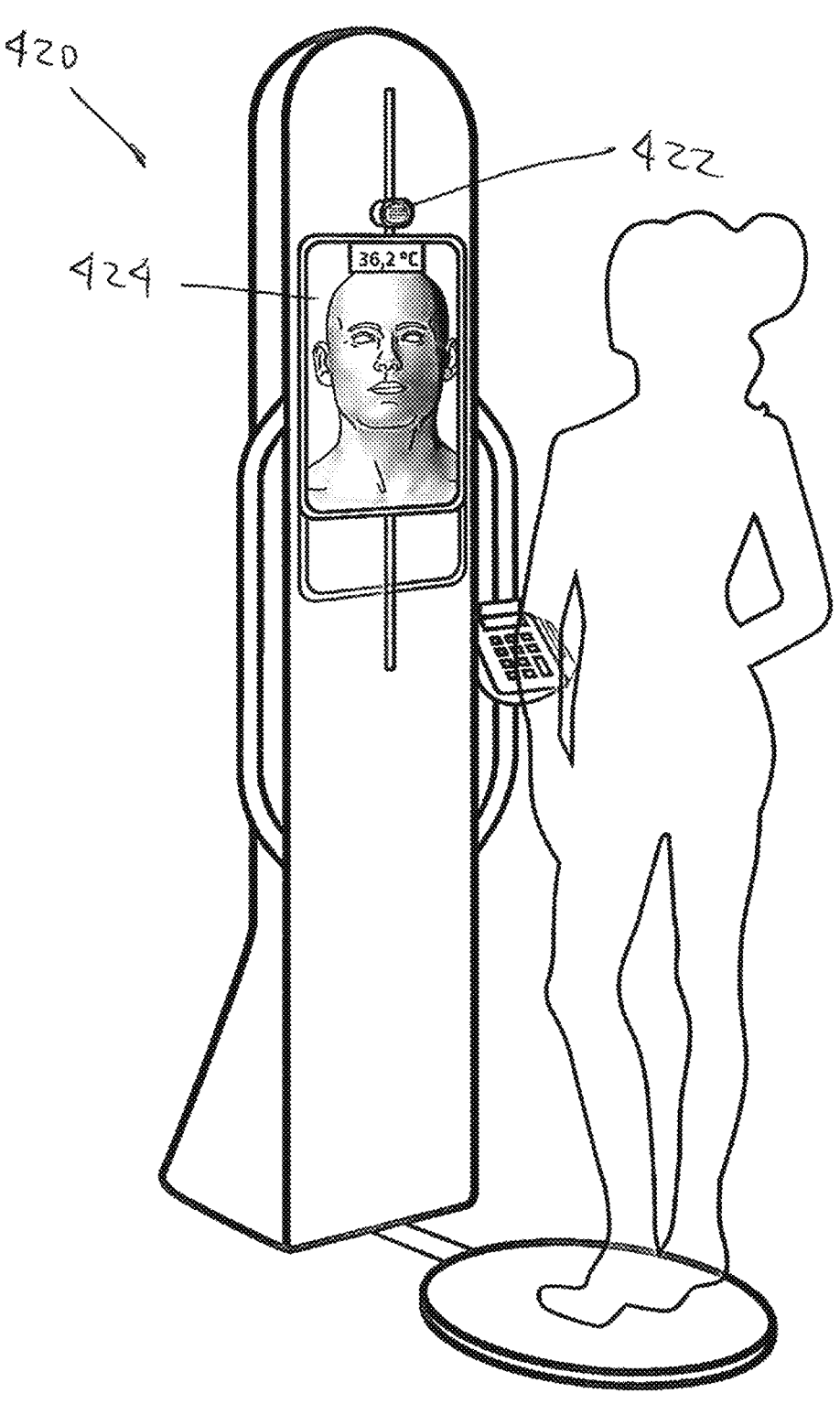

FIG. 70C
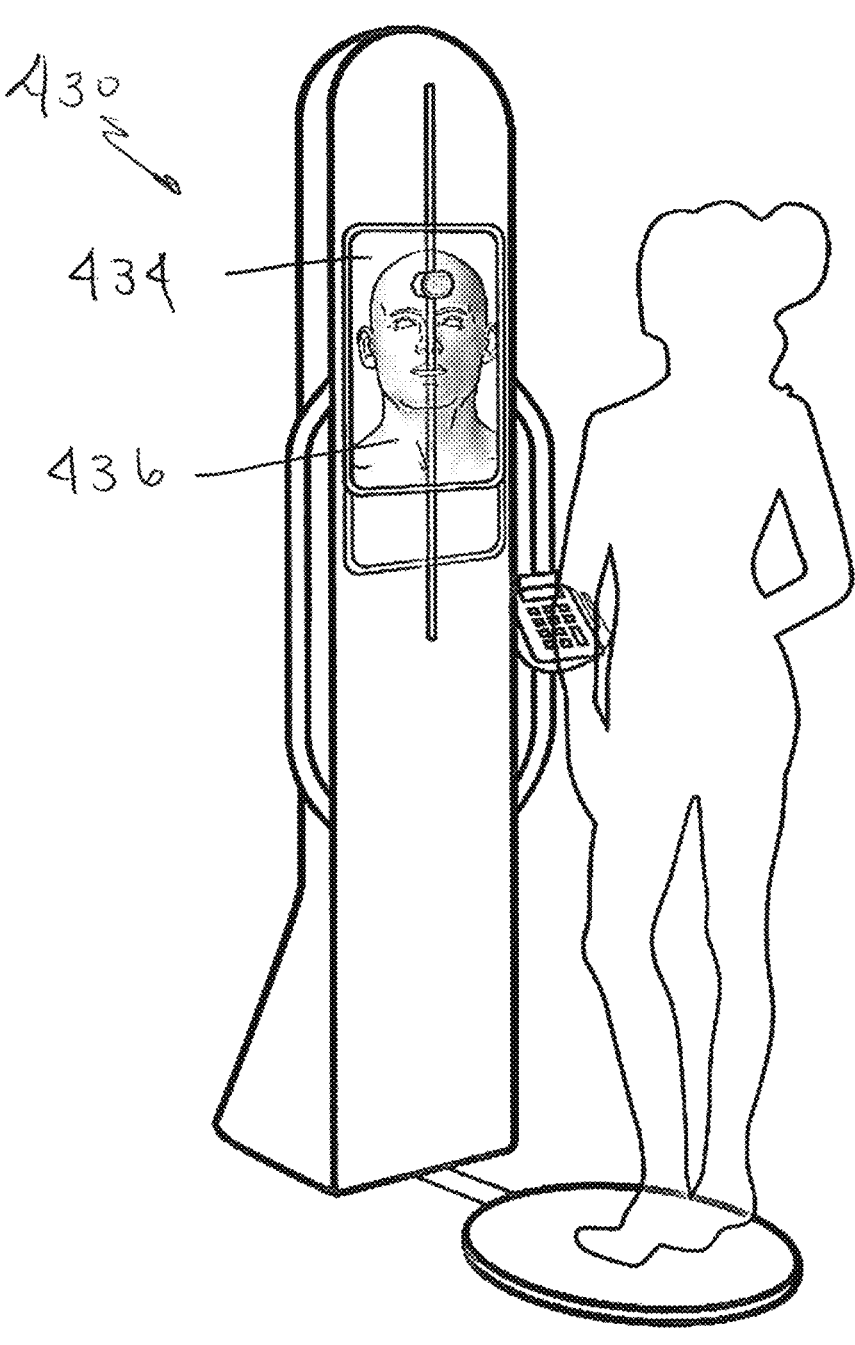

FIG. 70D
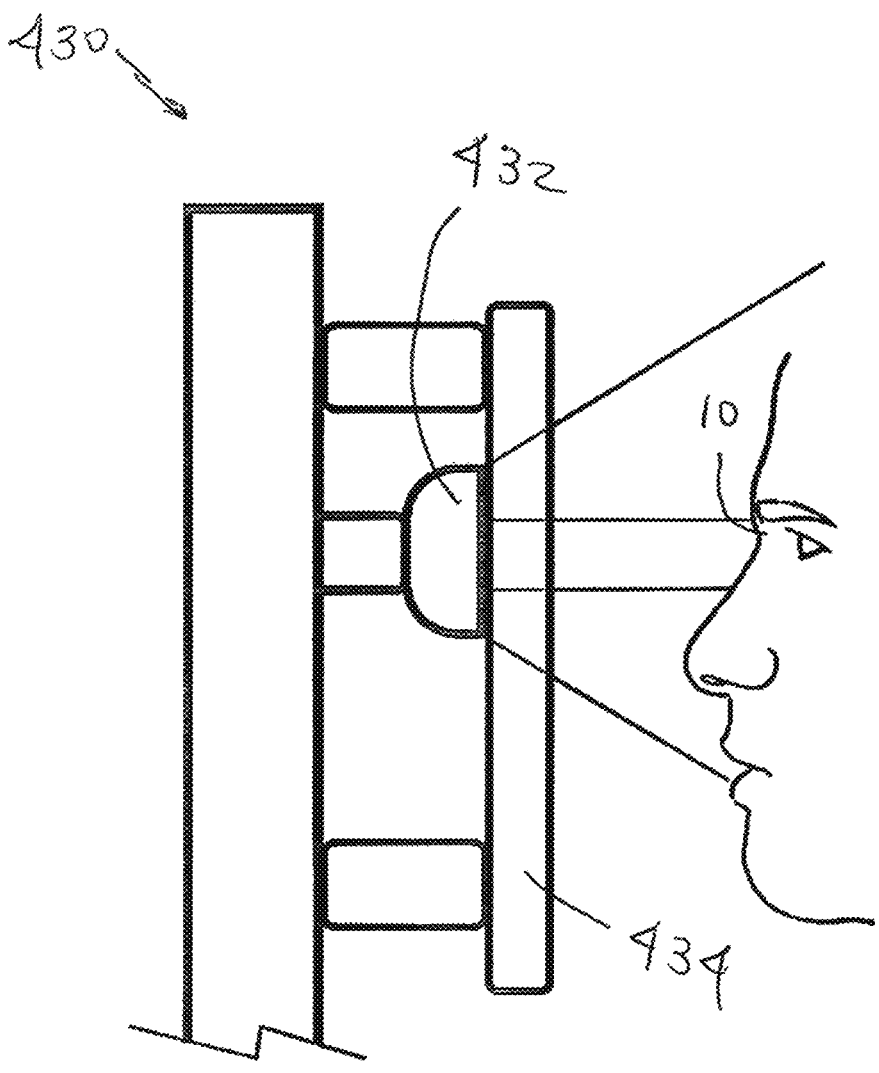

FIG. 70E
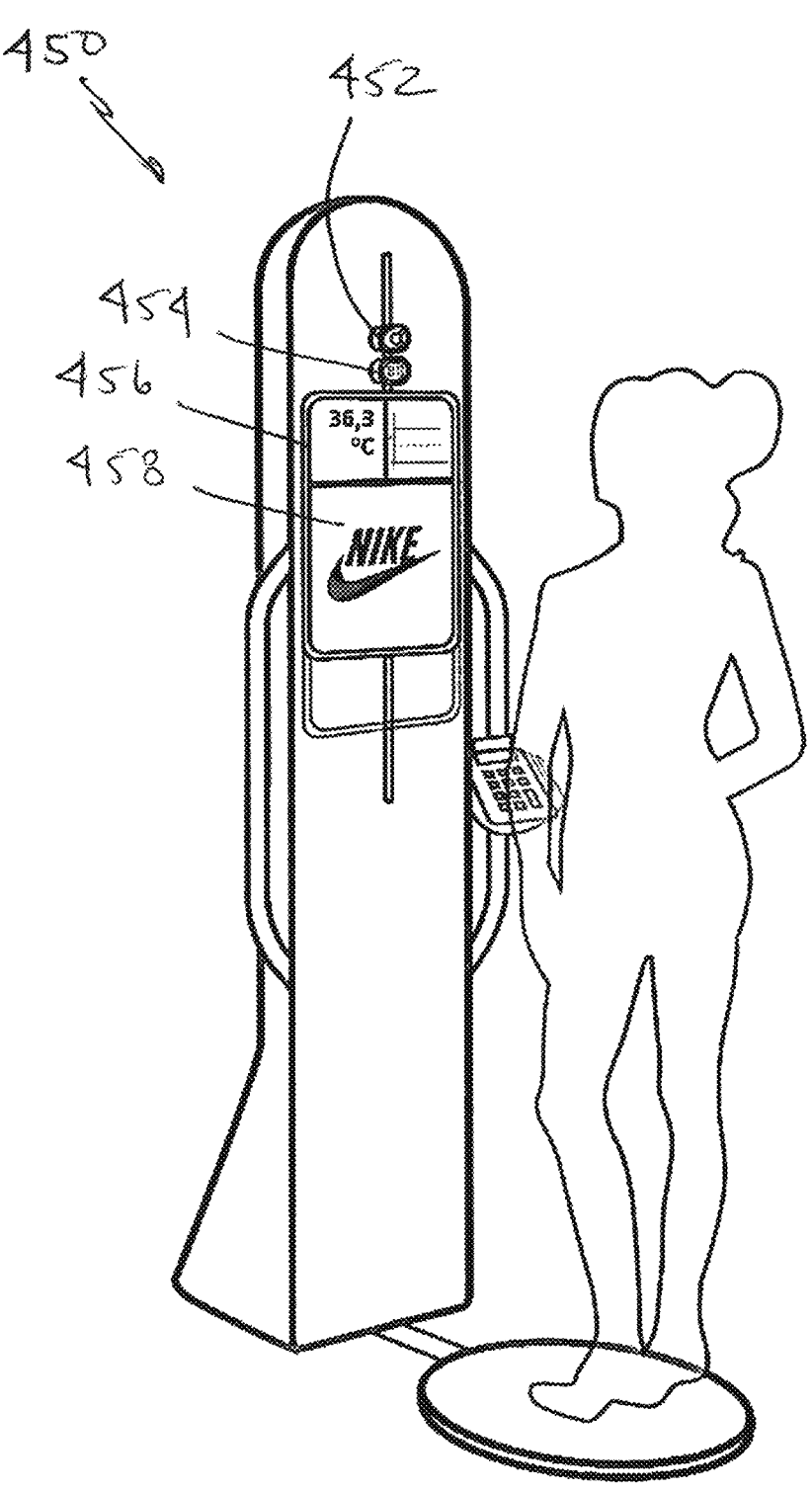

FIG, 70F
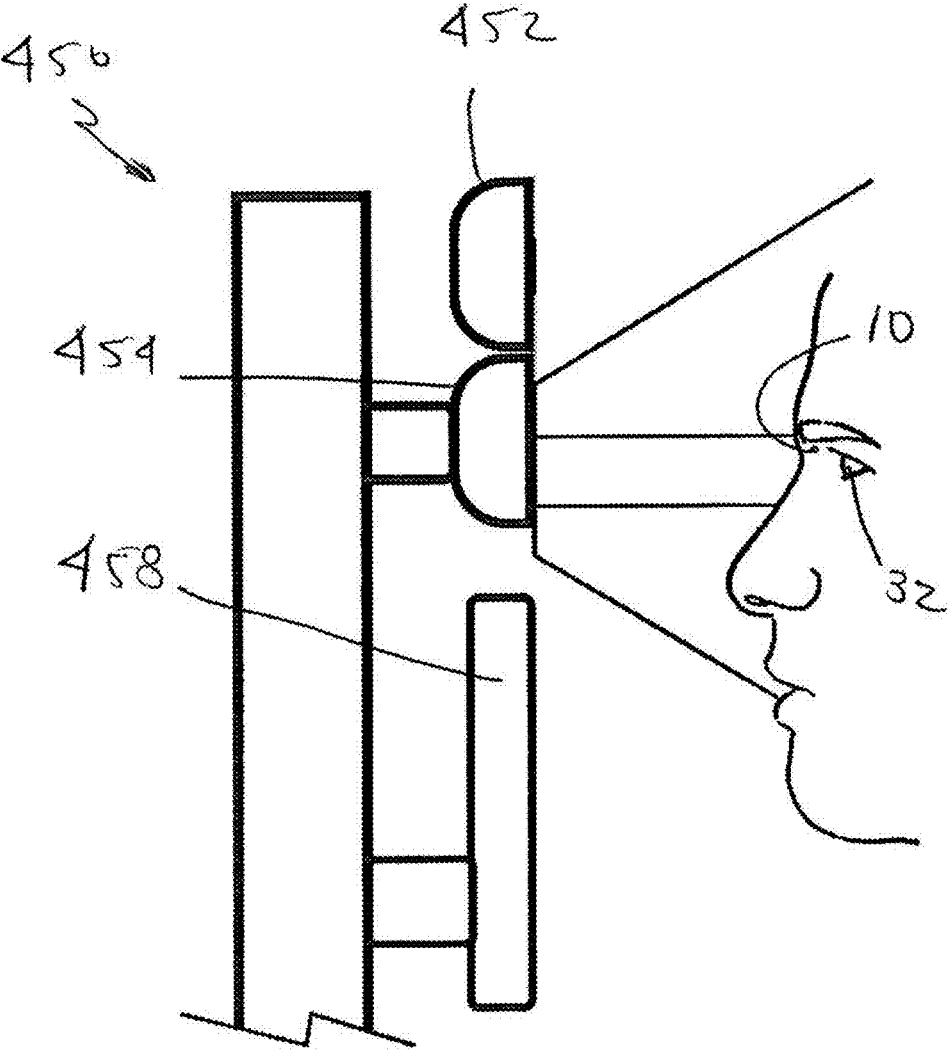

FIG. 70G
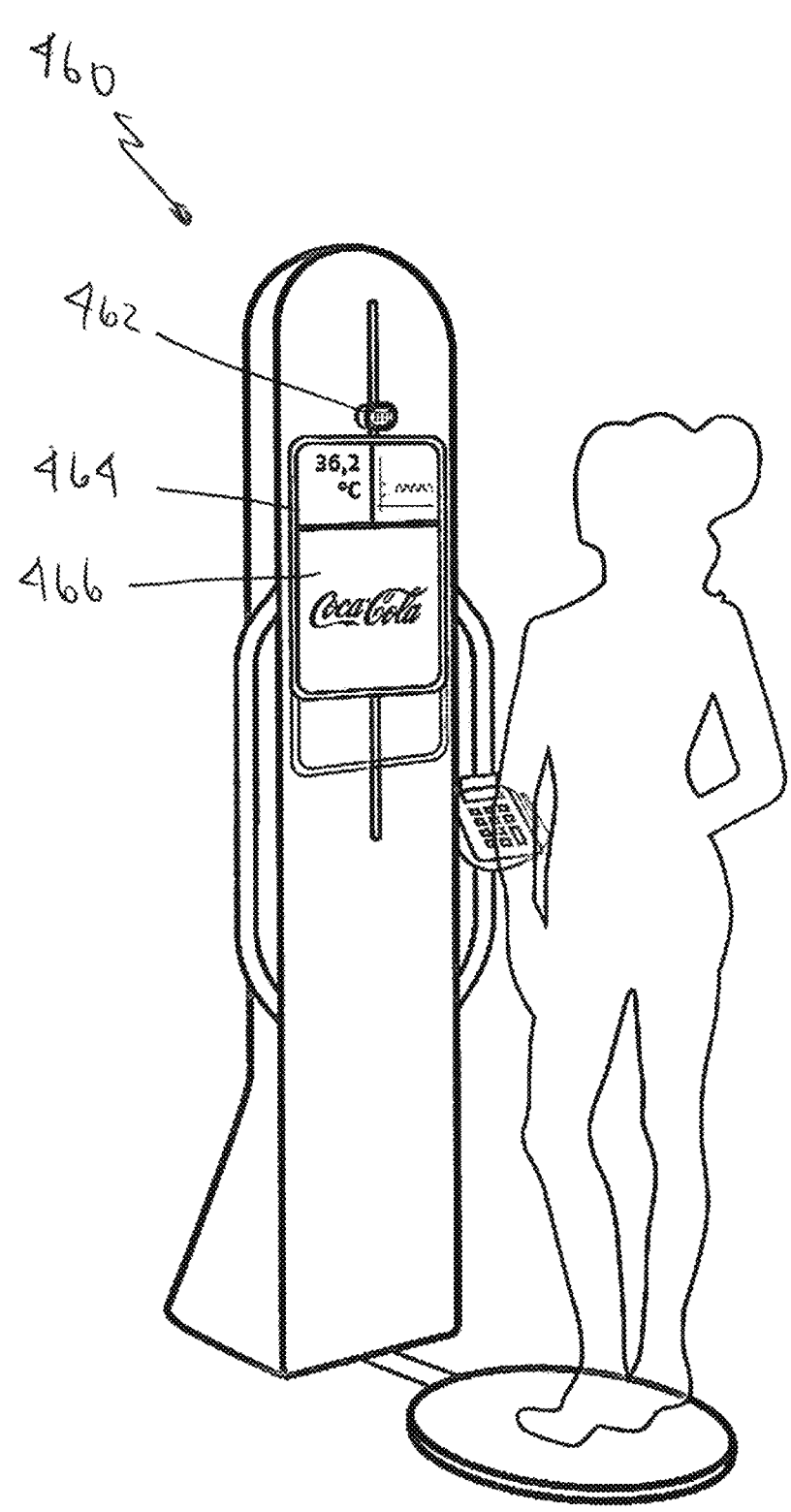

542
540
332
556
548

546
542
544

DEVICES, APPARATUSES AND SYSTEMS FOR MEASURING TEMPERATURE OF AN ABTT TERMINUS

CROSS-REFERENCE TO RELATED APPLICATIONS

This application is a divisional of U.S. patent application Ser. No. 18/389,313, filed on Nov. 14, 2023, which is a divisional of U.S. patent application Ser. No. 15/066,779, filed on Mar. 10, 2016, which claims the benefit of priority to U.S. Provisional Patent Application No. 62/131,131, filed Mar. 10, 2015, which are hereby incorporated by reference in their entirety.

TECHNICAL FIELD

This disclosure relates to devices configured to measure the temperature of one or more Abreu brain thermal tunnel (ABTT) terminuses.

BACKGROUND

Measurement of body temperature is conventionally accomplished by way of oral, axillary, forehead, or rectal thermometers.

SUMMARY

This disclosure provides a device for measuring a temperature of an Abreu brain thermal tunnel (ABTT). The device comprises a handle, a mirror, an arm, a temperature sensor positioned on the arm, and a display. The mirror includes a mirrored surface supported by the handle. The arm extends in a direction that is away from the mirror. The temperature sensor is sized and dimensioned to measure the temperature of an ABTT terminus. The temperature sensor is positioned on an end of the arm that is opposite from the mirror, and the temperature sensor is configured to provide a temperature measurement. The display is configured to receive and display the temperature measurement.

This disclosure also provides a device for locating an Abreu brain thermal tunnel (ABTT) and measuring thermal data from the ABTT. The device comprises a thermal imaging camera, a processor, and a display. The thermal imaging camera is configured to acquire a thermal image of a human face and to transmit the thermal image. The processor is configured to receive the transmitted thermal image, to analyze the thermal image to determine a location of an ABTT terminus, to then acquire thermal data from the ABTT terminus, to analyze the acquired thermal data, and to transmit the results of the analysis. The display is configured to receive the results of the analysis and to display the results of the analysis.

This disclosure also provides a device for measuring a temperature of two Abreu brain thermal tunnels (ABTT's). The device comprises a first rotatable member, a first thermal sensor, and a rotatable member. The first thermal sensor is positioned on the device and sized and dimensioned to measure a thermal output of a first ABTT terminus. The first thermal sensor is oriented in a first direction. The second thermal sensor is supported by the device and sized and dimensioned to measure a thermal output of a second ABTT terminus. The second thermal sensor is oriented in a second direction. The first rotatable member is configured to support the first thermal sensor and the first rotatable member is movable to vary the distance between the first thermal sensor and the second thermal sensor.

This disclosure also provides a system for measuring the emission of at least one Abreu brain thermal tunnel terminus, the system comprising a sensor, a display, and a processor. The sensor is configured to receive the emissions and to transmit signals representative of the emissions during an interval of time. The processor is configured to receive the signal, to analyze the signal, and to provide an output representative of at least one of the signal and the analysis of the signal to the display. The processor is further configured to provide an output that includes an advertisement during the interval of time and during a time to receive the signal and to analyze the signal.

This disclosure also provides a method of acquiring, analyzing, and displaying data acquired from at least one Abreu brain thermal tunnel terminus. The method comprises receiving emissions from the at least one Abreu brain thermal tunnel terminus during an interval of time; transmitting signals representative of the emissions to a processor; analyzing the transmitted signals and presenting the results on a display; and displaying an advertisement during the interval of time.

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 6 shows a front view of another device configured to assist in locating an ABTT terminus and then to measure the temperature of the ABTT terminus in accordance with an exemplary embodiment of the present disclosure.

FIG. 7 shows a side view of the device of FIG. 6.

FIG. 7A shows a view of yet another device configured to assist in locating the ABTT terminus and then to measure the temperature of the ABTT terminus in accordance with an exemplary embodiment of the present disclosure.

FIG. 7B shows another view of the device of FIG. 7A.

FIG. 7C shows a view of still yet another device configured to assist in locating the ABTT terminus and then to measure the temperature of the ABTT terminus in accordance with an exemplary embodiment of the present disclosure.

FIG. 7F shows another view of the device of FIG. 7E.

FIG. 7G shows another view of the device of FIG. 7C.

FIG. 8 shows a view of yet another device configured to locate at least one ABTT terminus and then to measure the temperature of the at least one ABTT terminus, with the device in a first configuration, in accordance with an exemplary embodiment of the present disclosure.

FIG. 8A shows a view of yet an even further device configured to locate at least one ABTT terminus and then to measure the temperature of the at least one ABTT terminus in accordance with an exemplary embodiment of the present disclosure.

FIG. 8B shows a view of still an even further device configured to locate at least one ABTT terminus and then to measure the temperature of the at least one ABTT terminus in accordance with an exemplary embodiment of the present disclosure.

FIG. 9 shows another view of the device of FIG. 8, with the device in a second configuration.

FIG. 10 shows a side view of the device of FIG. 8.

FIG. 11 shows a perspective view of the device of FIG. 8.

FIG. 30A shows a view of the device of FIGS. 7C and 7D positioned on a swing arm support apparatus.

FIG. 30C shows a view of a screw-based mounting mechanism for the apparatus of FIG. 30A.

FIG. 33B shows a view of a card reader of the system of FIG. 33A.

FIG. 34 shows a view of a support structure for the system of FIG. 31, in accordance with an exemplary embodiment of the present disclosure.

FIG. 35 shows a side view of the support structure of FIG. 34.

FIG. 36 shows a view of an alternative embodiment support structure for the system of FIG. 31, in accordance with an exemplary embodiment of the present disclosure.

FIG. 37 shows a side view of the support structure of FIG. 36.

FIG. 40 shows a view of a support structure for the system of FIG. 38, in accordance with an exemplary embodiment of the present disclosure.

FIG. 41 shows a side view of the support structure of FIG. 40.

FIG. 42 shows a view of a device to control a camera position of the system of FIG. 38.

FIG. 46 shows a view of a support structure for the system of FIG. 43, in accordance with an exemplary embodiment of the present disclosure.

FIG. 47 shows a side view of the support structure of FIG. 46.

FIG. 48 shows a view of a device to control a camera position of the system of FIG. 43.

FIG. 50 shows another view of the system of FIG. 49.

FIG. 51 shows a further view of the system of FIG. 49.

FIG. 52 shows a view of a support structure for the system of FIG. 49, in accordance with an exemplary embodiment of the present disclosure.

FIG. 53 shows a side view of the support structure of FIG. 52.

FIG. 54 shows a view of a device to control a camera position of the system of FIG. 49.

FIG. 55 shows a view of an activation device of the system of FIG. 49.

FIG. 59 shows a view of a support structure for the system of FIG. 56, in accordance with an exemplary embodiment of the present disclosure.

FIG. 60 shows a side view of the support structure of FIG. 59.

FIG. 61 shows a view of a device to control a camera position of the system of FIG. 56.

FIG. 62 shows a view of an activation device of the system of FIG. 56.

FIG. 66 shows a view of a support structure for the system of FIG. 63, in accordance with an exemplary embodiment of the present disclosure.

FIG. 67 shows a side view of the support structure of FIG. 66.

FIG. 68 shows a view of a device to control a camera position of the system of FIG. 63.

FIG. 69 shows a view of an activation device of the system of FIG. 63.

FIG. 70A shows a view of yet another system configured to locate an ABTT terminus and then to measure the temperature of the ABTT terminus, in accordance with an exemplary embodiment of the present disclosure.

FIG. 70C shows a view of still yet another system configured to locate an ABTT terminus and then to measure the temperature of the ABTT terminus, in accordance with an exemplary embodiment of the present disclosure.

FIG. 70D shows a view of a portion of the system of FIG. 70C.

FIG. 70E shows a view of an even further system configured to locate an ABTT terminus and then to measure the temperature of the ABTT terminus, in accordance with an exemplary embodiment of the present disclosure.

FIG. 70F shows a view of a portion of the system of FIG. 70E.

FIG. 70G shows a view of an even further system configured to locate an ABTT terminus and then to measure the temperature of the ABTT terminus, in accordance with an exemplary embodiment of the present disclosure.

FIG. 70L shows a view of a system configured to locate an ABTT terminus and then to measure the temperature of the ABTT terminus, in accordance with an exemplary embodiment of the present disclosure.

FIG. 70M shows a view of a sensor device of the system of FIG. 70L.

FIG. 70N shows a view of another sensor device in accordance with an exemplary embodiment of the present disclosure.

FIG. 70O shows a view of a further sensor device in accordance with an exemplary embodiment of the present disclosure.

FIG. 70P shows a view of an even further sensor device in accordance with an exemplary embodiment of the present disclosure.

FIG. 70Q shows a view of the system of FIG. 70L with modified features.

SUMMARY

Figures 1, 2:
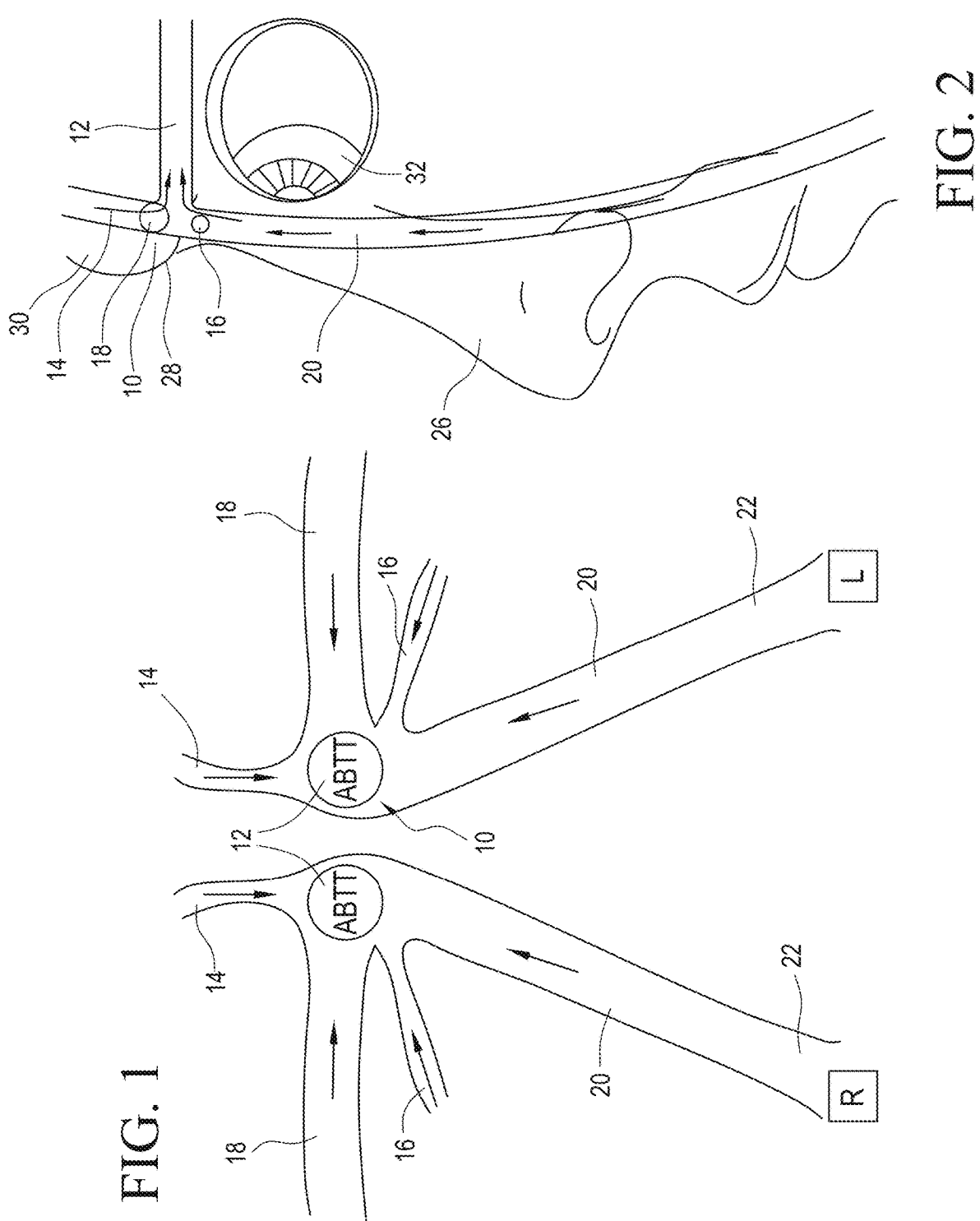
FIG. 1 shows a simplified view of the ABTT and facial veins associated with the ABTT.
FIG. 2 shows a simplified partial cross-sectional view through a human skull in a vertical direction, showing the Abreu brain thermal tunnel and certain other facial features.
Figure 3:
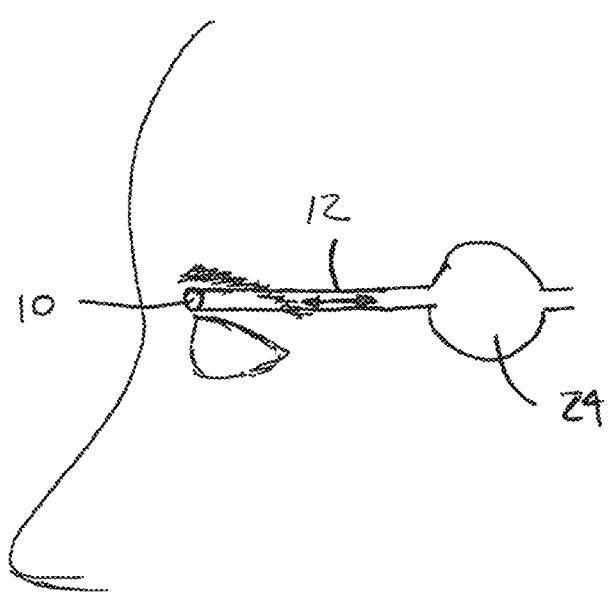
FIG. 3 shows a stylized representation of the flow of blood into a brain core.

The present disclosure arises from the discovery that an Abreu brain thermal tunnel or ABTT provides the first known means of vascular communication directly with the center of the brain. Anatomically and physiologically speaking, and as shown in FIGS. 1-3, ABTT 12 includes a continuous, direct, and undisturbed connection between a brain core 24 at the control center of the brain and an ABTT terminus 10. The physical and physiological events at one end of the tunnel are reproduced at the opposite end. ABTT 12 enables the direct communication of thermal energy between ABTT terminus 10 and brain core 24 without significant barriers. Accordingly, the present disclosure describes apparatus, systems, devices, mechanisms, and methods that are used to locate ABTT terminus 10 and then to measure the temperature of ABTT terminus 10.

Applicant has disclosed other devices, apparatuses, and systems for the measurement of temperature at ABTT terminus 10 in co-pending U.S. patent application Ser. Nos. 14/512,421, 14/593,848, 14/594,122, and 14/603,353. The present apparatuses, systems, devices, mechanisms, and methods described herein provide additional features and advantages, as will be understood by a person of skill in the art from reading the description provided herein.

The facial end of ABTT 12, herein referred to as target area, or terminus 10 on the skin on, over, or adjacent to ABTT 12, measures about 11 mm in diameter measured from the medial corner of an eye 32 at the medial canthal tendon and extends superiorly for about 6 mm, and then extends into the upper eyelid in a horn-like projection for another 22 mm.

Anatomy shows the convergence of four veins at ABTT target area 10: frontal 14, superior palpebral 16, supraorbital 18, and angular 20. As angular vein 20 extends further from ABTT 12, it transitions into facial vein 22. Having converged, the blood from these veins flows toward brain core 24 from ABTT target area 10 near the canthal corner of eye 32 into the center of the brain, which is the temperature center or thermal storage area of the body. FIGS. 1 and 2 show the approximate location of these veins in relation to other facial features. Angular/facial vein 20/22 runs up alongside nose 26, superior palpebral vein 16 runs along eyebrow 28, and frontal vein 14 and supraorbital vein 18 run through forehead 30.

As described herein, veins 14, 16, 18, 20, and 22 converge in the medial canthal area between the corner of eye 32 and the bridge of the nose and connect directly, without inhibition, to the center of the brain. These vessels lack valves, which are typically an important barrier to measurement of temperature in a core location of the brain in the hypothalamic region of the brain. The hypothalamic region of the brain is the link between the central nervous system and the endocrine system and, as such, acts as the center of control for many basic bodily functions such as, for example, hunger, thirst, body temperature, fatigue, blood pressure, immune responses, circadian cycles, hormone production and secretion, and many others.

Figures 4, 5:
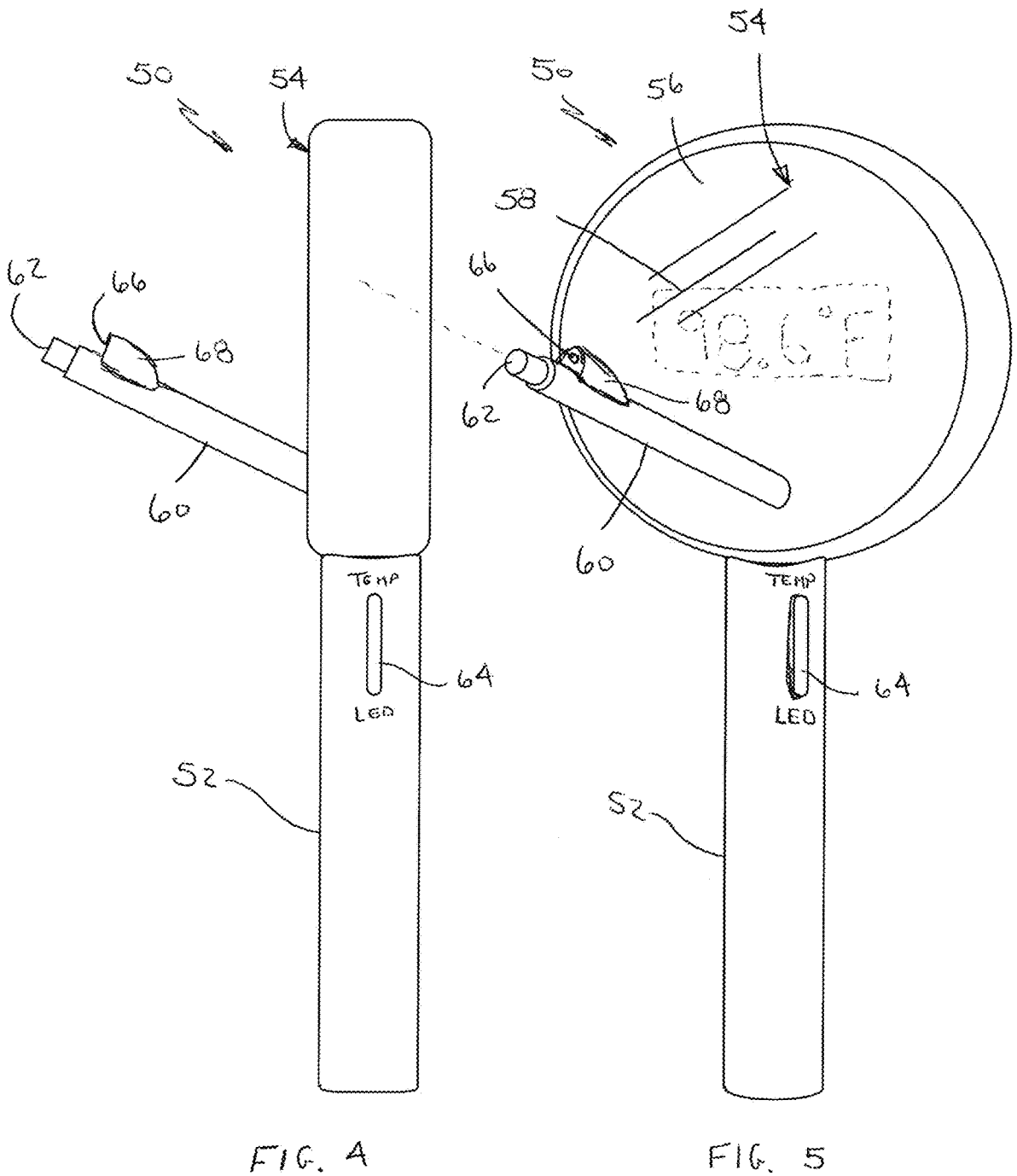
FIG. 4 shows a side view of a device configured to assist in locating an ABTT terminus and then measure the temperature at the ABTT terminus in accordance with an exemplary embodiment of the present disclosure.
FIG. 5 shows a perspective view of the device of FIG. 4.

Referring to FIGS. 4 and 5, an ABTT temperature measurement device in accordance with an exemplary embodiment of the present disclosure is shown and indicated generally at 50. Device 50 includes a handle 52 that is configured to support a mirror 54, which includes a partially reflecting mirrored or reflective surface 56. Device 50 is further configured to include a display 58, which can be positioned behind reflective surface 56, which is partially reflecting to permit light to travel through reflective surface 56 to enable display 58 to be seen by a user, when display 58 is illuminated.

Device 50 is also configured to include an arm 60 that extends in a direction that is away from mirrored or reflective surface 56, and is preferably at an angle with respect to surface 56 that matches an angle of ABTT terminus 10. While arm 60 is shown extending from surface 56 in FIGS. 4 and 5, in another exemplary embodiment arm 60 is configured to extend from handle 52. Arm 60 is configured to include a temperature sensor 62 at an end thereof, and the size and dimension of arm 60 is such that temperature sensor 62 is positioned near a center of mirrored surface 56 to enable the user to more easily use mirrored surface 56 to assist in positioning temperature sensor 62 at, near, on, adjacent, close, or alongside ABTT terminus 10. Device 50 further includes a switch 64, which can be located on handle 52. Switch 64 is configured to operate temperature sensor 62, with a resulting temperature measurement being presented on display 58. It should be understood that other sensors besides temperature can be used including infrared detector coupled to an emitter.

Device 50 can also be configured to include a light source such as a collimated LED 66 configured to emit visible light; i.e., a visible output. LED 66 is located in an LED housing 68, which can be positioned on arm 60. Switch 64 can be configured as a rocker-type switch that operates LED 66 in a first position, and operates LED 66 and temperature sensor 62 in a second position. Display 58 is operated automatically as a result of the operation of LED 66 and temperature sensor 62.

In operation, a user grasps handle 52, and by using mirror 54, positions temperature sensor 62 in an area that is adjacent to, meaning over or next to, ABTT terminus 10. In an exemplary embodiment, temperature sensor 62 can be a non-contact sensor, such as an infrared sensor, or can be a contact sensor, such as a thermocouple or thermopile, or an optical sensor or a dielectric sensor. If optional LED 66 is available, the user can press switch 64 to activate LED 66, which is boresighted or aligned with arm 60 such that light output from LED 66, as seen via mirror 54, can serve as a guide for positioning temperature sensor 62. Once temperature sensor 62 is properly placed, switch 64 may be moved to actuate temperature sensor 62. LED 66 can remain on during temperature measurement to assist in maintaining the position of temperature sensor 62. Device 50 may be configured to permit "scanning" of temperature sensor 62 to find the location of ABTT terminus 10. If device 50 includes this capability, once device 50 locates ABTT terminus 10, display 58 can be configured to display an appropriate indication, such as "ON TARGET." Once device 50 acquires a temperature measurement from ABTT terminus 10, the temperature result is presented on display 58, and the temperature result can remain on display 58 for a predetermined period, or can shutoff with release of switch 64.

Other devices to capture temperature from ABTT terminus 10 can include an infrared (IR) array configured to capture and analyze a face, and to automatically identify ABTT terminus 10 as well as provide the temperature at ABTT terminus 10. Such a temperature measurement device configured in accordance with an exemplary embodiment of the present disclosure is shown in FIGS. 6 and 7 and indicated generally at 100.

Device 100 is configured to include a handle 102 that is configured to support an IR imaging camera 104. Handle 102 can be configured to include a fingerprint recognition apparatus 106 as well as an operating switch 108. Device 100 can further be configured with an integral display (not shown), or can include a connector 110 that is configured to provide communication with an external electronic device, such as a laptop, cell phone, tablet, etc. (not shown). Device 100 can also include a transceiver, transmitter, or receiver to transmit information to an external electronic device. In an exemplary embodiment, infrared sensor array or IR imaging camera 104 can be configured to detect infrared light in the wavelength range of 8,200 to 11,200 nanometers.

Device 100 is operated by first grasping handle 102. If fingerprint recognition apparatus 106 is active, device 100 identifies the user to associate measured temperature data with a particular patient, and may also identify an authorized user. Once device 100 has provided the proper recognition, which may be indicated audibly, by display on a separate electronic device, or by illumination of an indicator (not shown) on device 100, acquisition of IR signals by camera 104 is available. Infrared light emitted from the ABTT carries brain diagnostic information within certain wavelengths, and IR imaging camera of the present disclosure is configured to preferably detect infrared light in the wavelength between 6,000 nanometers and 14,000 nanometers, and most preferably in the wavelength between 8,000 nanometers and 12,000 nanometers, and yet most preferably in the wavelength between 8,500 nanometers and 11,500 nanometers, and further yet most preferably between 8,200 nanometers and 11,200.

A user holds device 100 to aim at the area of the face that includes ABTT terminus 10, and presses operating switch 108. Because IR camera 104 has a relatively large field of view (FOV), camera 104 is able to image ABTT terminus 10 in addition to surrounding areas of the face. The image received by IR camera 104 may be transmitted to and processed within device 100 by a processor or controller (not shown), or the image may be transmitted as signals by a cable (not shown) attached to connector 110 to a separate electronic device, where the image data is processed to determine the temperature of ABTT terminus 10, as well as time varying temperature data. Additionally, the separate electronic device, which can be, for example, a laptop, tablet, cell phone, etc., can be configured to display the image, which can be useful for optimizing the position of device 100 as well as analyzing the image for thermal abnormalities, such as infection, poor blood flow, etc.

Figure 7D:
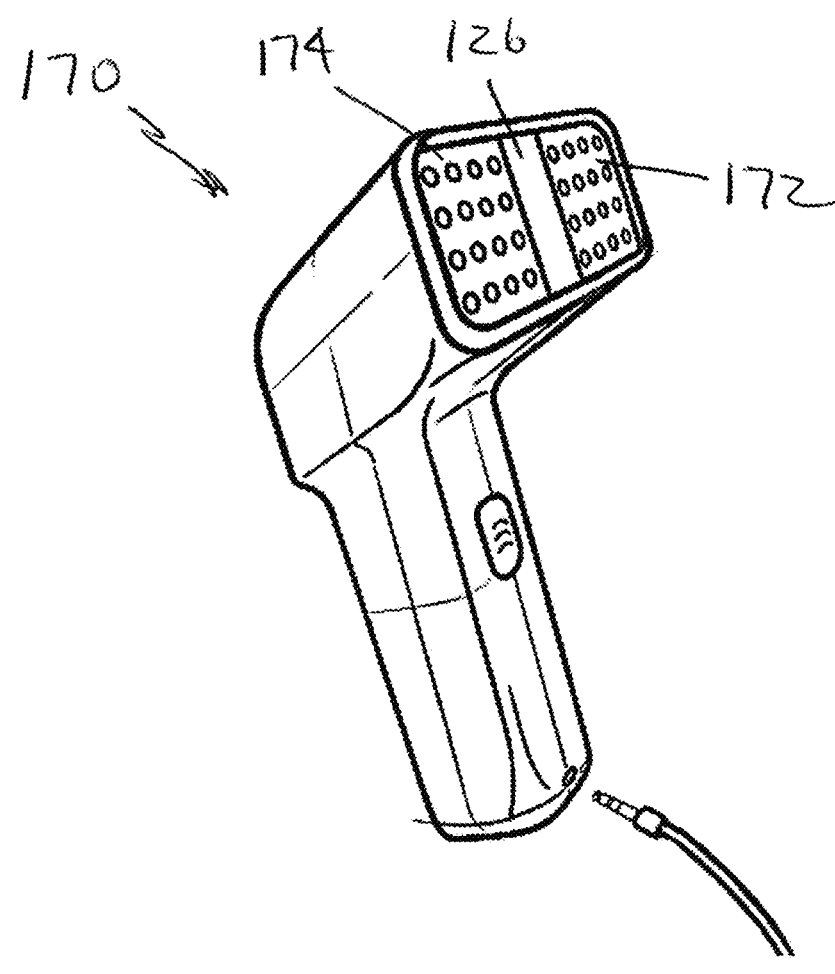
FIG. 7D shows another view of the device of FIG. 7C.
Figure 7E:
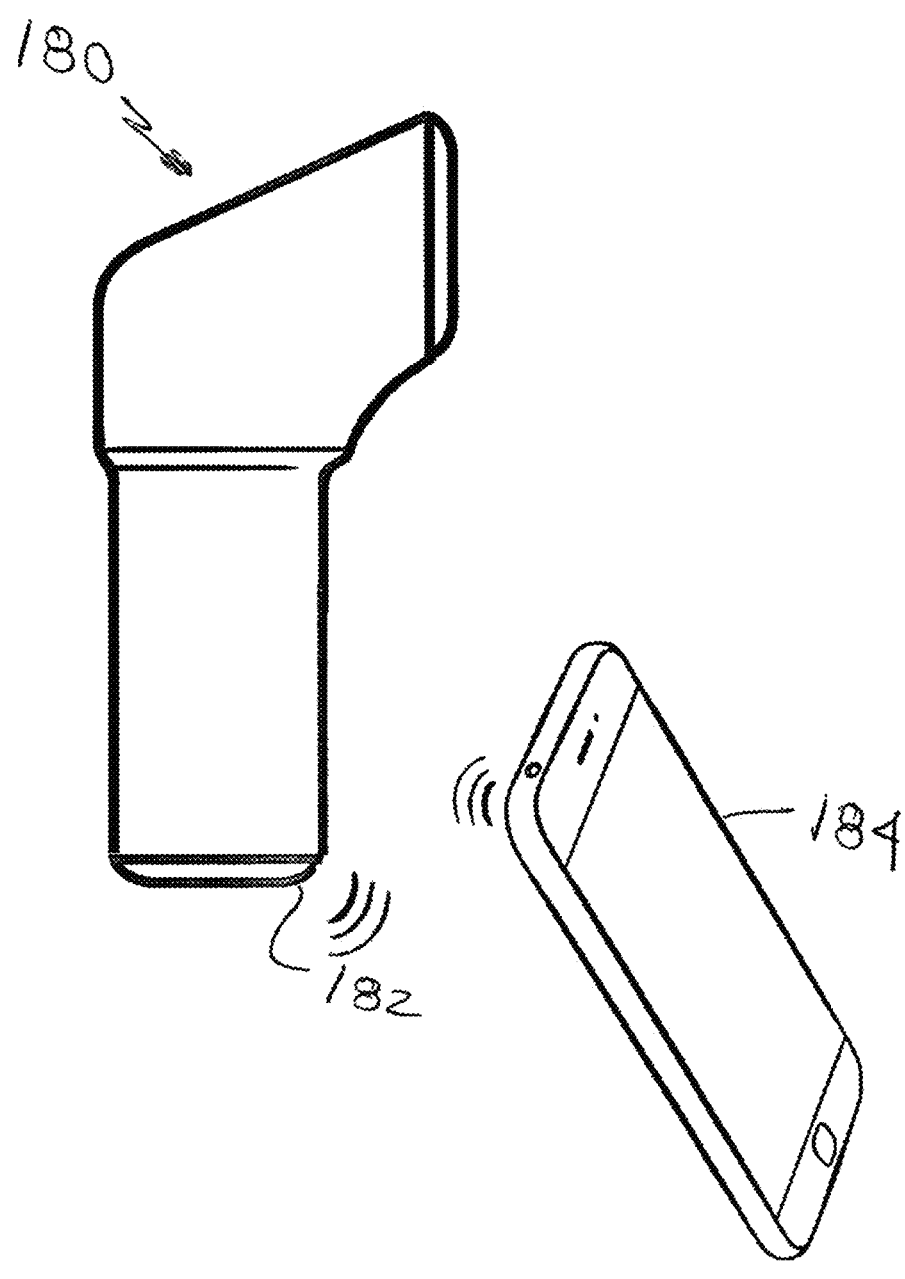
FIG. 7E shows a view of an even further device configured to assist in locating the ABTT terminus and then to measure the temperature of the ABTT terminus in accordance with an exemplary embodiment of the present disclosure.
Figure 7H:
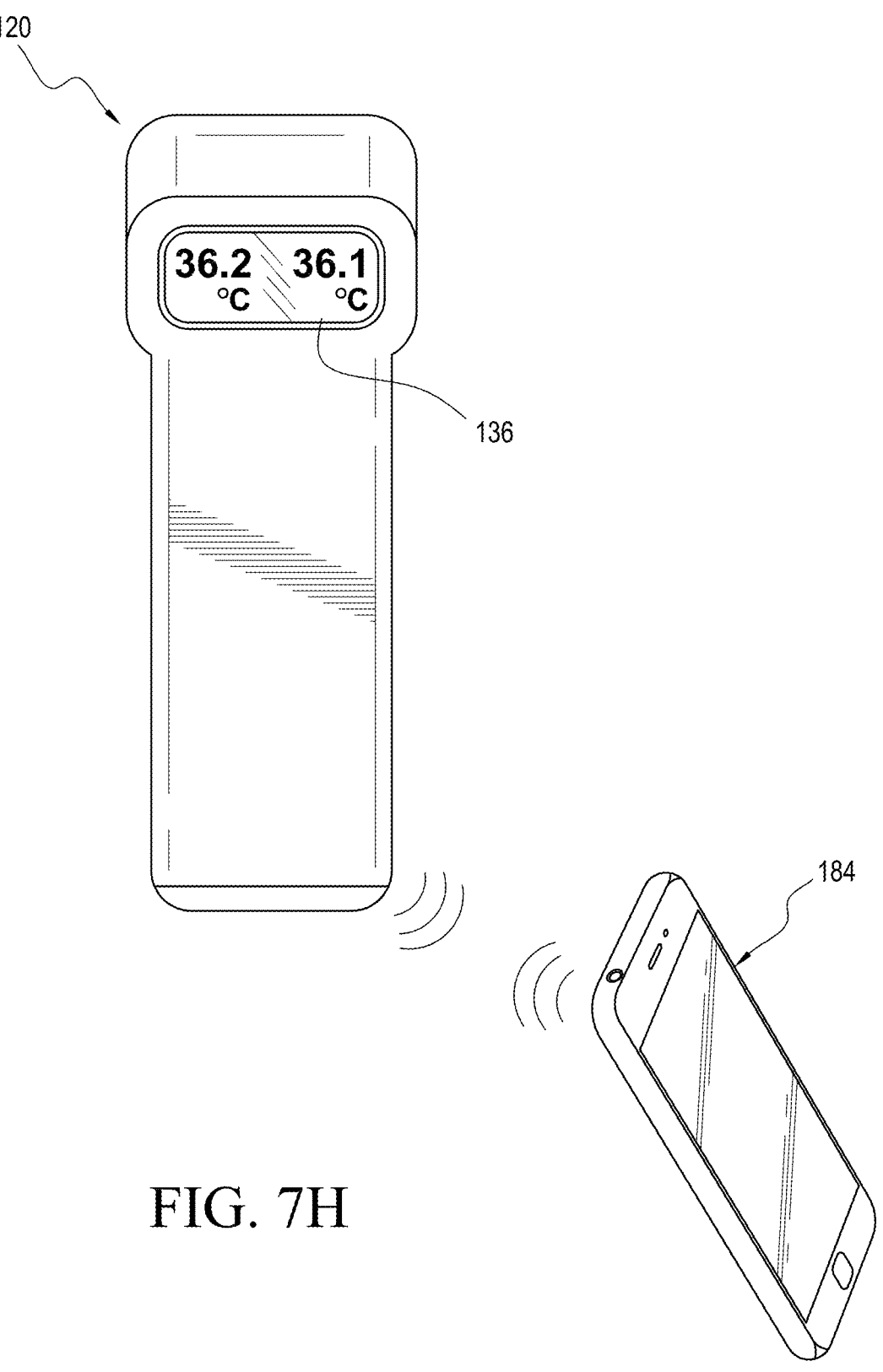
FIG. 7H shows another view of the device of FIG. 7A.
Figures 12, 13, 14, 15:
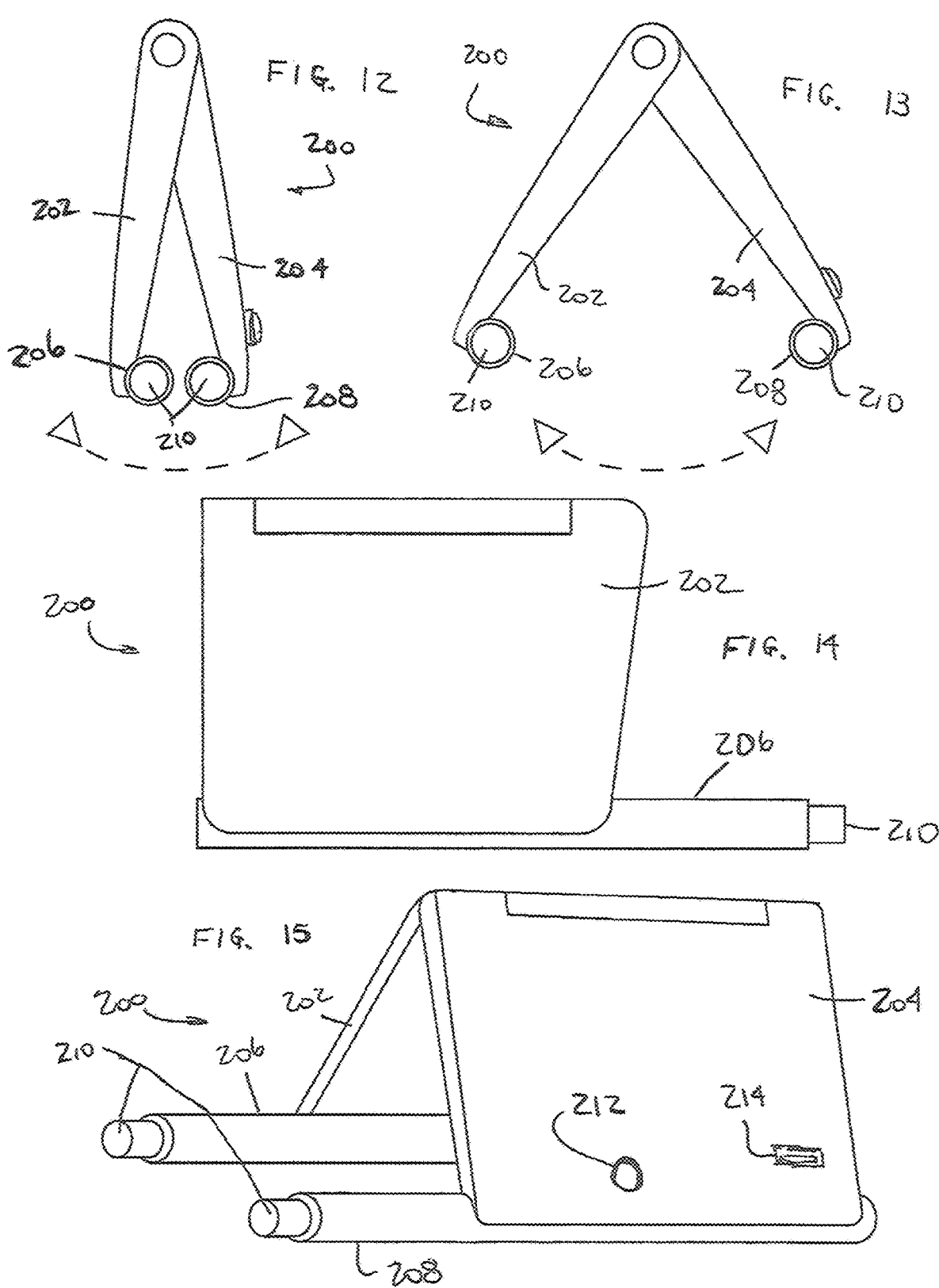
FIG. 12 shows a view of a device configured to measure the temperature of at least one ABTT terminus, with the device in a first position, in accordance with an exemplary embodiment of the present disclosure.
FIG. 13 shows another view of the device of FIG. 12, with the device in a second position.
FIG. 14 shows a side view of the device of FIG. 12.
FIG. 15 shows a perspective view of the device of FIG. 12.

FIGS. 7A, 7B, and 7H show views of yet another device, indicated generally at 120, configured to assist in locating ABTT terminus 10 and then to measure the temperature of ABTT terminus 10 in accordance with an exemplary embodiment of the present disclosure. Device 120 includes a right sensor 120 and a left sensor 122 separated by an extendable connecting portion 126 to adjust for different nose sizes. Temperature measurement device 120 also includes a processor 128, a transmitter (or transceiver) 130, a non-transitory memory 132, a power source 134, such as a battery, and a display 136. Display 136 is positioned on an opposite side of device 120 from right sensor 120 and left sensor 122. FIG. 7B shows device 120 with connecting portion 126 retracted to exemplarily adjust to a smaller nose size (or interpupillary distance). FIG. 7H shows simple display 136 displaying the temperature of right ABTT terminus 10 and of left ABTT terminus 10.

FIGS. 7C, 7D, and 7G show views of still yet another device, indicated generally at 170, configured to assist in locating ABTT terminus 10 and then to measure the temperature of ABTT terminus 10 in accordance with an exemplary embodiment of the present disclosure. Temperature measurement device 170 also includes processor 128 (which can be incorporated into any of the devices, apparatus, systems, etc., described herein), transmitter (or transceiver) 130, non-transitory memory 132, power source 134, such as a battery, a right display 176, and a left display 178. Right display 176 and left display 178 are positioned on an opposite side of device 170 from the sensors of device 170. FIG. 7D shows device 170 with connecting portion 126 retracted to exemplarily adjust to a smaller nose size (or interpupillary distance). FIG. 7G shows right display 176 and left display 178 on the back of device 170 capturing emissions from ABTT terminus 10, after device 170 has been adjusted and positioned to place sensor fields of view 190 on ABTT terminus 10. Right display 176 and left display 178 depict multiple pixels with stylized temperatures in the region of ABTT terminus 10, which includes a maximal temperature at ABTT terminus 10. It should be understood that a single display can be used in accordance to the principles of the present disclosure.

FIGS. 7E and 7F show views of an even further device, indicated generally at 180, configured to assist in locating ABTT terminus 10 and then to measure the temperature of ABTT terminus 10 in accordance with an exemplary embodiment of the present disclosure. Temperature measurement device 180 includes a transceiver 182 for communication with separate electronic device 184 (such as a cell phone), a right display 186, and a left array 188 positioned on an opposite side of device 180 from the sensors of device 180.

FIGS. 8-11 (excluding FIGS. 8A and 8B) show a temperature measurement device in accordance with an exemplary embodiment of the present disclosure, indicated generally at 150. Device 150 is configured with a device support 152, which rotatably supports a first device member 154 and a second device member 156. Device 150 is configured with at least one switch 158 to actuate a temperature measurement process by actuating temperature sensors (not shown) located within first device member 154 and second device member 156. Each device member 154 and 156 includes optics 160 such as lenses that are configured to gather a large FOV to make it easier to include ABTT terminus 10 as part of the FOV; i.e., when device 150 is held to a face, the diameter of optics 160 is such that when eyes 32 are centered on optics 160, optics 160 can also see ABTT terminus 10. Because first device member 154 and second device member 156 are configured to swivel or rotate, first device member 154 and second device member 156 can be adjusted to accommodate the variation in spacing of eyes 32 from each other. Device 150 may further include a connector 162 that is configured to permit connection of signals from device 150 to a separate electronic device (not shown), such as a laptop, tablet, cell phone, or the like. The separate electronic device can be configured to analyze the signals from device 150 and to display the results of the analysis, including display of temperature maps or images acquired by temperature sensors located within device 150.

FIG. 8A shows a view of yet an even further device, indicated generally at 220, configured to locate at least one ABTT terminus 10 and then to measure the temperature of the at least one ABTT terminus 10 in accordance with an exemplary embodiment of the present disclosure. Temperature measurement device 220 includes left sensor 222 and right sensor 224, each rotatably mounted on a front portion of device 220. Device 220 further includes a first optical member 226 and a second optical member 228, each having an outer periphery or edge 230. First optical member 226 and second optical member 228 are configured such that an open space or volume 232 is formed between first optical member 226 and second optical member 228. Each of first sensor 222 and second sensor 224 extend or protrude past outer periphery or edge 230 into space or volume 232 so as to be positioned to view ABTT terminus 10 when device 220 is placed on the face of a subject. Each of right sensor 222 and left sensor 224 include a sensor surface 234 that is adapted to view ABTT terminus 10, allowing eyes of user to see an image, hologram, virtual reality, and/or augmented reality displayed by way of first optical member 226 and second optical member 228, thereby allowing capturing a signal from ABTT terminus 10 while viewing an image provided by first optical member 226 and second optical member 228.

FIG. 8B shows a view of a portion of still an even further device, indicated generally at 240, configured to locate at least one ABTT terminus and then to measure the temperature of the at least one ABTT terminus in accordance with an exemplary embodiment of the present disclosure. Device 240 includes a single sensor, such as right sensor 224. In addition, device 240 indicates two of the plurality of optional positions available for right sensor 224 by way of the rotational mounting of right sensor 224. It should be understood that a variety of mechanisms including sliding and rotating can be used to align right sensor 224 with ABTT terminus 10.

FIGS. 12-15 show another temperature measurement device in accordance with an exemplary embodiment of the present disclosure, indicated generally at 200. Device 200 is configured with a first device member 202 and a second device member 204, which are rotatably connected to each other. First device member 202 includes a first arm 206 and second device member 204 includes a second arm 208. Each of first arm 206 and second arm 208 include a temperature sensor 210 positioned at an end thereof. Each temperature sensor 210 is oriented to face the same direction. Temperature sensors 210 are oriented to be parallel to each other. In addition, the outermost surface of temperature sensors 210 that measure the thermal output of ABTT terminus 10 is approximately co-planar. Each temperature sensor 210 is a spaced distance away from respective first device member 202 and second device member 204 to permit each temperature sensor 210 to be positioned adjacent to an ABTT terminus 10 without interference of first device member 202 and second device member 204 with an associated face. Device 200 is configured with at least one switch 212 to actuate a temperature measurement process by actuating temperature sensors 210. Because first device member 202 and second device member 204 are configured to swivel or rotate with respect to each other, first device member 202 and second device member 204 can be adjusted to accommodate the variation in spacing of eyes 32 from each other. Device 200 may further include a connector 214 that is configured to permit connection of signals from device 200 that originate from temperature sensors 210 to a separate electronic device (not shown), such as a laptop, tablet, cell phone, or the like. The separate electronic device can be configured to analyze the signals from device 200 and to display the results of the analysis.

Figures 16, 17, 18:
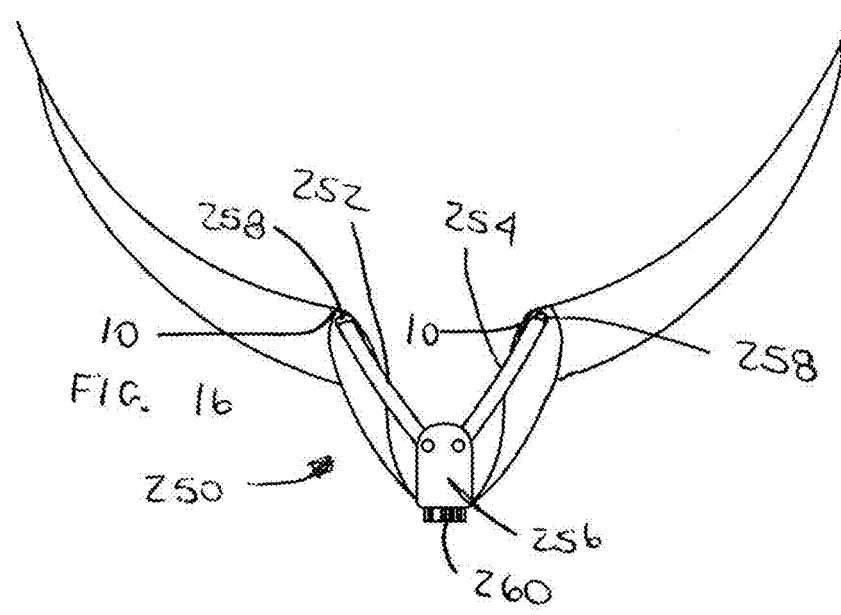
FIG. 16 shows a top view of another device configured to measure the temperature of at least one ABTT terminus, with the device positioned adjacent to a user's face, in accordance with an exemplary embodiment of the present disclosure.
FIG. 17 shows another view of the device of FIG. 16, showing a range of motion for portions of the device.
FIG. 18 shows a back view of the device of FIG. 16.

FIGS. 16-18 show another temperature measurement device in accordance with an exemplary embodiment of the present disclosure, indicated generally at 250. Device 250 is configured with a first device member 252 and a second device member 254, both of which are rotatably supported on a device support 256. As with devices 150 and 200, first device member 252 and second device member 254 are configured to swivel or rotate with respect to each other, such that first device member 252 and second device member 254 can be adjusted to accommodate the variation in spacing of eyes 32 from each other. First device member 252 and second device member 254 are each configured to support a temperature sensor 258. In the exemplary embodiment of FIGS. 16-18, first device member 252 and second device member 254 are configured to move independently with respect to each other. In another embodiment, first device member 252 and second device member 254 can be configured to move each other through a frictional or gear arrangement. In yet another embodiment, first device member 252 and second device member can be configured to slide laterally or transversely to change the spacing between first device member 252 and second device member 254. Device 250 is further configured to include a connector 260 that is configured to permit connection of signals from device 250 that originate from temperature sensors 258 to a separate electronic device (not shown), such as a laptop, tablet, cell phone, or the like. The separate electronic device can be configured to analyze the signals from device 250 and to display the results of the analysis.

Figure 19:
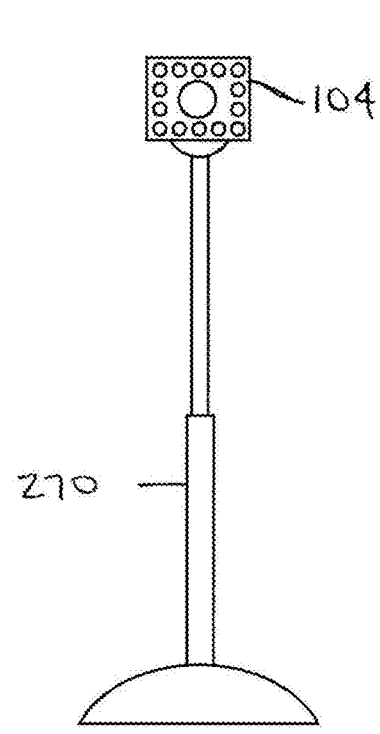
FIG. 19 shows a view of an apparatus configured to locate an ABTT terminus and then to measure the temperature of the ABTT terminus, in accordance with an exemplary embodiment of the present disclosure.
Figure 20:
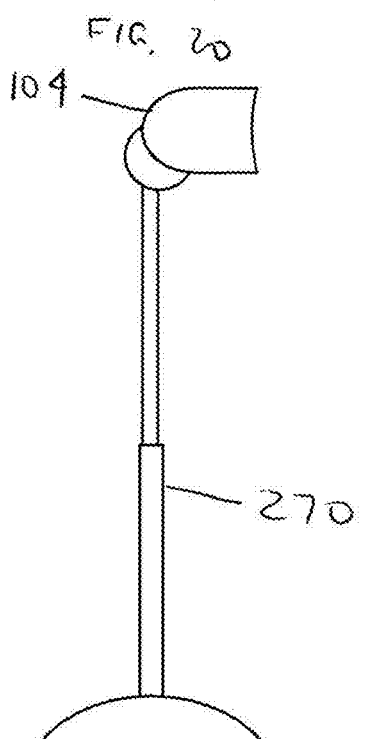
FIG. 20 shows a side view of the apparatus of FIG. 19.
Figure 21:
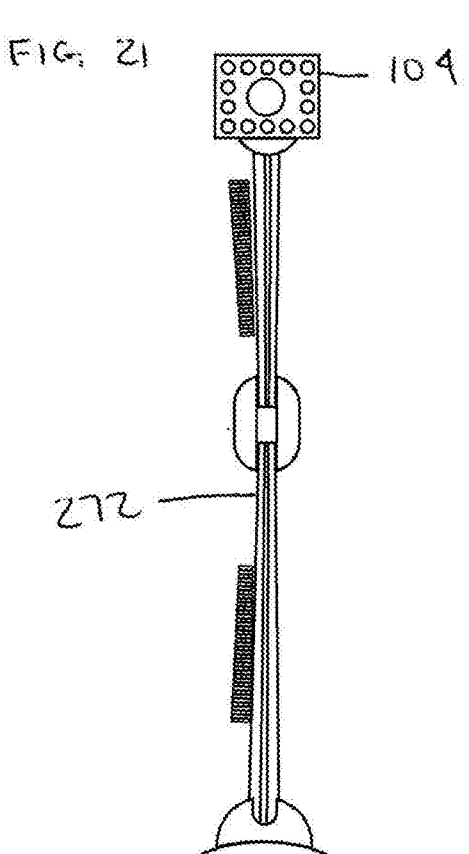
FIG. 21 shows a view of another apparatus configured to locate an ABTT terminus and then to measure the temperature of the ABTT terminus, in accordance with an exemplary embodiment of the present disclosure.
Figure 22:
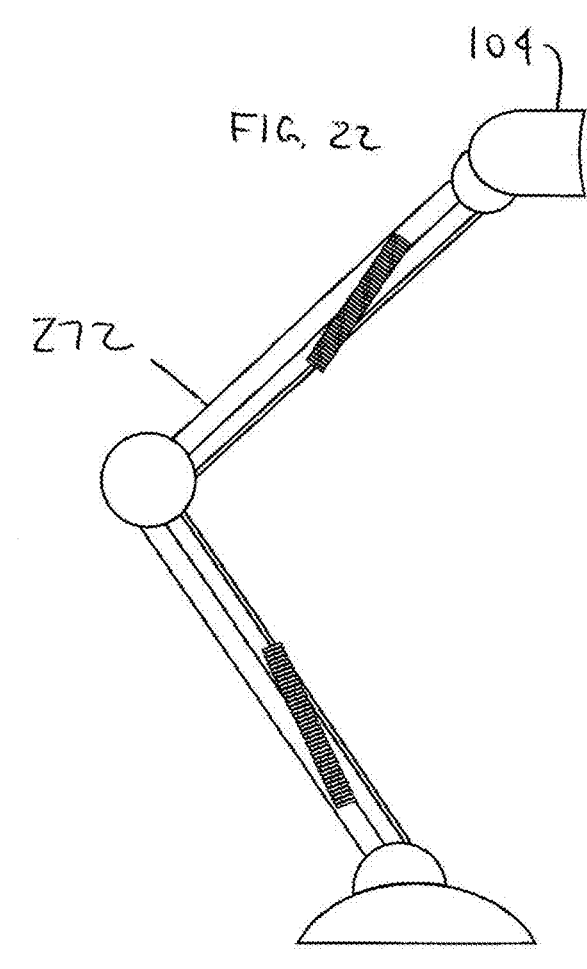
FIG. 22 shows a side view of the apparatus of FIG. 21.
Figure 23:
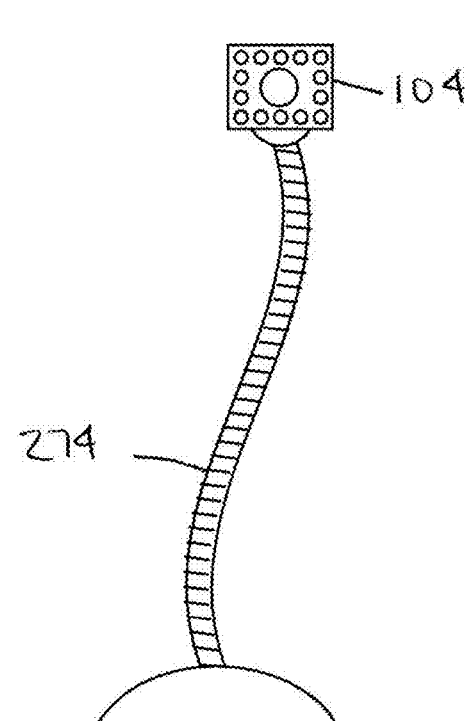
FIG. 23 shows a front view of yet another apparatus configured to locate an ABTT terminus and then to measure the temperature of the ABTT terminus, in accordance with an exemplary embodiment of the present disclosure.
Figure 24:
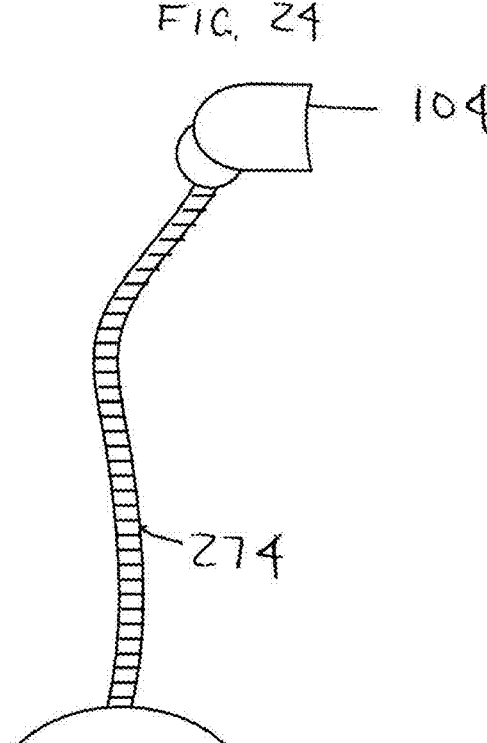
FIG. 24 shows a side view of the apparatus of FIG. 23.
Figure 25:
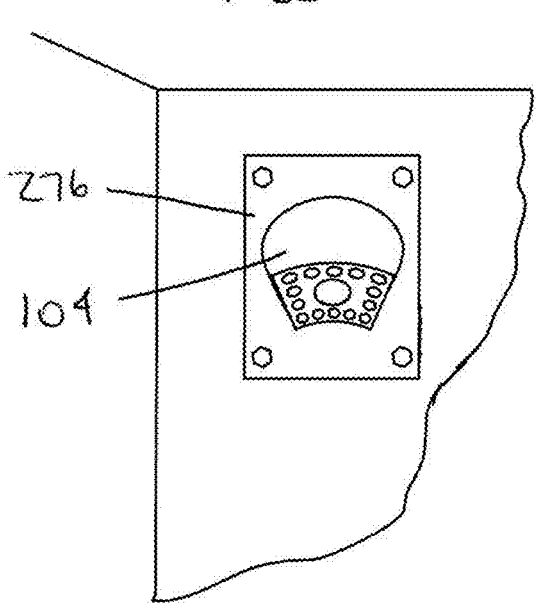
FIG. 25 shows a front view of a further apparatus configured to locate an ABTT terminus and then to measure the temperature of the ABTT terminus, in accordance with an exemplary embodiment of the present disclosure.
Figure 26:
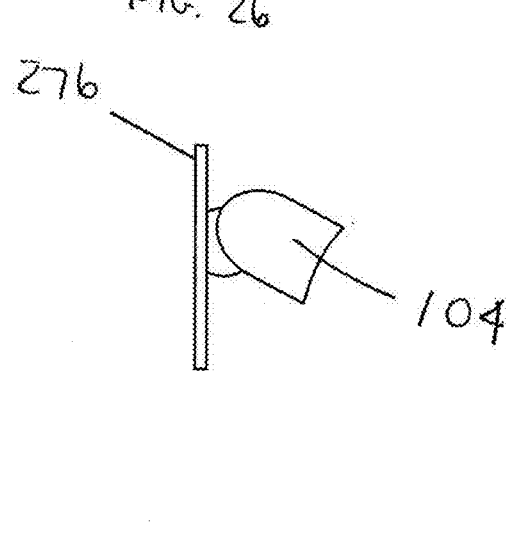
FIG. 26 shows a side view of the apparatus of FIG. 25.
Figure 27:
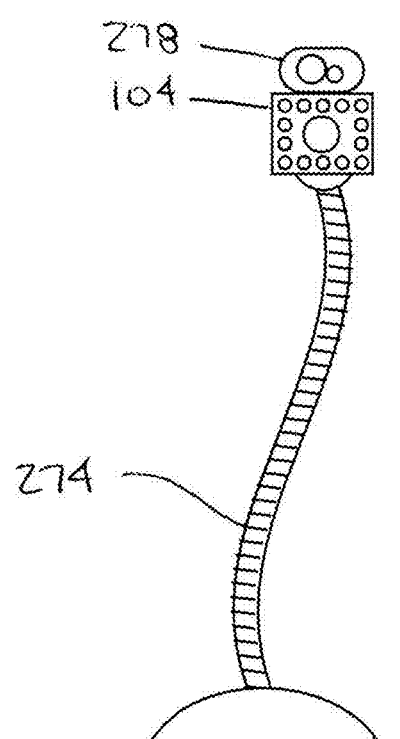
FIG. 27 shows a front view of a still further apparatus configured to locate an ABTT terminus and then to measure the temperature of the ABTT terminus, in accordance with an exemplary embodiment of the present disclosure.
Figure 28:
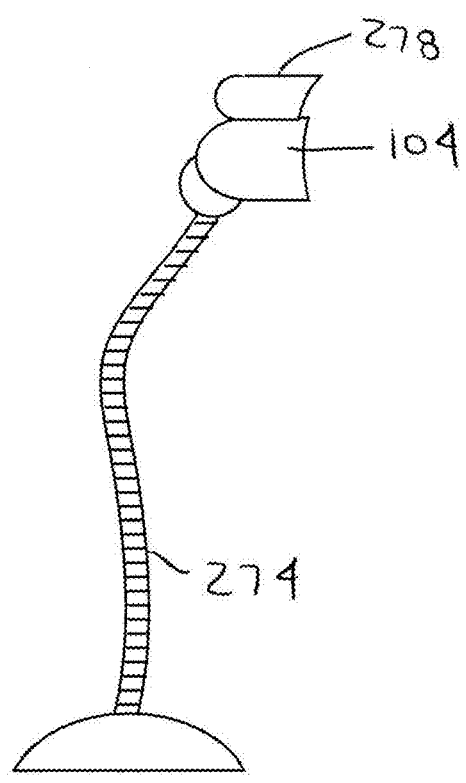
FIG. 28 shows a side view of the apparatus of FIG. 27.
Figure 29:
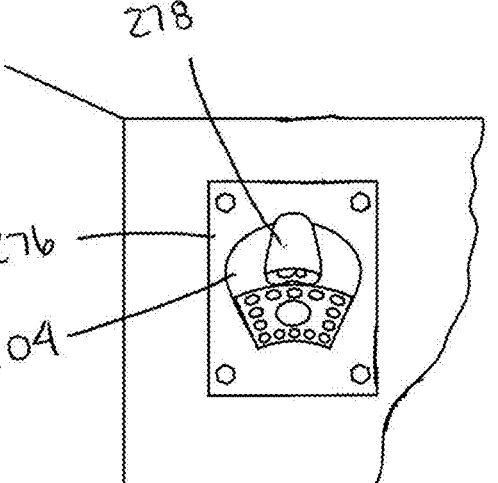
FIG. 29 shows a front view of an even further apparatus configured to locate an ABTT terminus and then to measure the temperature of the ABTT terminus, in accordance with an exemplary embodiment of the present disclosure.

IR camera imaging camera 104, shown positioned on a handle in FIGS. 6 and 7, can be mounted in other ways, such as are shown in FIGS. 19-26. FIGS. 19 and 20 show camera 104 positioned or located on a telescoping support 270 suitable to be positioned on a desk or table. FIGS. 21 and 22 show camera 104 positioned or located on a swing arm support 272. FIGS. 23 and 24 show camera 104 positioned or located on a goose neck support 274. FIGS. 25 and 26 show camera 104 positioned or located on a wall mount support 276.

Other devices may be collocated with camera 104. For example, FIGS. 27-30 show a configuration of camera 104 that includes a transceiver, transmitter, or receiver 278 configured to communicate with a separate electronic device, e.g., a laptop, cell phone, tablet, non-transitory storage medium, etc.

Figure 30:
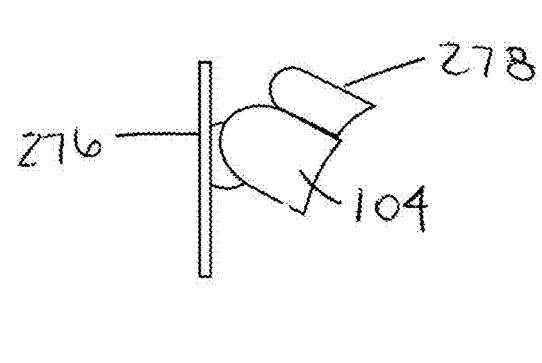
FIG. 30 shows a side view of the apparatus of FIG. 29.
Figure 30B:
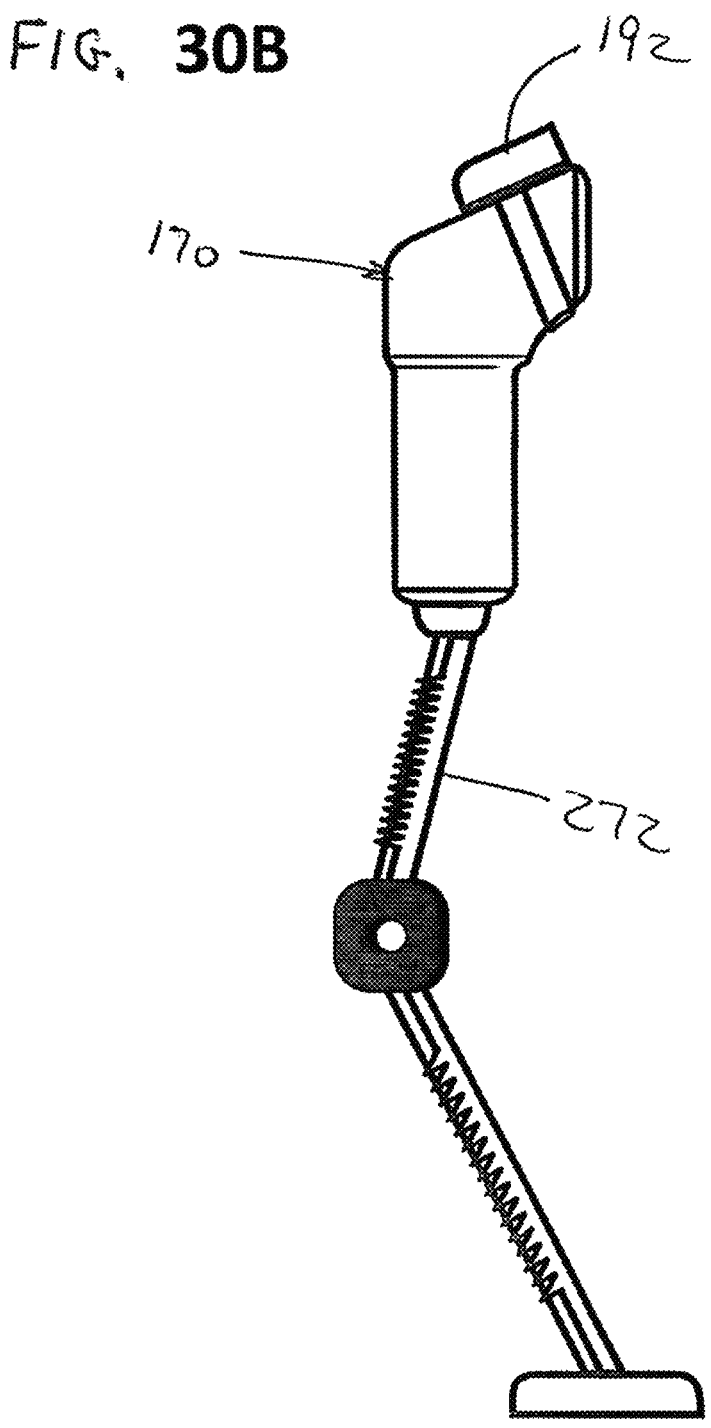
FIG. 30B shows another view of the device of FIG. 30A.

FIGS. 30A and 30B show device 170 of FIGS. 7C and 7D positioned on swing arm support 272 for adjustment to different heights of subjects being measured. In the embodiment of FIG. 30A, a digital camera 192 is positioned above right sensor array 172 and left sensor array 174, and said camera is adapted to superimpose a digital image on top of an infrared image to allow identification of certain anatomic landmarks in relation to the amount of thermal emission of said anatomic landmarks. FIG. 30B is a side view of the elements shown in FIG. 30A and shows shortening.

Figure 30D:
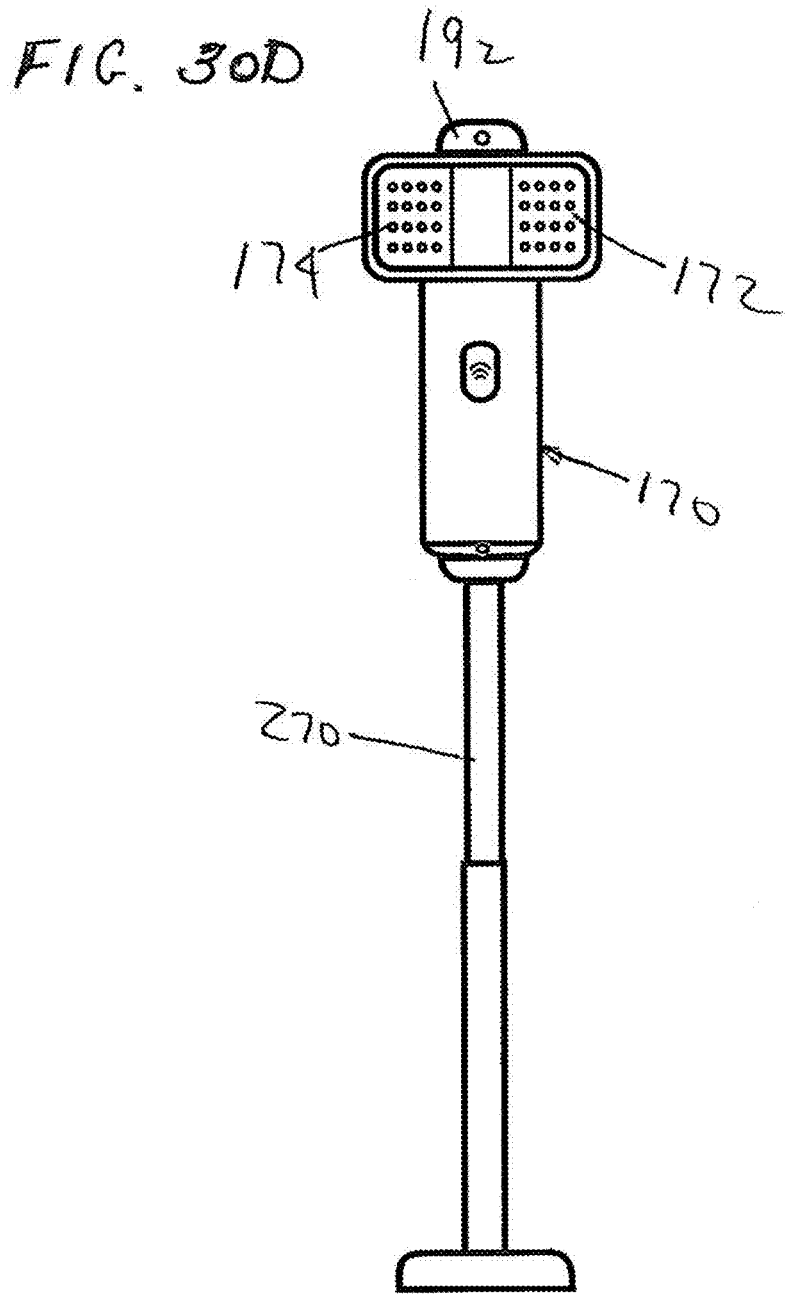
FIG. 30D shows a view of the device of FIGS. 7C and 7D positioned on a telescoping support.
Figure 30E:
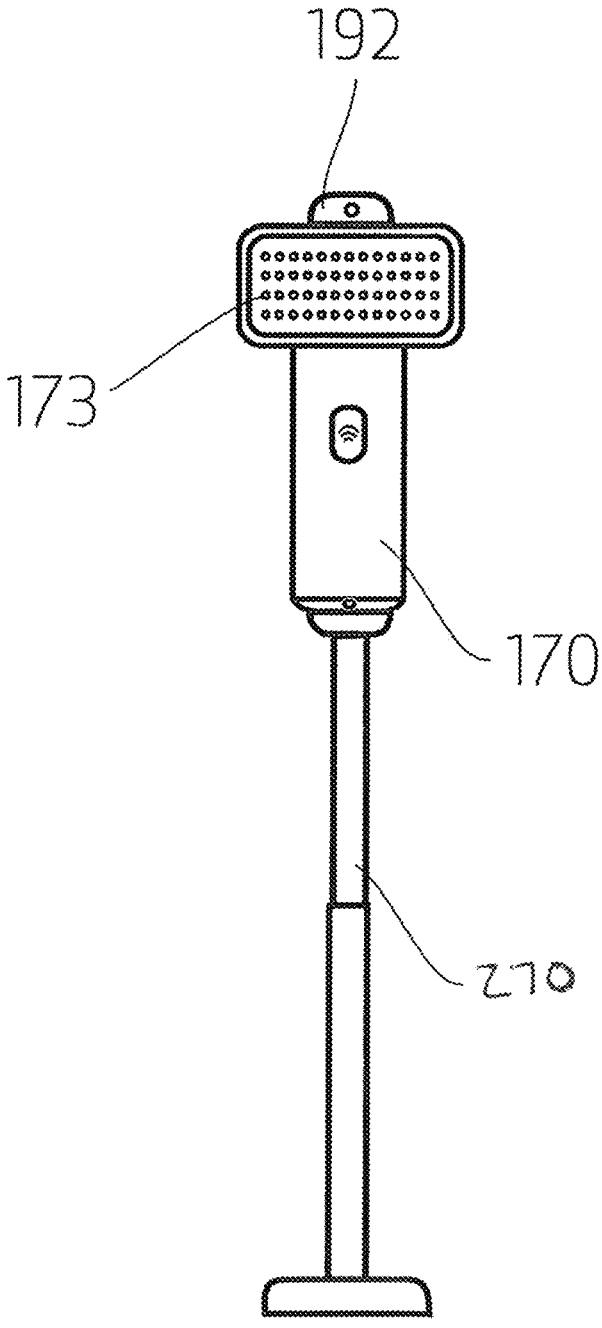
FIG. 30E shows a view of another device positioned on the telescoping support in accordance with an exemplary embodiment of the present disclosure.

FIGS. 30C and 30D show a screw-based mounting mechanism 194 for device 170. FIG. 30D shows device 170 positioned on telescoping support 270 for adjustment to different height of subjects being measured. Device 170 is configured similar to the arrangement of FIGS. 30A and 30B and includes digital camera 192 positioned above right sensor array 172 and left sensor array 174. Although infrared detector was shown as a dual detector or dual sensor array, right and left sensor arrays, it should be understood that one single array adapted to detect signal from both the right ABTT and the left ABTT can be used, and are shown in FIG. 30E as one single sensor array 173. It should also be understood that a single sensor array can be used in any embodiment of the present invention.

Figure 31:
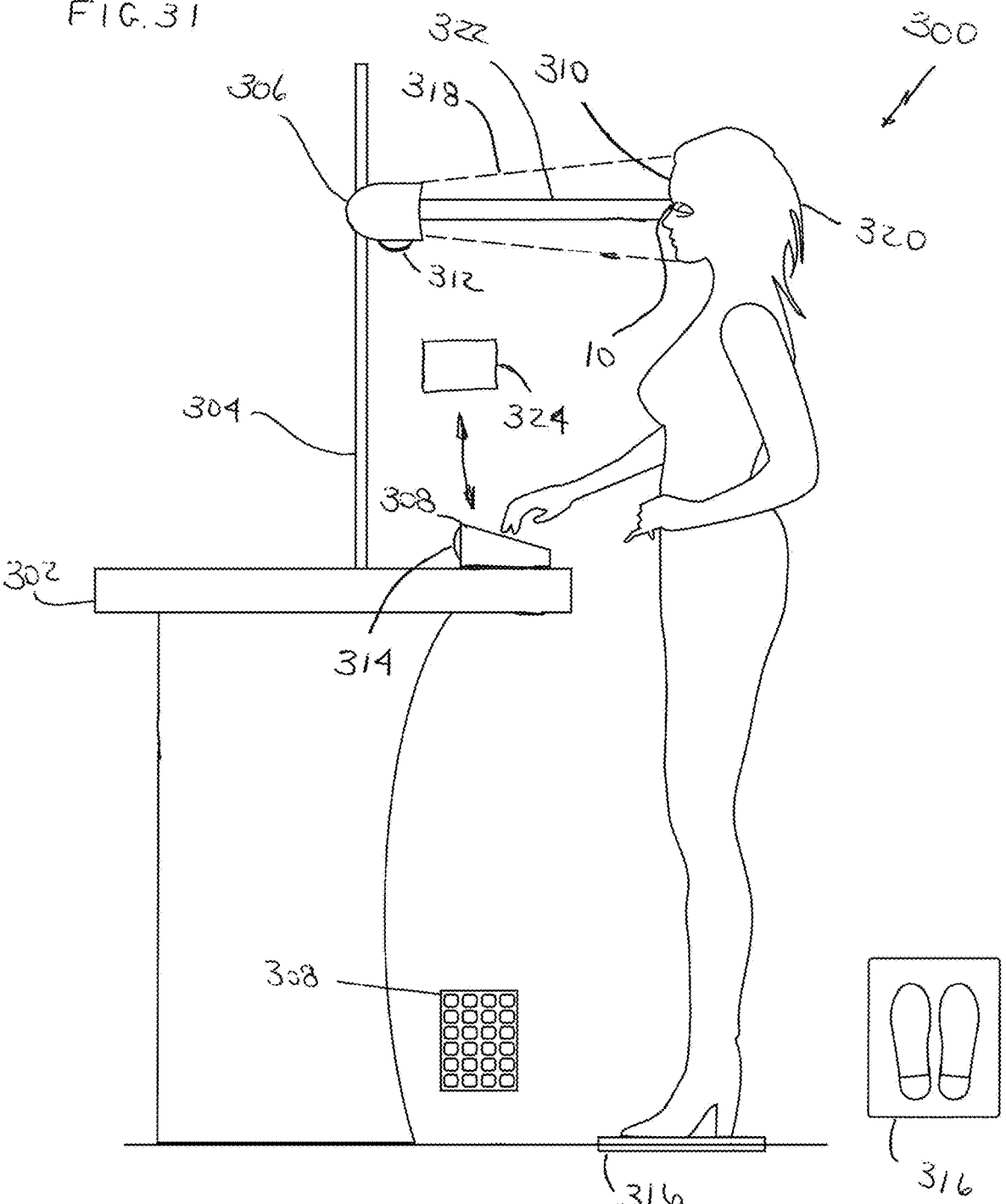
FIG. 31 shows a view of a system configured to locate an ABTT terminus and then to measure the temperature of the ABTT terminus, in accordance with an exemplary embodiment of the present disclosure.
Figure 32:
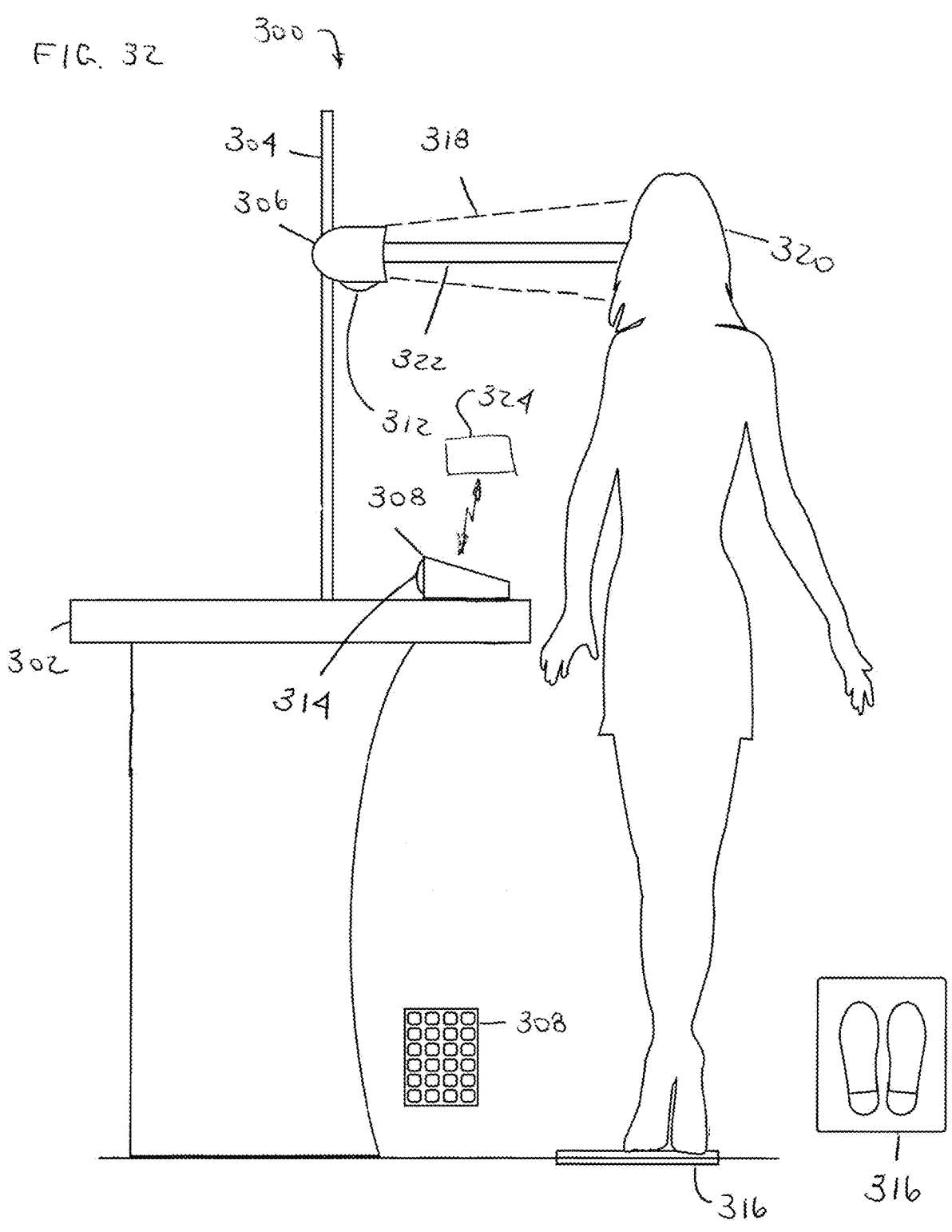
FIG. 32 shows another view of the system of FIG. 31.
Figure 33:
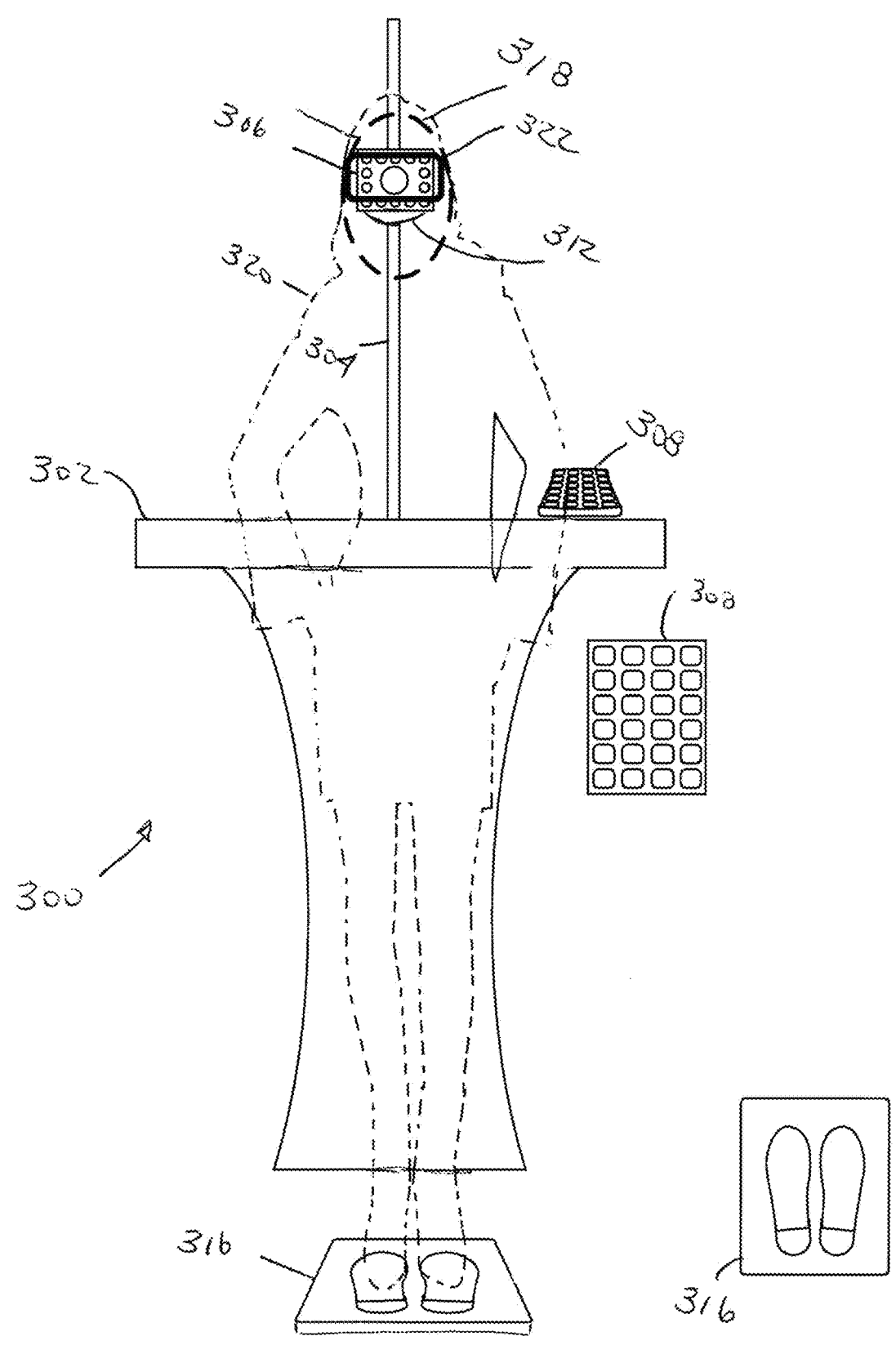
FIG. 33 shows a further view of the system of FIG. 31.

FIGS. 31-33 show a system configured to locate ABTT terminus 10 and then to measure the temperature of ABTT terminus 10, in accordance with an exemplary embodiment of the present disclosure, indicated generally at 300. System 300 is configured to include a desk, table, or platform 302 that is further configured to support element of system 300. System 300 is further configured to include a support system 304 configured to support a movable IR camera 306. Support system 304 is configured to allow camera 306 to be movable or adjustable to a plurality of vertical positions to be able to locate at least one ABTT terminus 10. In an exemplary embodiment, camera 306 is moved manually. In another exemplary embodiment, camera 306 is moved by way of a controller, described in more detail herein. In a further exemplary embodiment, camera 306 is automatically moveable to locate a face and at least one ABTT terminus 10.

System 300 is further configured to include a control device 308 that can be configured to include a keypad, microphone, USB or other port, card scanner, or other device to provide various control functions for system 300. Such control functions can include movement of IR camera 306 along support system 304 to align IR camera 306 with a face 310. IR camera 306 can be configured to include a connector (not shown), a transceiver 312, or both. Similarly, control device 308 can be configured to include a connector (not shown), a transceiver 314, or both. Thus, control device 308 can communicate with IR camera 306 by way of a cable (not shown) or by way of transceivers 312 and 314. System 300 can further be configured to include a pressure or presence detection device 316 that includes a pressure or presence sensor and is configured to communicate with control device 308 either through a cable (not shown) or wirelessly.

It should be understood that IR camera 306 includes a FOV 318 of a certain angle. In an exemplary embodiment, the configuration and position of IR camera 306 is such that FOV 318 is sufficiently large to include most or all of a subject or patient's face 310 when a subject 320 is standing at a location of pressure or presence detection device 316. It should be understood that within FOV 318 is a smaller two-dimensional area 322 that corresponds to the area of ABTT terminus 10 and an area directly adjacent or next to ABTT terminus 10.

To operate system 300, subject 320 stands on pressure or presence detection device 316, which initiates or actuates system 300. Pressure or presence detection device 316 can immediately provide the weight of subject 320. In an exemplary embodiment, subject 320 can begin a temperature measurement operation by pressing a key on control device 308. Alternatively, the presence of subject 320 on pressure detection device 316 can initiate a temperature measurement operation. As yet another alternative, a separate electronic device 324, such as a cell phone, laptop, tablet, etc., can be configured to communicate with system 300 and to initiate system 300 operation as well as control the functions of system 300.

In an exemplary embodiment, subject 320 either manually moves IR camera 306 to be at an eye level, or uses controls on control device 308 to position IR camera 306 vertically along support system 304. In another exemplary embodiment, IR camera 306 moves along support system 304, scanning for a hot spot represented by ABTT terminus 10. In this latter embodiment, once IR camera 306 identifies the hot spot represented by ABTT terminus 10, IR camera 306 positions itself to acquire temperature signals from ABTT terminus 10. It should be noted that the movement of IR camera 306 also provides system 300 with the ability to measure the height of subject 320, since IR camera 306 can determine the location of the top of a head of subject 320 through its thermal imaging capability. Alternatively, once IR camera 306 has located ABTT terminus 10, system 300 can estimate the height of subject 320 given that the average distance from ABTT terminus 10 to the top of a typical person's head is a previously measured distance.

Once IR camera 306 is positioned to measure the temperature of ABTT terminus 10, acquisition and analysis of temperature data begins, which may be accomplished in control device 308 or in separate electronic device 324. The data acquisition process can be configured to include a plurality of time intervals, depending on the type of data analysis required. For simple temperature measurements, the length of data acquisition is typically seconds, e.g., 10 to 20 seconds. For complex measurements, the length of data acquisition can be minutes. Some data acquisition intervals may be very lengthy and it can be beneficial to provide a chair for subject 320.

Figure 33A:
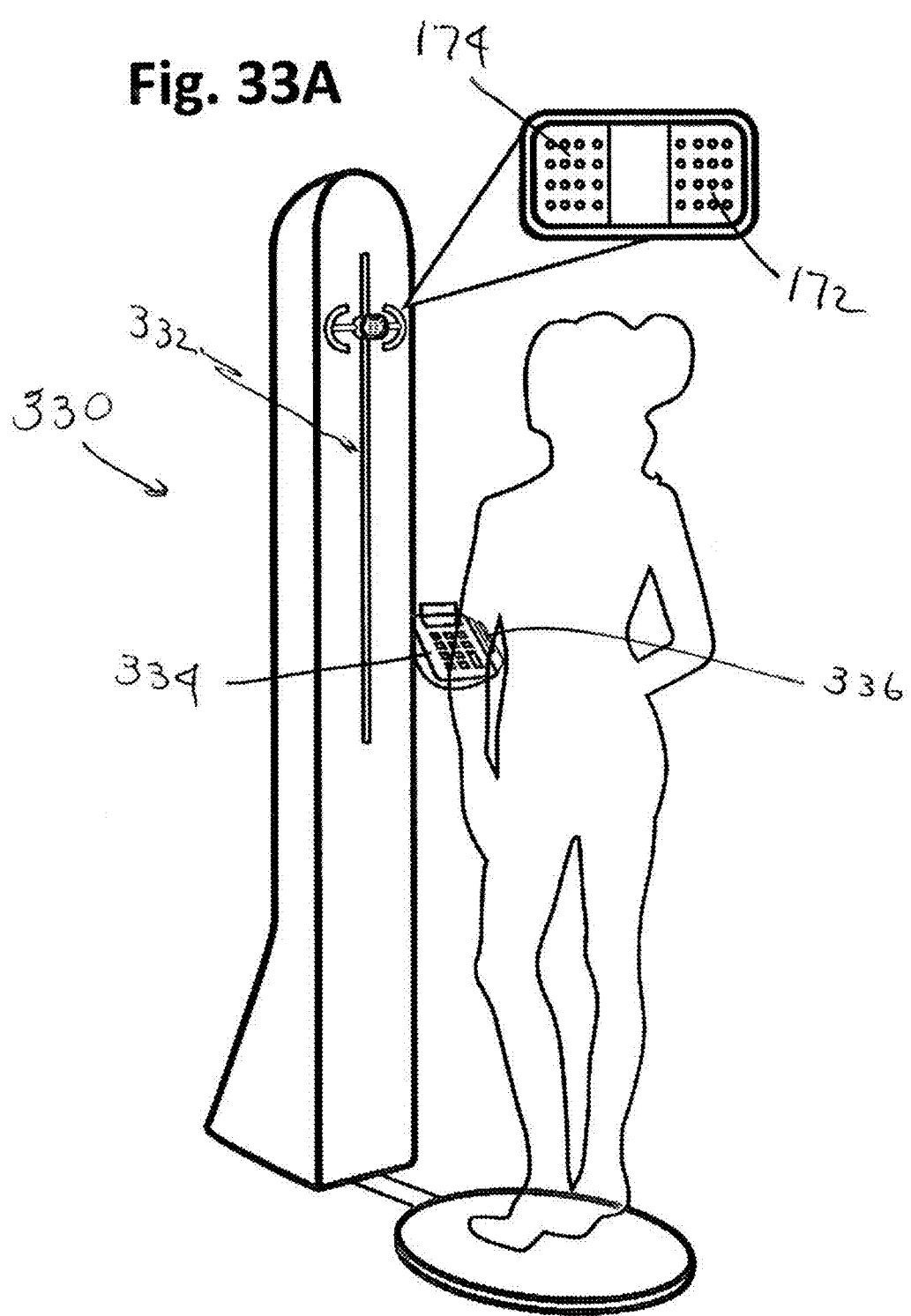
FIG. 33A shows a view of another system configured to locate an ABTT terminus and then to measure the temperature of the ABTT terminus, in accordance with an exemplary embodiment of the present disclosure.
Figure 38:
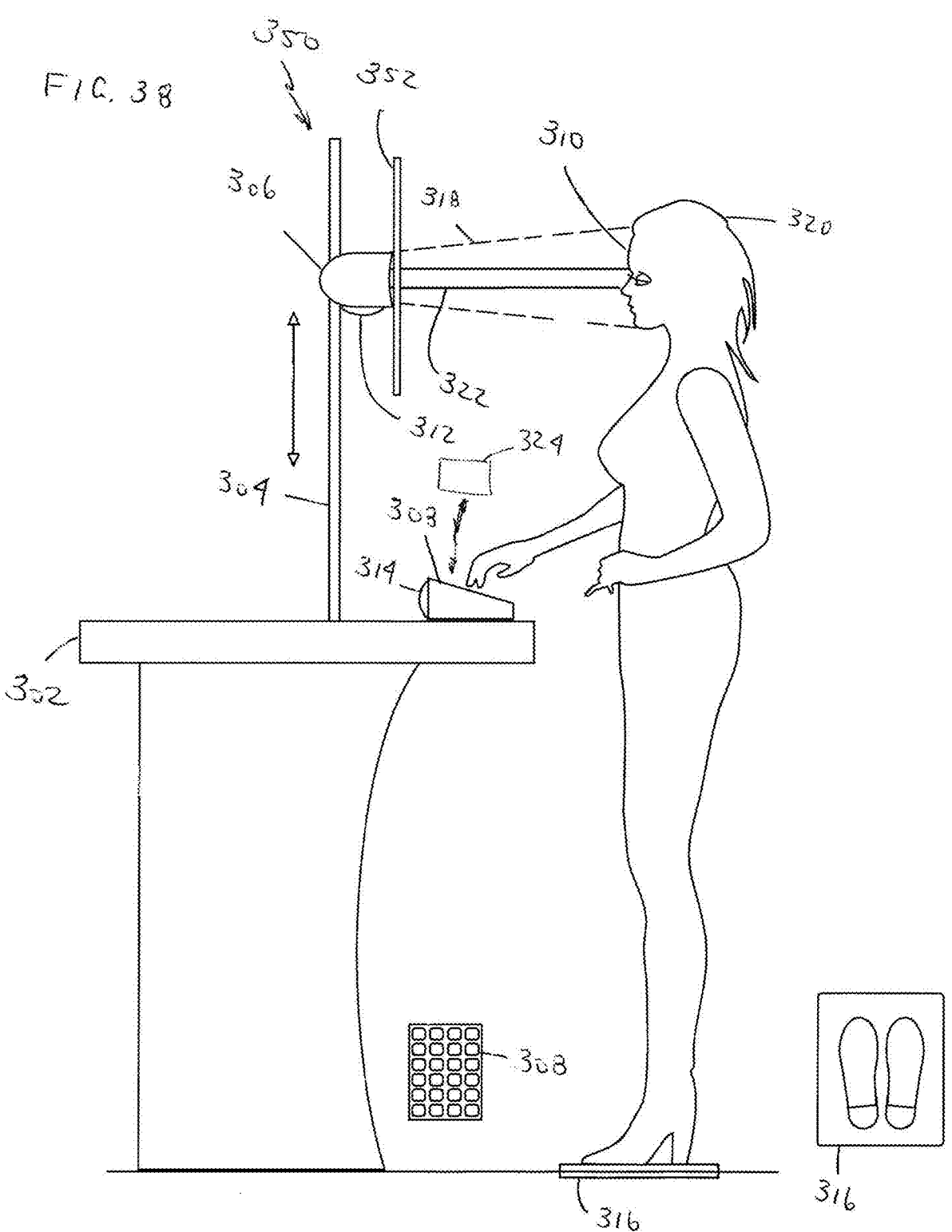
FIG. 38 shows a view of another system configured to locate an ABTT terminus and then to measure the temperature of the ABTT terminus, in accordance with an exemplary embodiment of the present disclosure.
Figure 39:
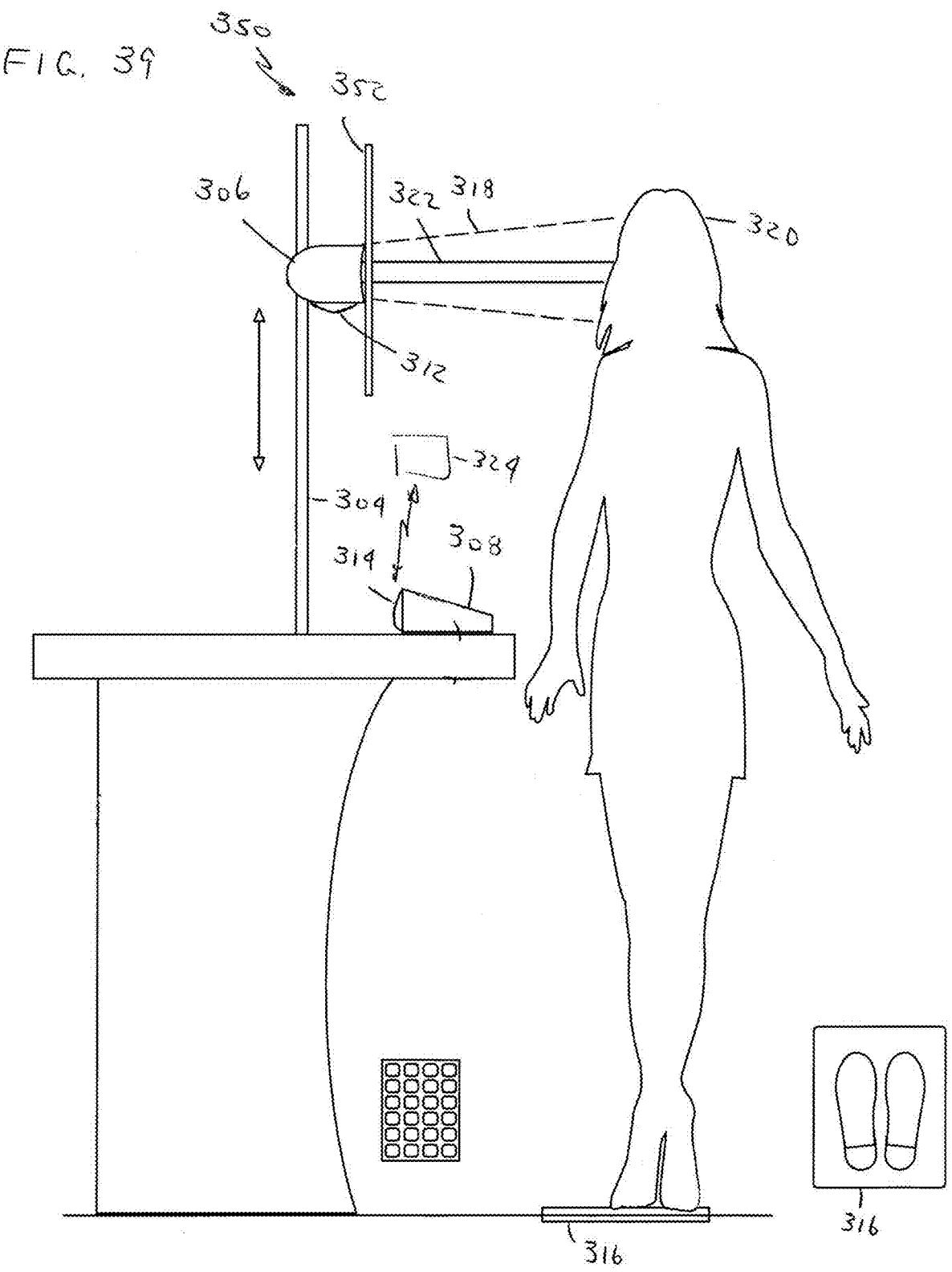
FIG. 39 shows another view of the system of FIG. 38.
Figure 43:
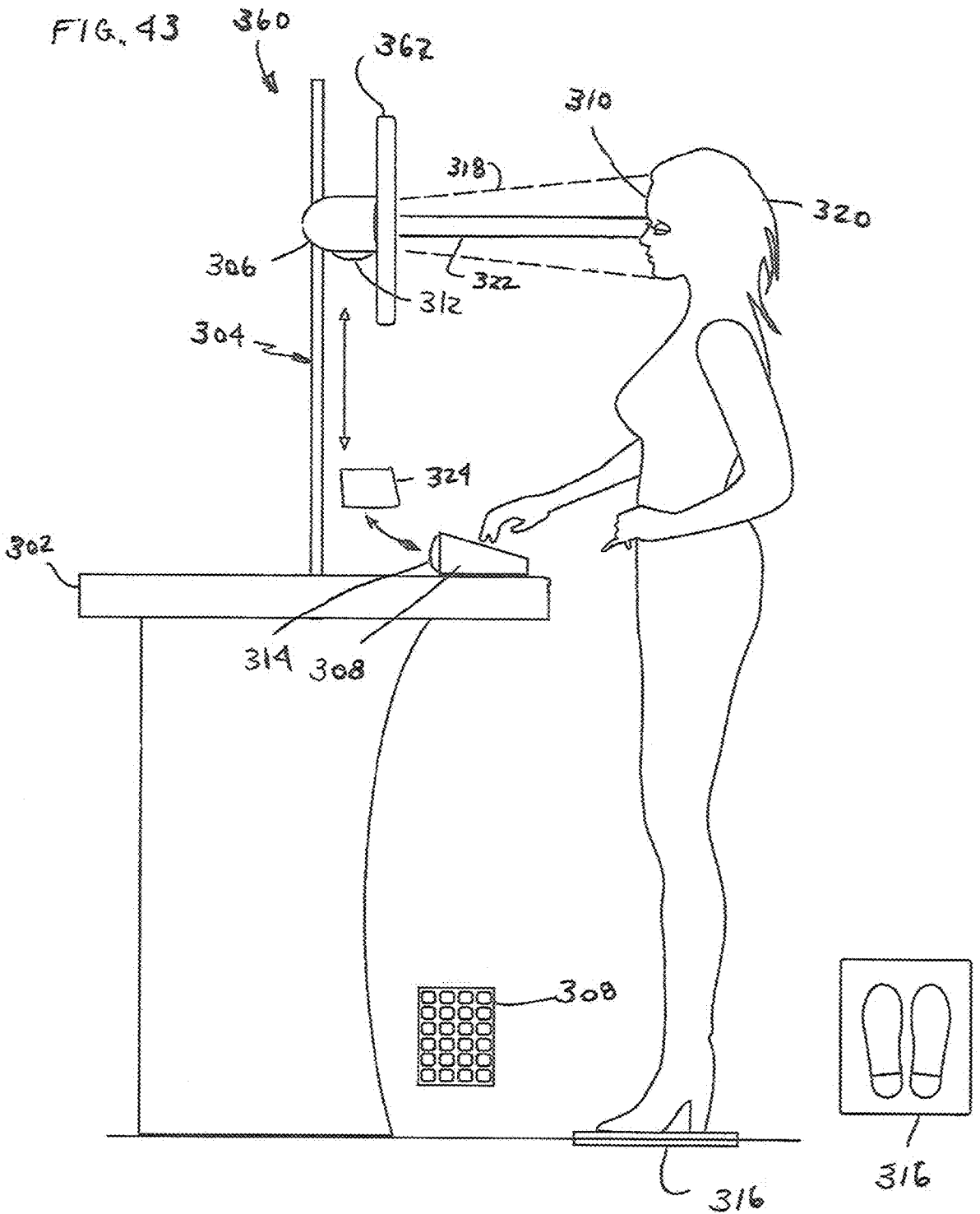
FIG. 43 shows a view of a further system configured to locate an ABTT terminus and then to measure the temperature of the ABTT terminus, in accordance with an exemplary embodiment of the present disclosure.
Figure 44:
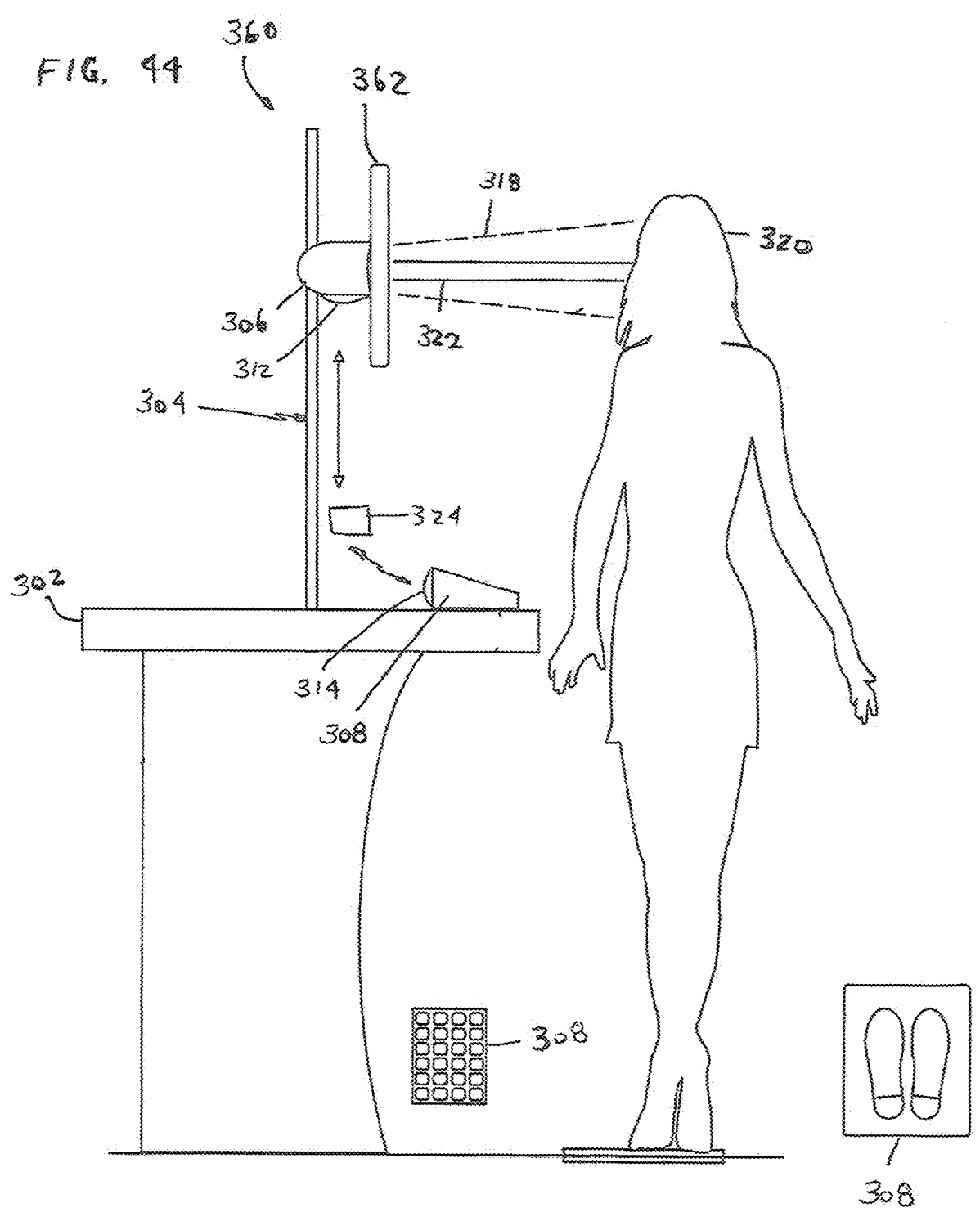
FIG. 44 shows another view of the system of FIG. 43.
Figure 45:
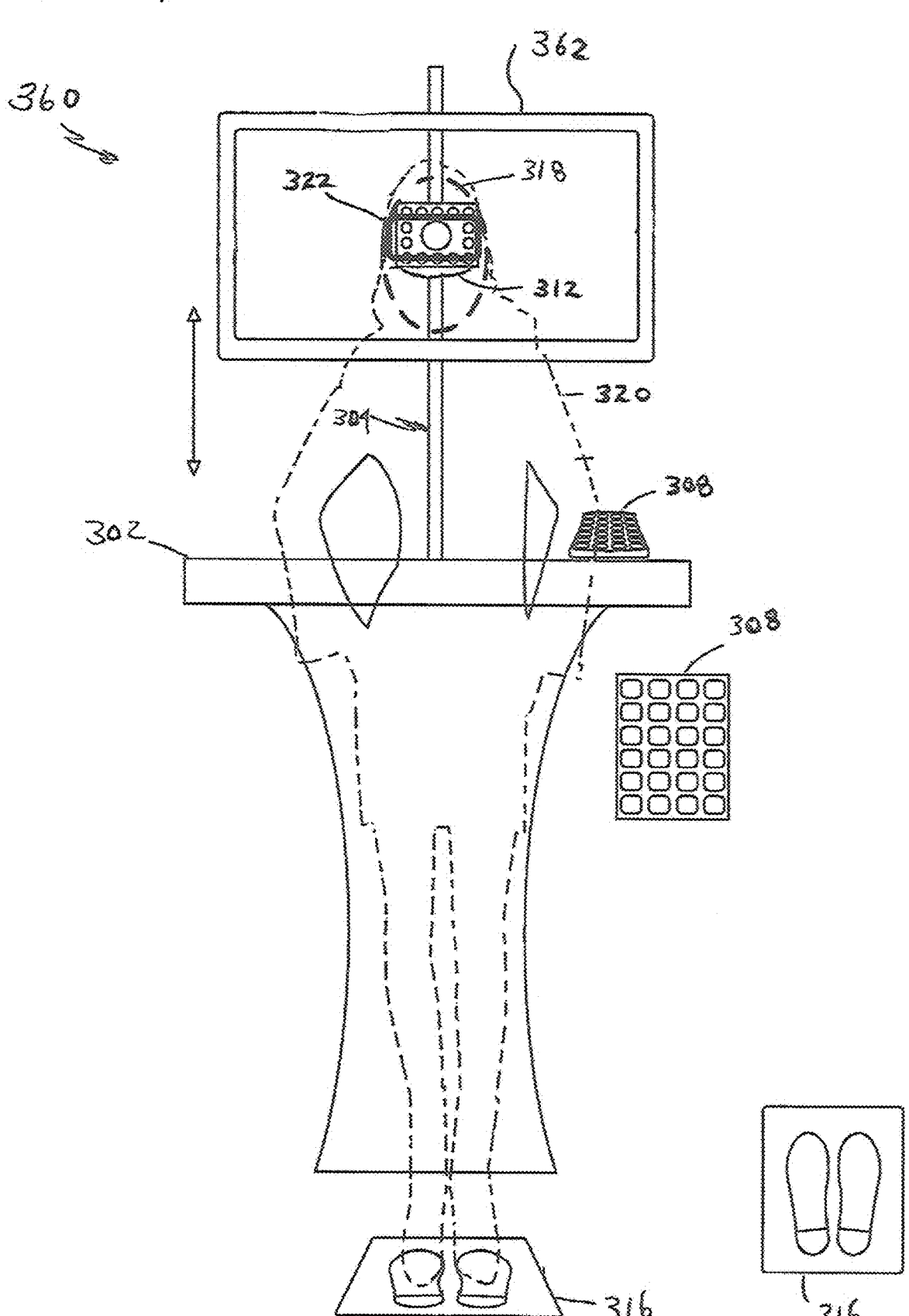
FIG. 45 shows a further view of the system of FIG. 43.
Figure 49:
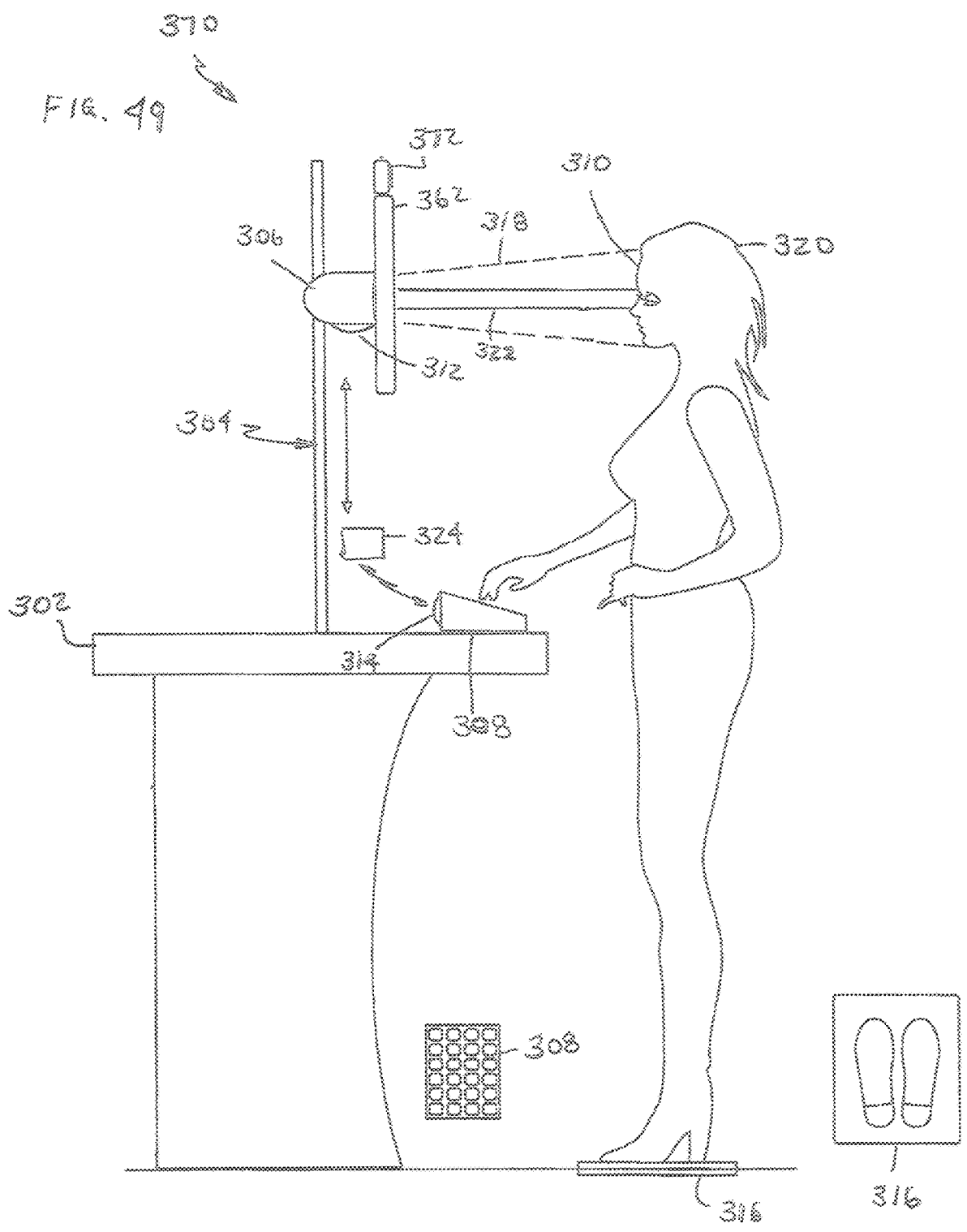
FIG. 49 shows a view of an even further system configured to locate an ABTT terminus and then to measure the temperature of the ABTT terminus, in accordance with an exemplary embodiment of the present disclosure.
Figure 57:
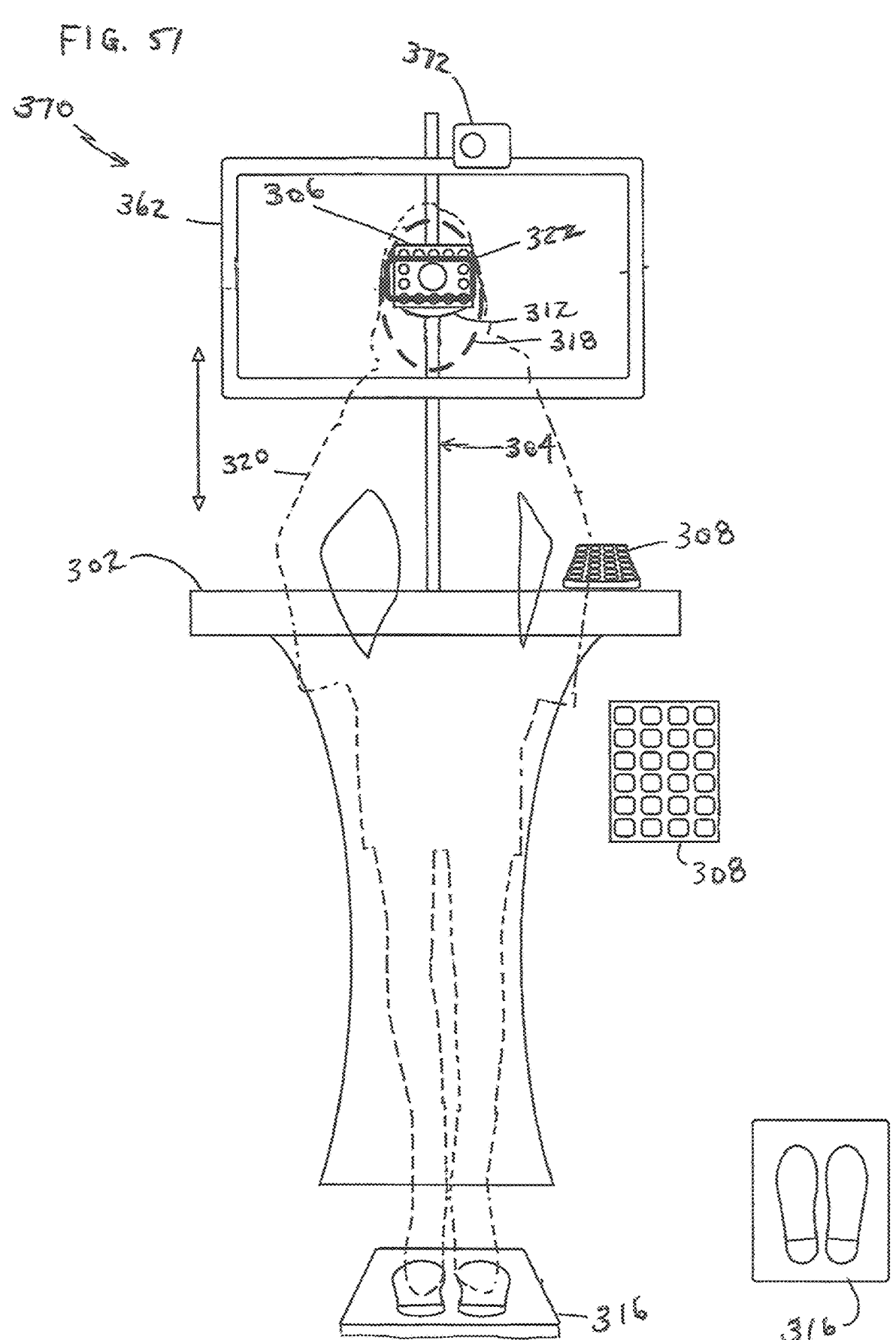
FIG. 57 shows another view of the system of FIG. 56.
Figure 56:
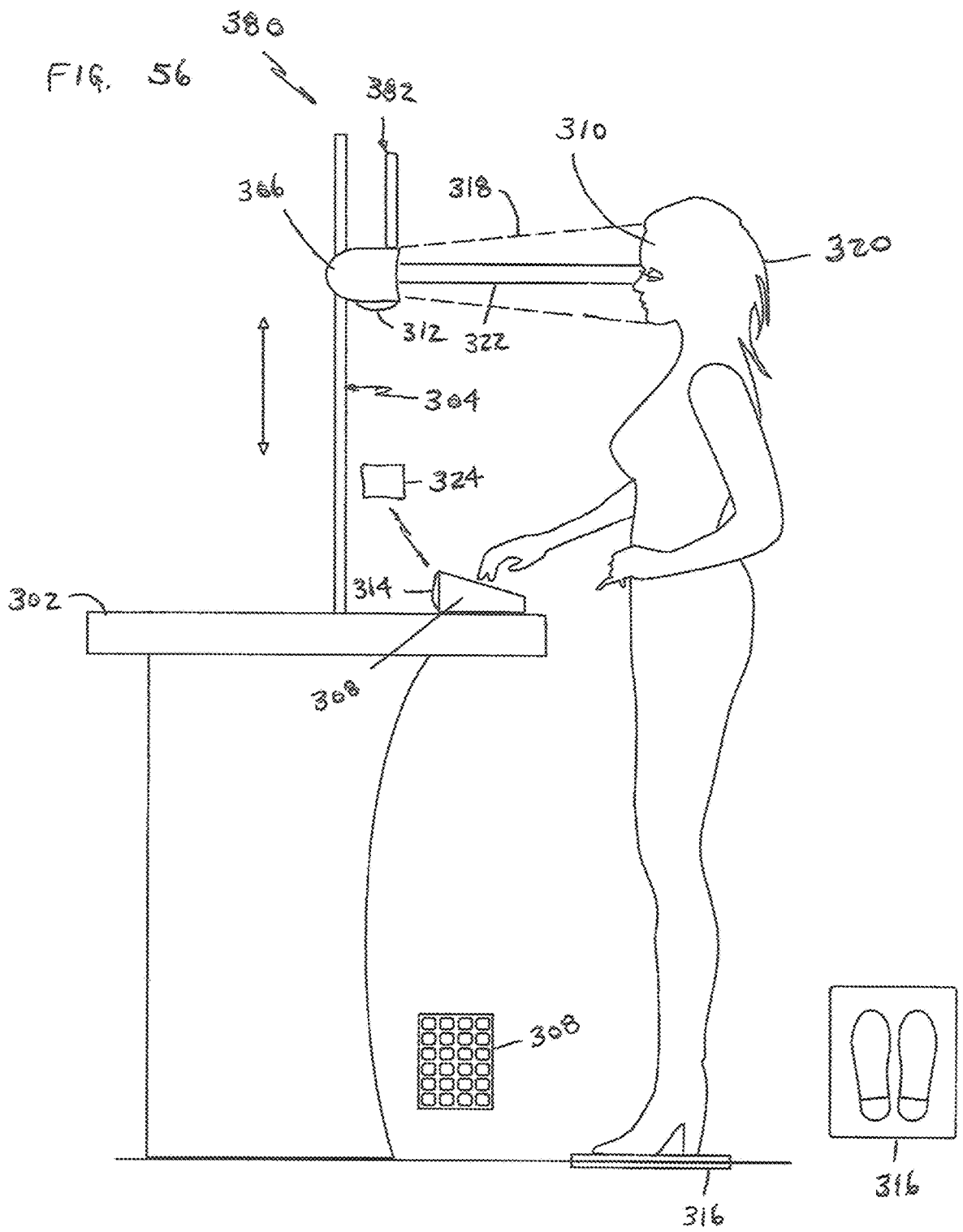
FIG. 56 shows a view of a still further system configured to locate an ABTT terminus and then to measure the temperature of the ABTT terminus, in accordance with an exemplary embodiment of the present disclosure.
Figure 57:
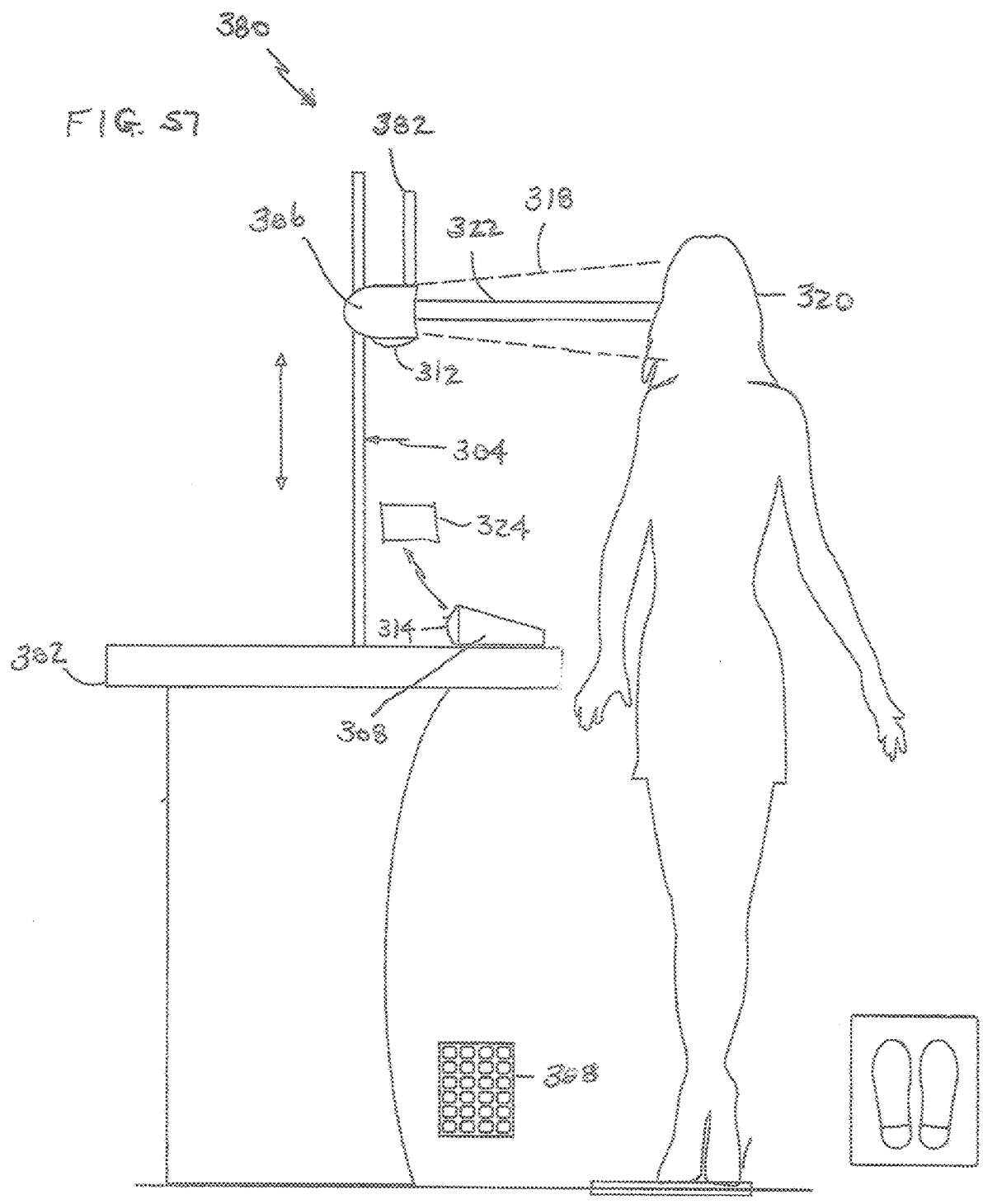
Figure 58:
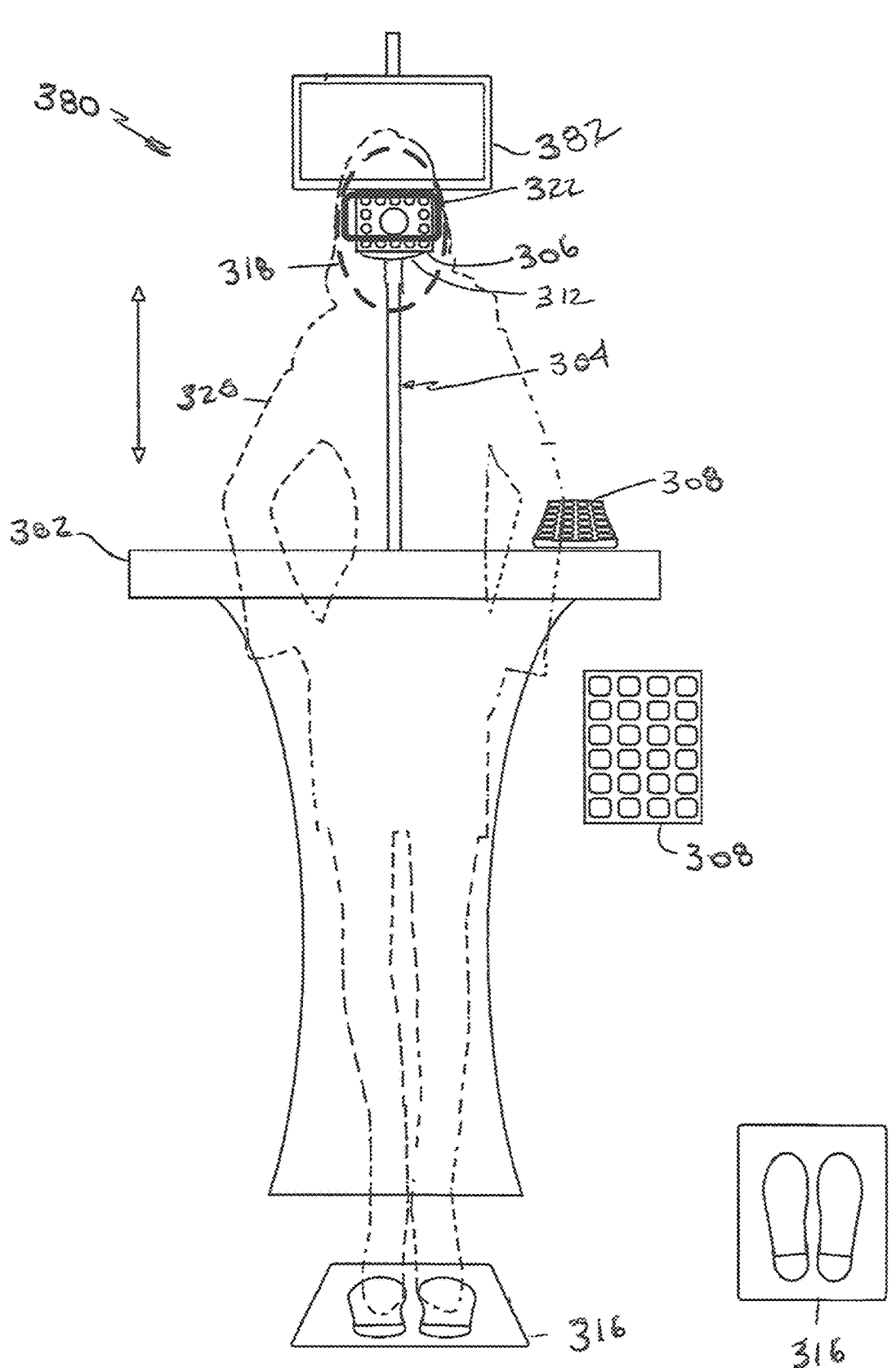
FIG. 58 shows a further view of the system of FIG. 56.
Figure 63:
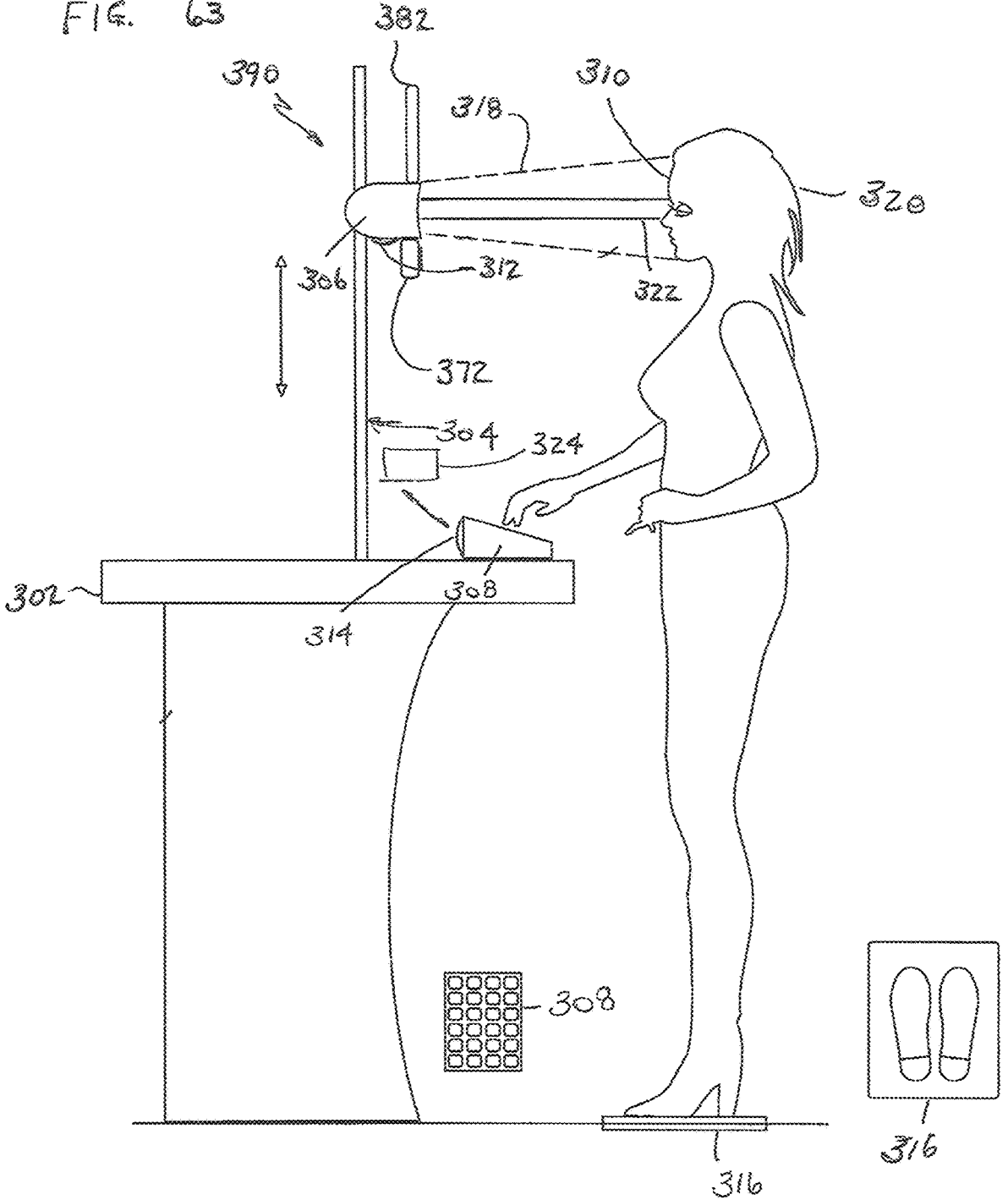
FIG. 63 shows a view of yet an even further system configured to locate an ABTT terminus and then to measure the temperature of the ABTT terminus, in accordance with an exemplary embodiment of the present disclosure.
Figure 64:
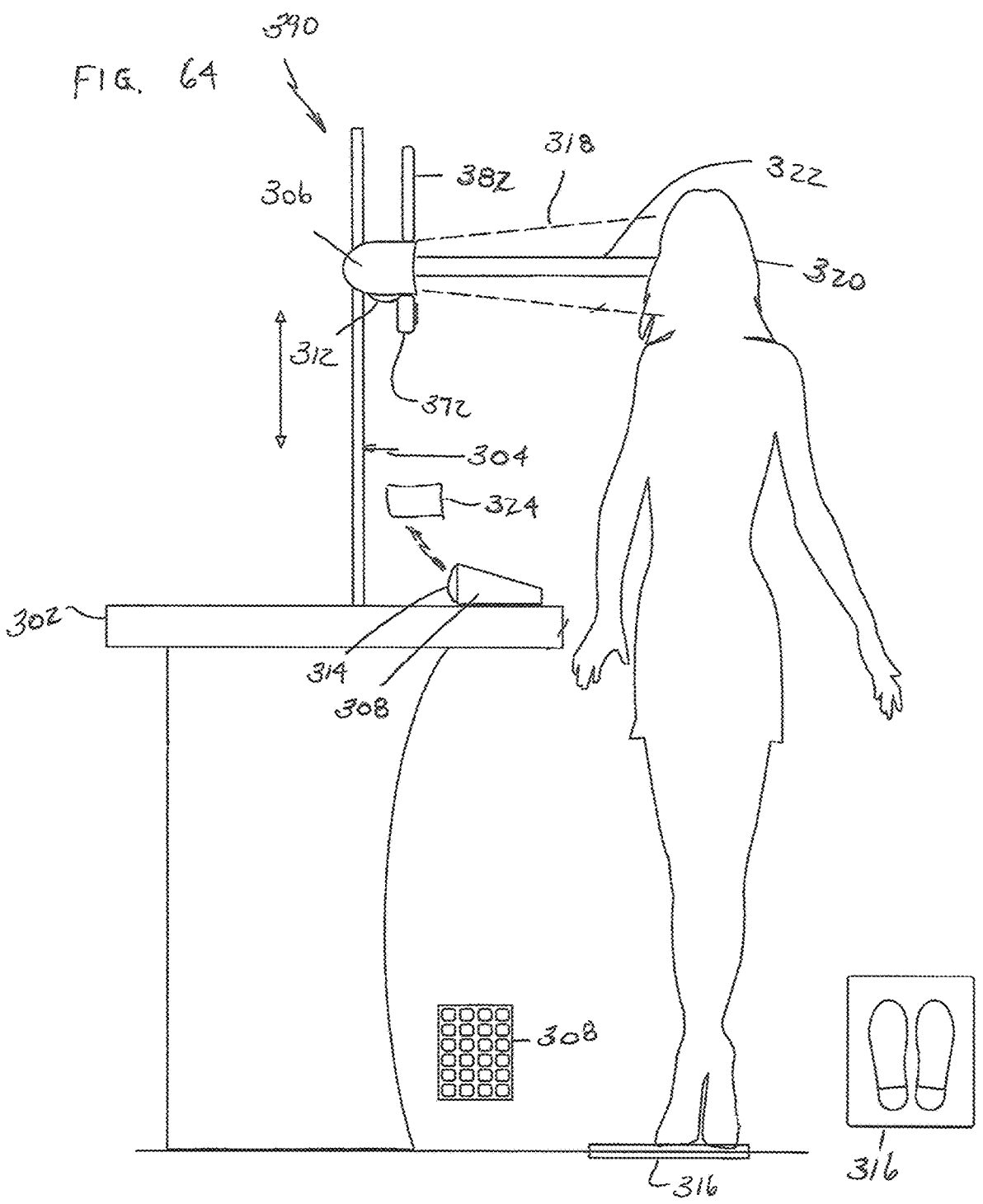
FIG. 64 shows another view of the system of FIG. 63.
Figure 65:
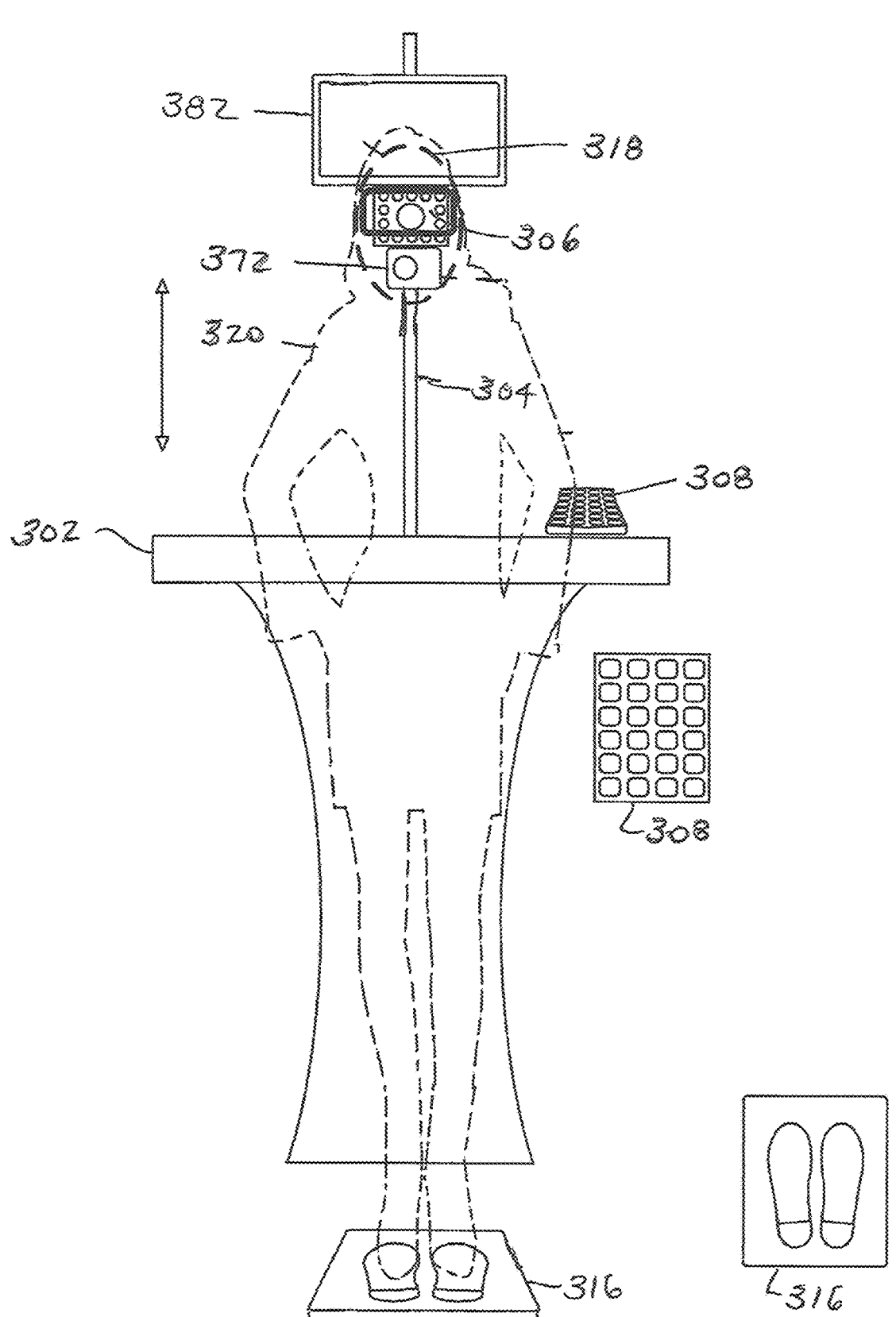
FIG. 65 shows a further view of the system of FIG. 63.

FIGS. 33A and 33B show views of another system, indicated generally at 330, configured to locate ABTT terminus 10 and then to measure the temperature of ABTT terminus 10, in accordance with an exemplary embodiment of the present disclosure. ABTT temperature measurement system includes right sensor array 172, left sensor array 174, a sliding mechanism 332 to change the position of right sensor array 172 and left sensor array 174, and a combination keypad and card reader 334 having a card slot 336. In this embodiment there is no display, such as might be used for advertisements, and measurement is done by inserting an ID card in card slot 336 or inserting a credit card in card slot 336 for payment. As shown in FIG. 33B, keypad and card reader 334 includes a second slot 338 for connecting with electronic device 184 being operatively coupled with system 330 during measurement, in which electronic device 184, for example a cell phone, when placed in electronic device slot 338 provides height information to system 330 allowing thereby automatic height adjustment by sliding mechanism 332. Keypad and card reader 334 can include a reader for a credit card in the event a user is purchasing measurement, an identification card, and the like.

Support system 304 can be configured in a variety of arrangements. FIGS. 34 and 35 show an exemplary support system 304a that includes an "H" configuration, including two vertically extending poles 326 and a cross bar 328. IR camera 306 is configured to move left and right along cross bar 328, and cross bar 328 is configured to move vertically along poles 326, with both movements permitting movement of IR camera 306 to align with a subject or patient's face. FIGS. 36 and 37 show another exemplary support system 304b that includes a single pole 326 configured to permit movement of IR camera 306 vertically along pole 326. To achieve left-right or horizontal positioning, a patient or subject would move left or right.

FIGS. 38-42 show another ABTT temperature measurement system in accordance with an exemplary embodiment of the present disclosure, indicated generally at 350. System 350 is similar to system 300 in many respects, but system 350 further includes a mirror 352.

FIGS. 43-48 show another ABTT temperature measurement system in accordance with an exemplary embodiment of the present disclosure, indicated generally at 360. System 360 is similar to systems 300 and 350 in many respects, but system 360 further includes a display 362 configured to present the output of IR camera 306 to subject 320. Display 362 is transparent to IR energy, so camera 306 receives IR energy transmitted through display 362.

FIGS. 49-55 show another ABTT temperature measurement system in accordance with an exemplary embodiment of the present disclosure, indicated generally at 370. System 370 is similar to system 360 in many respects, but system 370 further includes a digital camera 372 configured to capture an image of face 310 at visible optical wavelengths and to present face 310 on display 362 to aid in aligning IR camera 306.

FIGS. 56-62 show another ABTT temperature measurement system in accordance with an exemplary embodiment of the present disclosure, indicated generally at 380. System 380 is similar to systems 360 and 370 in many respects, but system 380 further includes a display device 382 positioned adjacent to IR camera 306. Display device 382 can be configured to include a digital camera, the output of which is presented on display device 382 to aid in aligning IR camera 306 with respect to face 310.

FIGS. 63-69 show another ABTT temperature measurement system in accordance with an exemplary embodiment of the present disclosure, indicated generally at 390. System 390 includes selective features from systems 370 and 380. Display device 382 is configured to present visual data provided by digital camera 372 to aid in aligning IR camera 306 with respect to face 310.

Figure 70:
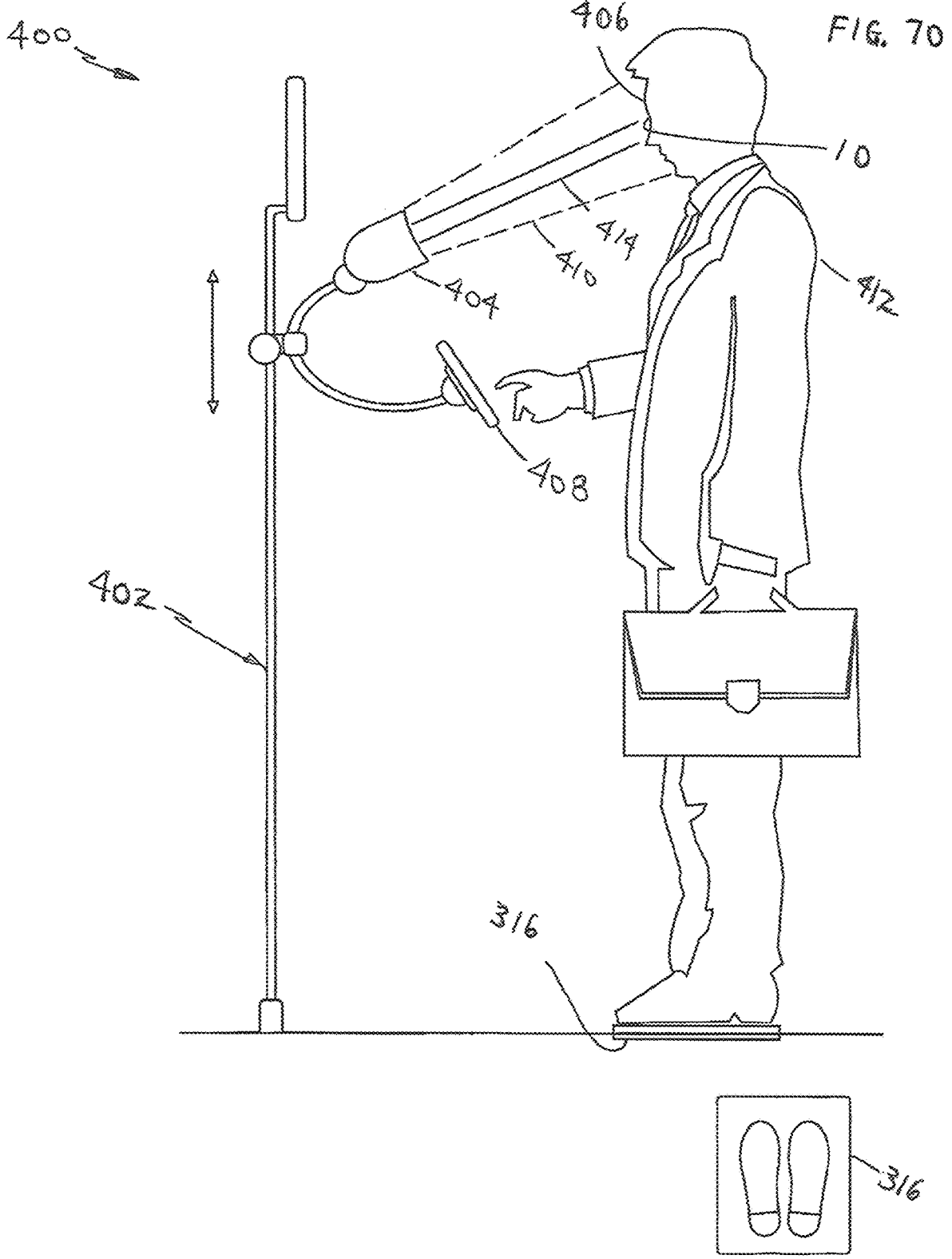
FIG. 70 shows a view of another system configured to locate an ABTT terminus and then to measure the temperature of the ABTT terminus, in accordance with an exemplary embodiment of the present disclosure.

FIG. 70 shows another system configured to locate ABTT terminus 10 and then to measure the temperature of ABTT terminus 10, in accordance with an exemplary embodiment of the present disclosure, indicated generally at 400. System 400 is configured to include a support system 402 configured to support a movable IR camera 404. Support system 402 is configured to allow IR camera 404 to be movable or adjustable to a plurality of vertical positions to be able to locate at least one ABTT terminus 10. In an exemplary embodiment, camera 404 is moved manually. In another exemplary embodiment, camera 404 is moved by way of a controller. In a further exemplary embodiment, camera 404 is automatically moveable to locate a face 406 and at least one ABTT terminus 10.

Figure 70B:
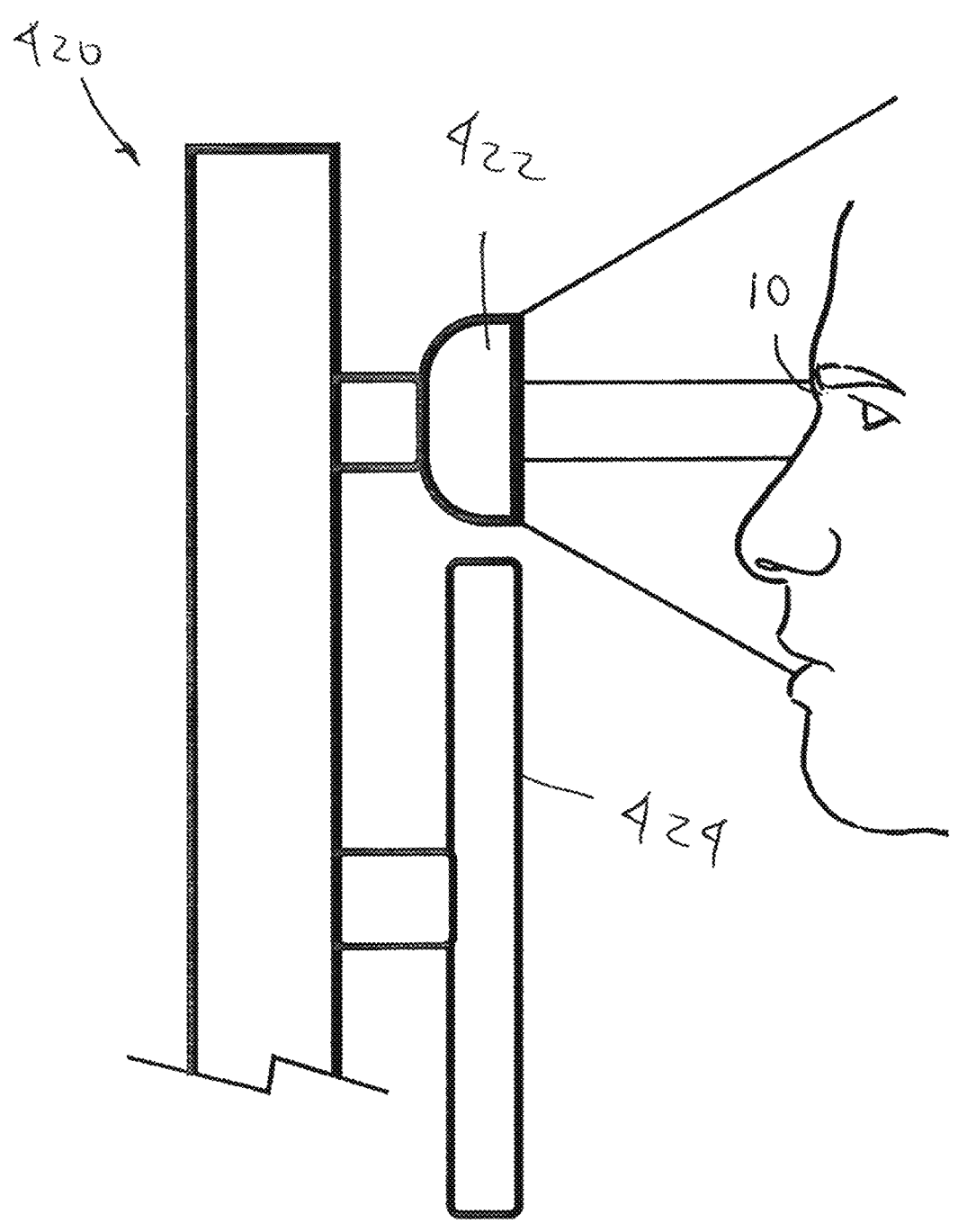
FIG. 70B shows a view of a portion of the system of FIG. 70A.

FIGS. 70A and 70B show views of yet another system, indicated generally at 420, configured to locate ABTT terminus 10 and then to measure the temperature of the ABTT terminus 10, in accordance with an exemplary embodiment of the present disclosure. System 420 includes an infrared sensor array 422, which may include a thermopile array, positioned above a display 424 and being operatively coupled with display 424. Display 424 can be configured to display an advertisement during measurement of emissions from ABTT terminus 10, and measurement results can be configured to appear on display 424 at random times during the advertisement. FIG. 70B shows view of a portion of system 420 during measurement of a subject, with sensor array 422 capturing thermal signals from ABTT terminus 10 of the subject.

FIGS. 70C and 70D show views of still yet another system, indicated generally at 430, configured to locate ABTT terminus 10 and then to measure the temperature of ABTT terminus 10, in accordance with an exemplary embodiment of the present disclosure. ABTT temperature measurement system 430 includes thermal sensors 432 positioned behind a screen 434, thermal sensors 432 include at least one of infrared sensors and a thermal imaging device, and screen 434 being preferably an LED display to facilitate calculating thermal energy generated by screen 434, since LED's have a rather stable temperature, and the temperature of LED screen 434 can be used to adjust or correct the temperature measured by sensors 432 to determine the temperature of ABTT terminus 10. Screen 434 can also be transparent to IR energy, so infrared sensors 432 receive IR energy transmitted through screen 434. System 430 is configured to measure thermal signals from ABTT terminus 10 while an image 436, such as an advertisement, is being shown on screen 434, and the subject must look at screen 434 to be measured. In addition, the measurement results are shown on screen 434. FIG. 70D shows system 430 during measurement of the subject, with sensor array 432 capturing thermal signals from ABTT terminus 10 of the subject.

FIGS. 70E and 70F show views of an even further system, indicated generally at 450, configured to locate ABTT terminus 10 and then to measure the temperature of ABTT terminus 10, in accordance with an exemplary embodiment of the present disclosure. ABTT temperature measurement system 450 includes a digital camera 452, an infrared sensor array 454, and a screen 456 showing advertisement 458 or other information while measurement of emissions from ABTT terminus 10 is conducted. FIG. 70F shows system 450 during measurement of the subject, with sensor array capturing thermal signal from ABTT of a subject. Digital camera 452 captures an image of ABTT terminus 10 and eyes 32, and uses this image information to align infrared sensor array 454 with ABTT terminus 10. Then the digital image is superimposed on the displayed thermal image.

Figure 70H:
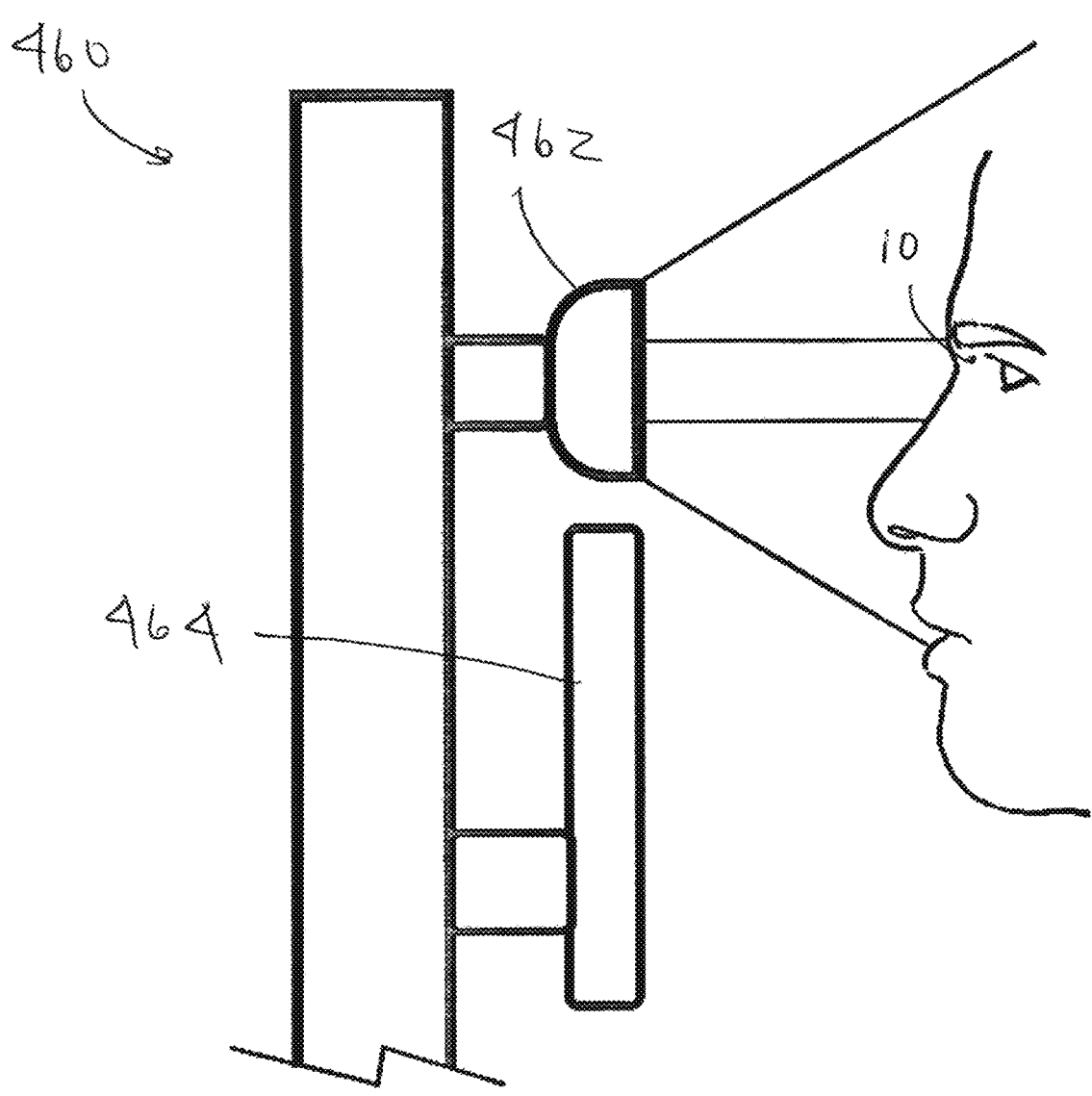
FIG. 70H shows a view of a portion of the system of FIG. 70G.

FIGS. 70G and 70H show views of an even further system, indicated generally at 460, configured to locate ABTT terminus 10 and then to measure the temperature of ABTT terminus 10, in accordance with an exemplary embodiment of the present disclosure. ABTT temperature measurement system 460 includes a thermal image camera 462 and a screen 464 showing advertisement 466 or other information while measurements are is being taken of thermal emissions of ABTT terminus 10. FIG. 70H shows a view of system 460 during measurement of the subject, with sensor array 462 capturing thermal signals from ABTT terminus 10 of the subject.

Figure 70I:
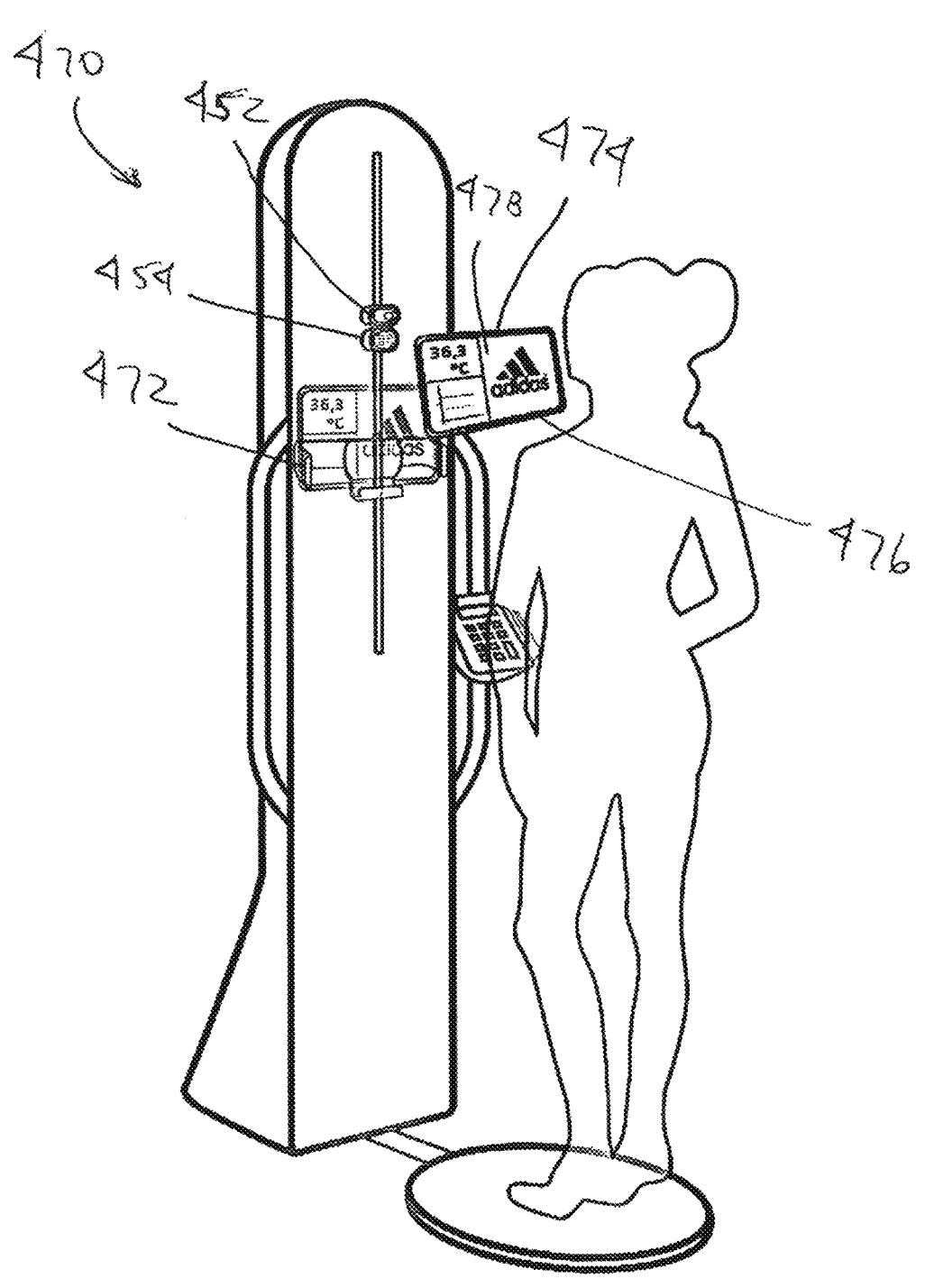
FIG. 70I shows a view of an even further system configured to locate an ABTT terminus and then to measure the temperature of the ABTT terminus, in accordance with an exemplary embodiment of the present disclosure.
Figure 70J:
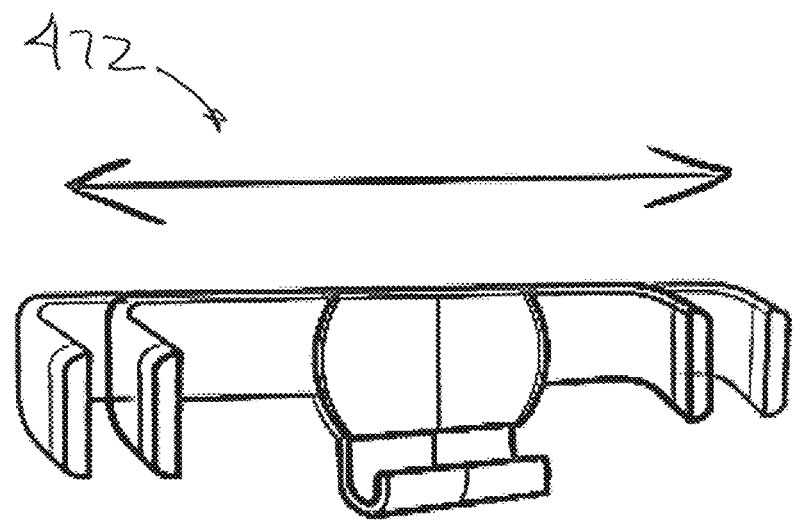
FIG. 70J shows a view of a clamp of FIG. 70I.
Figure 70K:
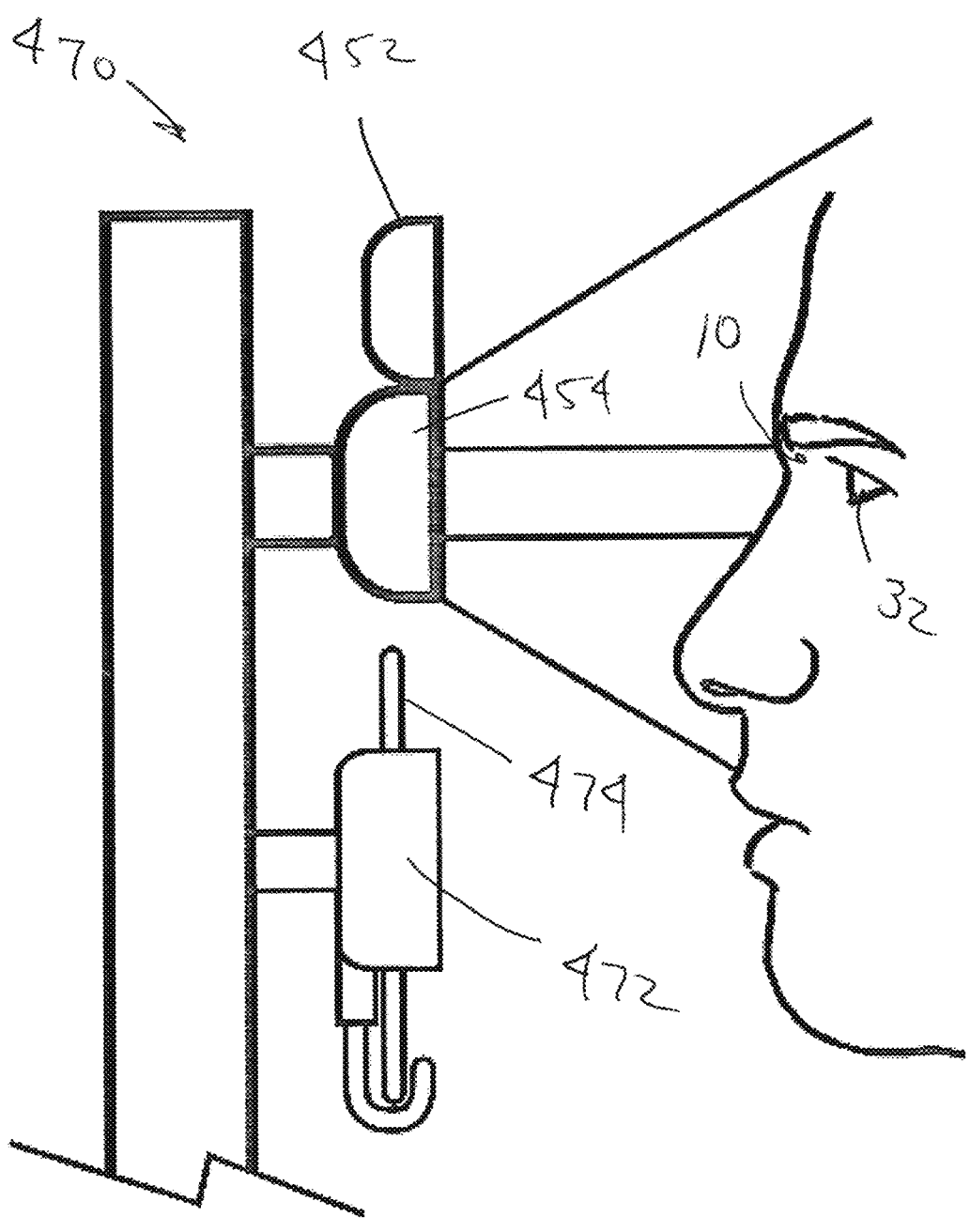
FIG. 70K shows a view of a portion of the system of FIG. 70I.
Figure 70:
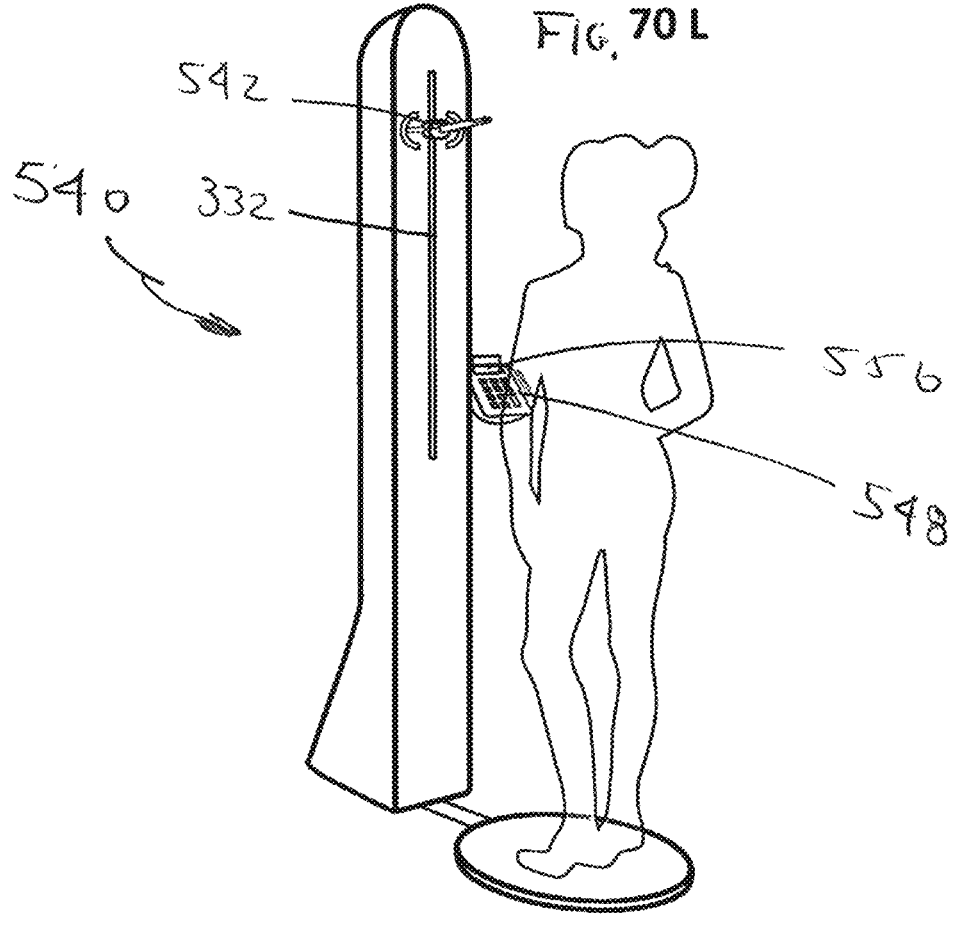
Figure 70:
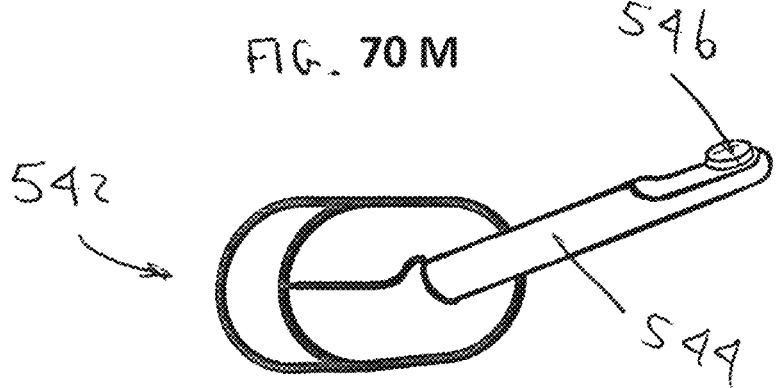
Figure 70:
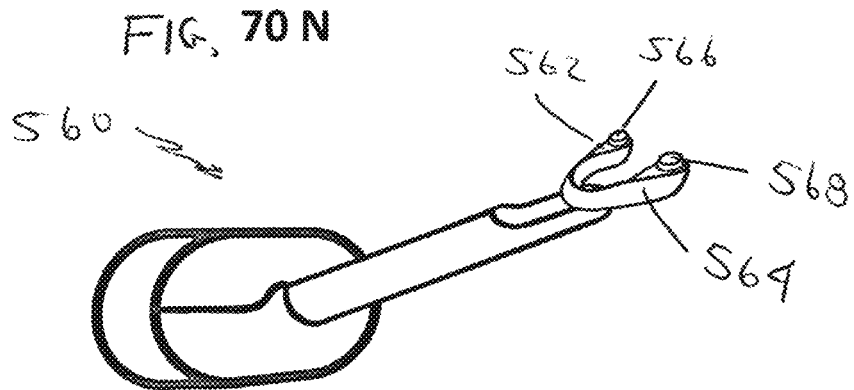
Figure 70:
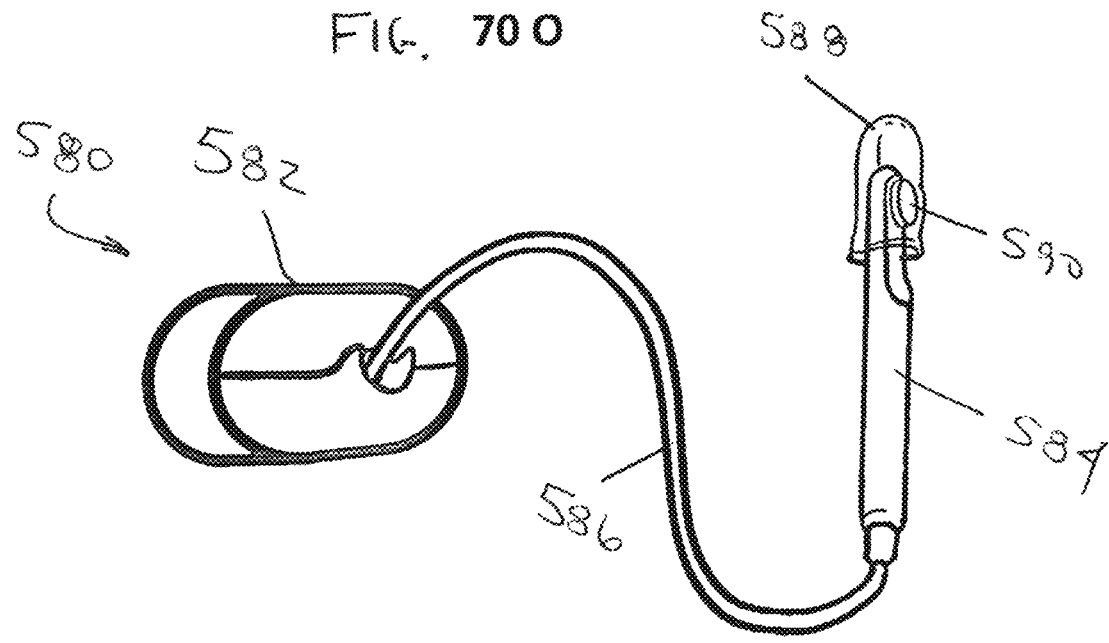
Figure 70:
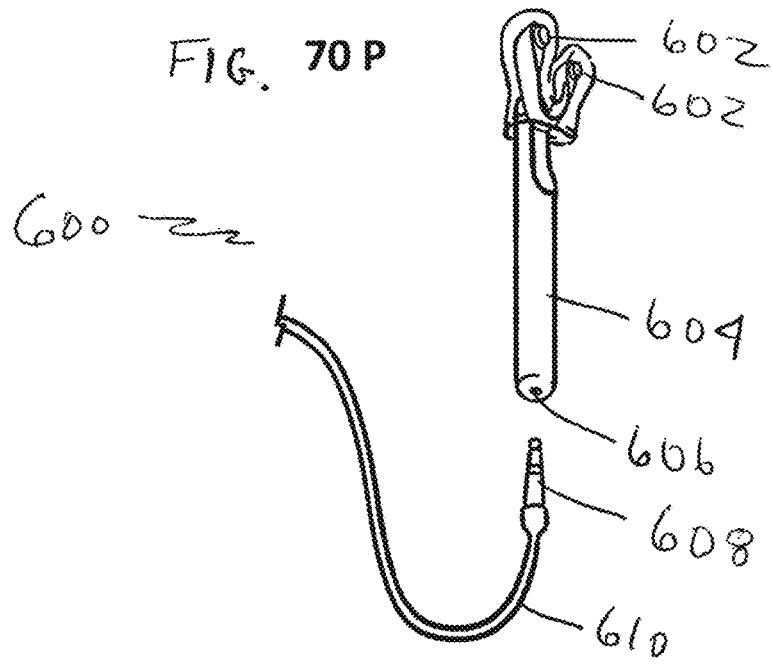
Figure 70:
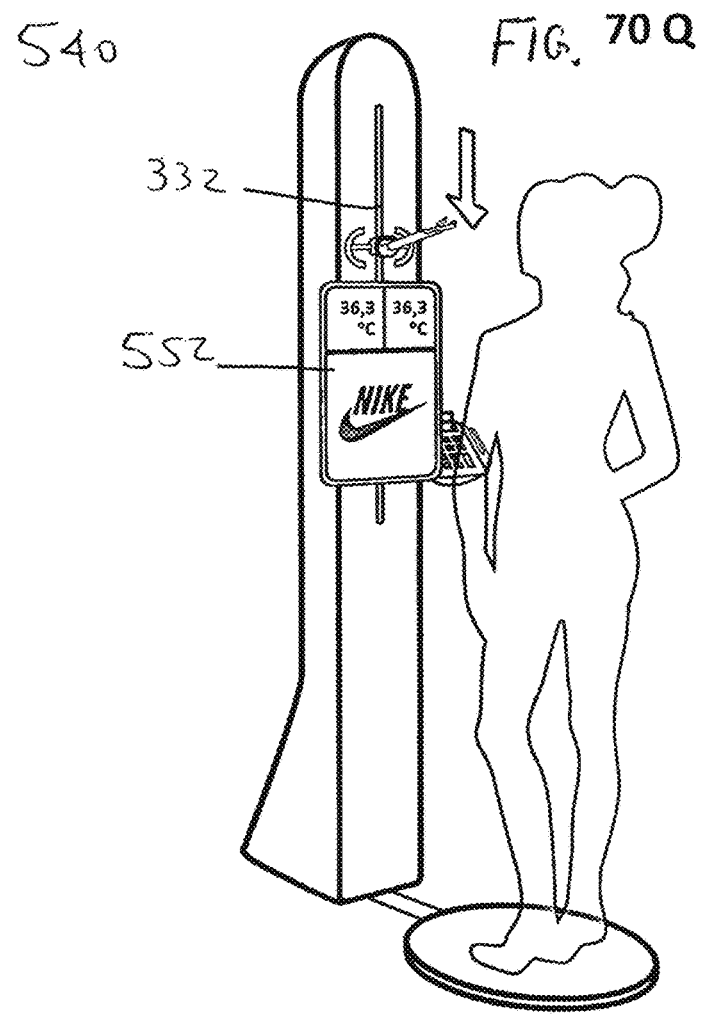

FIGS. 70I-K show views of an even further system, indicated generally at 470, configured to locate ABTT terminus 10 and then to measure the temperature of ABTT terminus 10, in accordance with an exemplary embodiment of the present disclosure. ABTT temperature measurement system 470 includes digital camera 452, infrared sensor array 454, and a clamp mechanism 472 being configured to secure an electronic device 474, electronic device 474 including a display 476 and showing on its display 476 an advertisement 478 or other information while measurement is being taken. FIG. 70J shows details of clamp mechanism 472 for securing electronic device 474, such as a cell phone, tablet, computer, and the like. FIG. 70I shows a view of system 470 during measurement of the subject, with sensor array 454 capturing thermal signals from ABTT terminus 10 of the subject. Digital camera 452 captures an image of ABTT terminus 10 and eyes 32, and uses this image information to align infrared sensor 454 with ABTT terminus 10. The digital image is then superimposed on the thermal image.

FIGS. 70L-70M show views of an even further system, indicated generally at 540, configured to locate ABTT terminus 10 and then to measure the temperature of ABTT terminus 10, in accordance with an exemplary embodiment of the present disclosure. System 540, and other systems of the present disclosure, can alternatively be described as being measuring stations. ABTT temperature measurement system 540 includes sensor device 542, which includes a rod 544 having a contact sensor 546 at its free end, such as a thermistor, a keypad 548, and a display 550 adjacent to keypad 548, display 550 reporting the value measured by sensor device 542. Display 550 is operatively coupled with electronics of sensor device 542, display 550 displaying an advertisement after the measurement is done, and display 550 displaying simultaneously the measurement results. Pen-like sensor device 542 is connected to sliding mechanism 332 of system 540 for alignment of sensor 546 with ABTT terminus 10 of people with different height. In this embodiment, the results are calculated and reported after the measurement is done, and there is no movable display, as it was shown in FIGS. 70A to 70H. The measuring device, illustrated as a pen-like sensor device and a dual sensor device in FIGS. 70L to 70N have been described in co-pending U.S. patent application Ser. No. 15/067,030, filed Mar. 10, 2016, incorporated by reference herein in its entirety. FIG. 70M shows one single sensor device 542, which includes a mechanical connector (not shown) for connecting with sliding mechanism 332 of system 540 and includes a rotating mechanism for alignment of contact sensor 546 with ABTT terminus 10.

FIG. 70N shows a dual sensor device, indicated generally at 560, in accordance with an exemplary embodiment of the present disclosure. Device 560 includes a connector (not shown) for connecting with sliding mechanism 332 of system 540. Device 560 includes a right arm 562 and a left arm 564. Right arm 562 includes a right sensor 566 and left arm 564 includes a left sensor 568.

FIG. 70O shows a sensor device, indicated generally at 580, in accordance with an exemplary embodiment of the present disclosure. Device 580 includes a sensor body 582, and a sensor rod 584 connected to sensor body 582 by a retractable cable or wire 586. Sensor body 582 is configured to mount on and interface with sliding mechanism 332 of system 540. Device 580 further includes sensor 590 positioned on sensor rod 584 at a distal end thereof and a cover 588 to protect sensor 590 to avoid cross-contamination during measurement.

FIG. 70P shows a sensor device, indicated generally at 600, in accordance with an exemplary embodiment of the present disclosure. Device 600 includes dual sensors 602 and a sensor rod 604 on which sensors 602 are positioned. Sensor rod 604 includes a connector 606 for mating with a connector or jack 608 of a retractable cable or wire 610 of, for example, system 540. Sensor device 600 further includes a cover 612 for sensors 602 to avoid cross-contamination during measurement.

FIG. 70Q shows system 540 with the addition of a display 552 connected to sliding mechanism 332, with display 553 the temperature of right ABTT terminus 10 and left ABTT terminus 10.

Clinical experiments by Applicant, who is a medical doctor, showed that measuring right ABTT terminus 10 and left ABTT terminus, preferably simultaneously, provides key clinical information on the risk of several diseases and the diagnosis of several diseases. The measurements can include the absolute number (for instance, 36.6 degrees Celsius on the right and 36.0 Celsius on the left) and differences between the left and right side, or variations of temperature with time. The following graphs, which plot temperature vs. time for right ABTT terminus 10 ("R") and left ABTT terminus 10 ("L"), describe hitherto unrecognized characteristics of diseases and conditions based on analysis of the output of ABTT terminuses 10.

Figure 72:
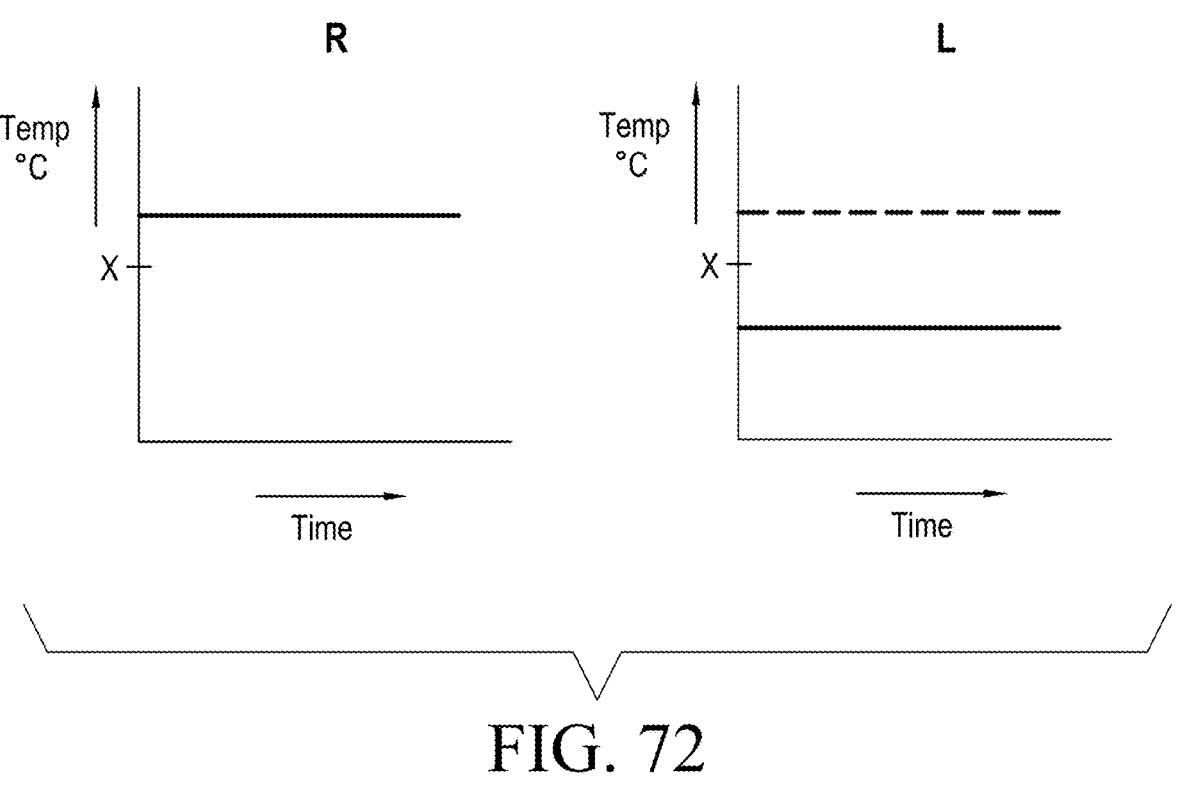
FIG. 72 shows a graph of ABTT temperatures showing a risk of aneurysm.

FIG. 72 shows right ABTT terminus 10 having a higher temperature than left ABTT terminus 10, indicating risk of aneurysm rupture on the right side.

Figure 73:
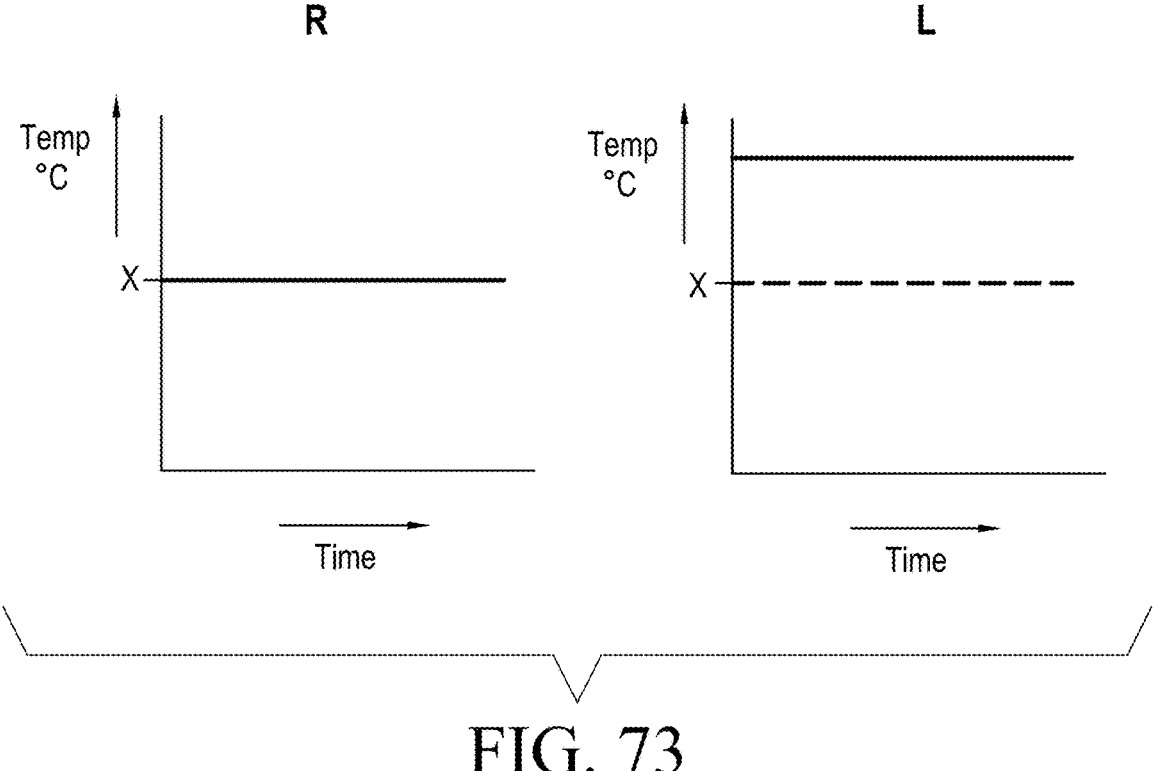
FIG. 73 shows a graph of ABTT temperatures showing a risk of cancer.

FIG. 73 shows normal temperature in right ABTT terminus 10 and higher temperature in left ABTT terminus 10 indicating risk of brain cancer in the left side.

Figure 74:
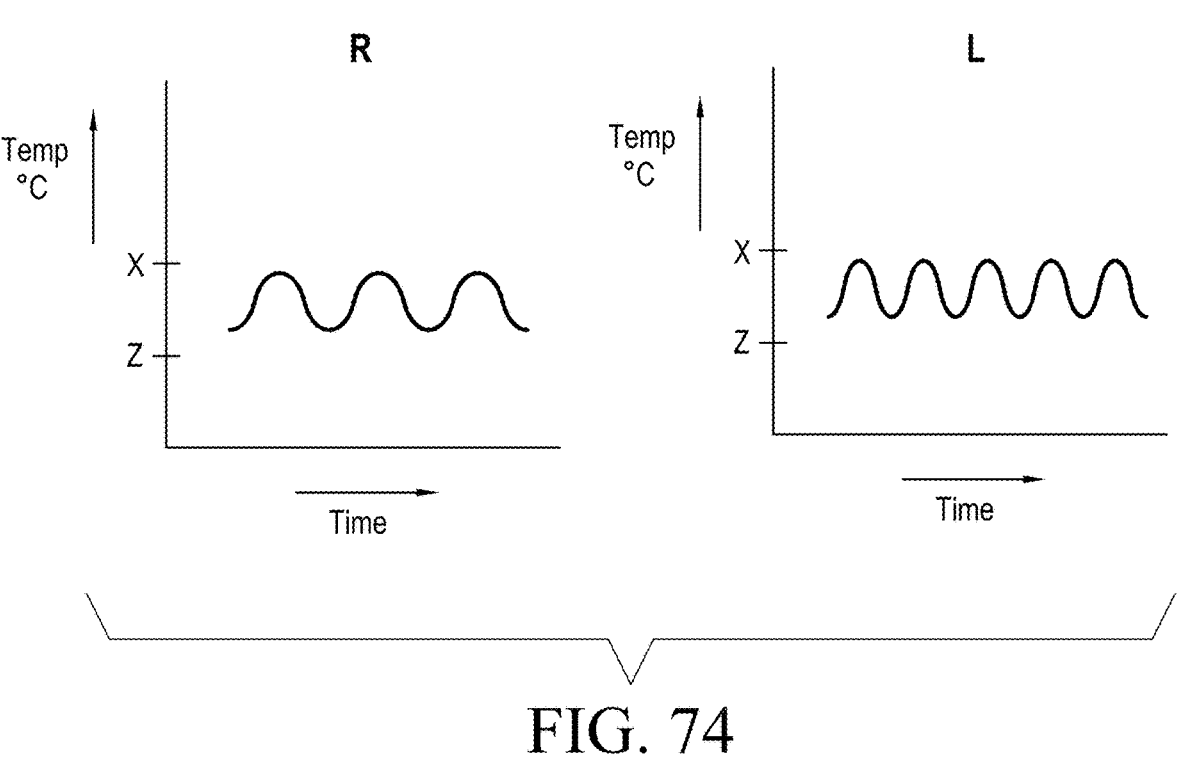
FIG. 74 shows a graph of ABTT temperatures showing a risk of seizures.

FIG. 74 shows an oscillatory pattern with higher frequency on left ABTT terminus 10 and lower frequency on right ABTT terminus 10 indicating risk of seizures on the left side.

Figure 75:
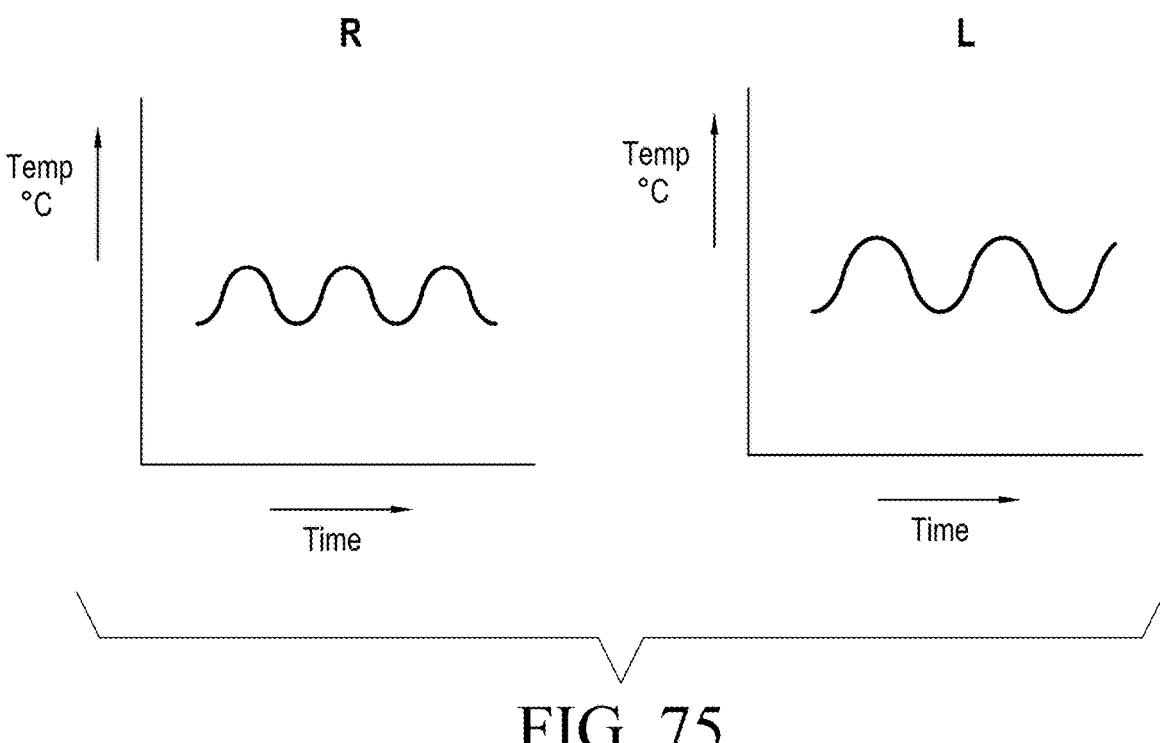
FIG. 75 shows a graph of ABTT temperatures showing a progression of infection.

FIG. 75 shows an oscillatory pattern with frequency lower than normal in both sides, but higher frequency in right ABTT terminus 10, indicating progression of infection on the left side of the brain or nervous system.

Figure 76:
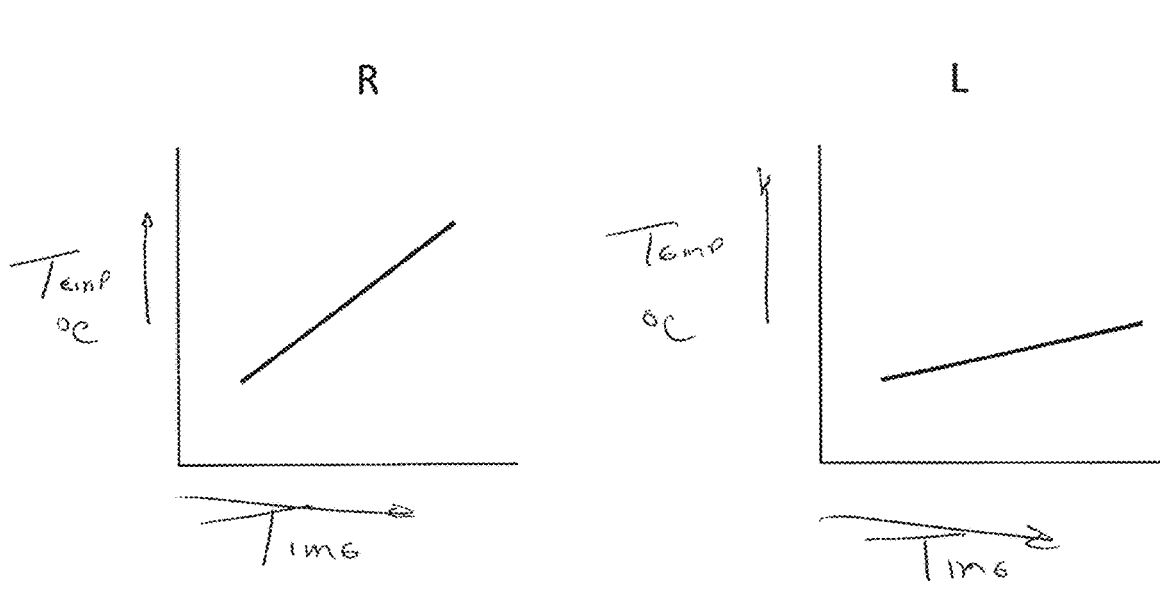
FIG. 76 shows a graph of ABTT temperatures indicating Alzheimer's disease or spread of Alzheimer's disease beyond the hippocampus.

FIG. 76 shows a higher velocity of temperature change in right ABTT terminus 10 as compared to the lower ABTT indicating risk of abscess in the right side.

Figure 77:
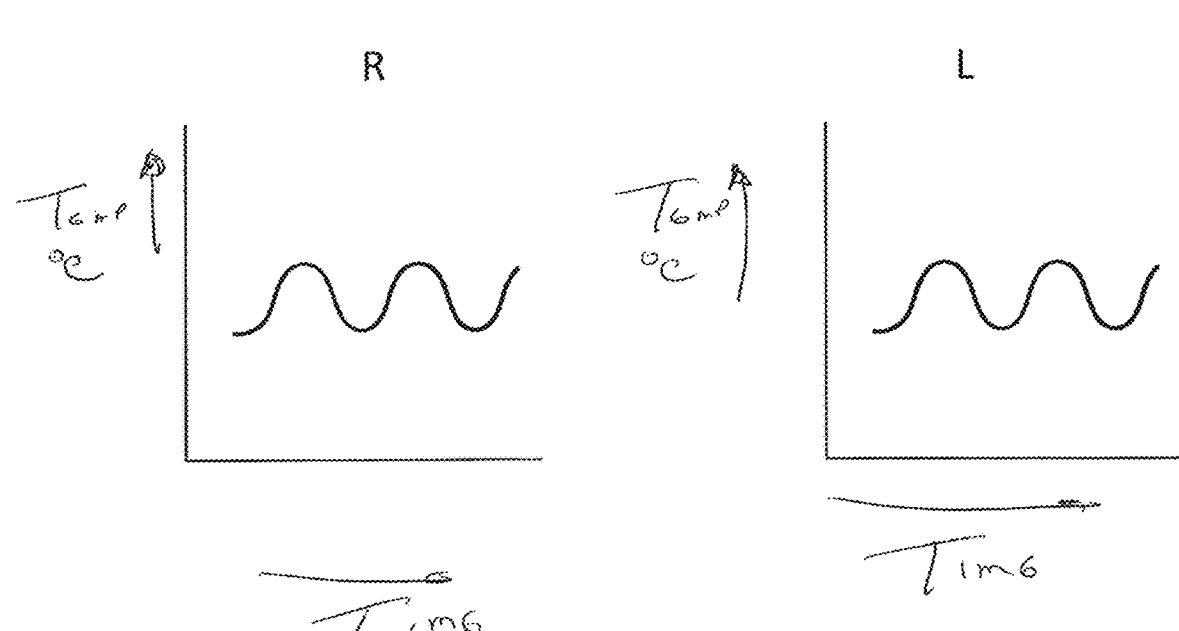
FIG. 77 shows a graph of ABTT temperatures indicating a risk of abscess.

FIG. 77 shows an oscillatory pattern with lower frequency on both, right ABTT terminus 10 and left ABTT terminus 10, indicating Alzheimer's disease or spread of Alzheimer's disease beyond the hippocampus.

Figure 78:
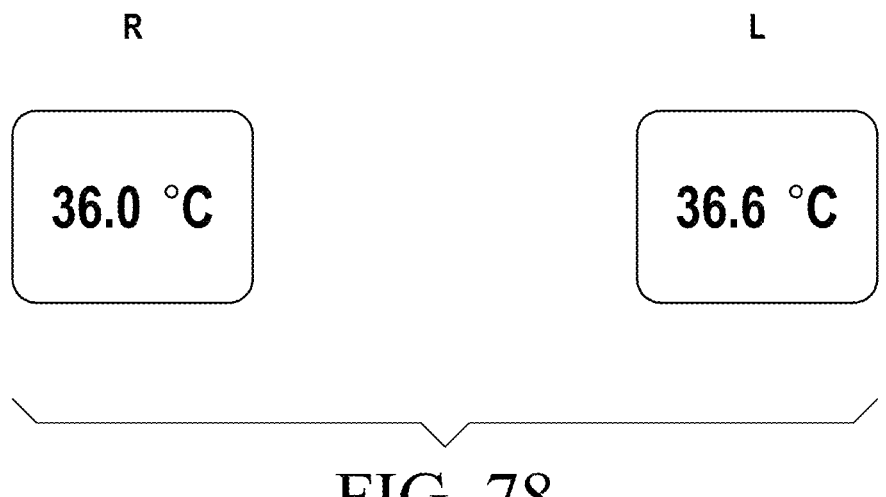
FIG. 78 shows a numerical display of ABTT temperatures indicating a risk of stroke.

FIG. 78 shows a display indicating numerical absolute value with lower temperature in right ABTT terminus 10 (36.0 degrees Celsius) and normal temperature in left ABTT terminus 10 (36.7 degrees Celsius) indicating risk of stroke in the right side.

System 400 is further configured to include a control device 408 that can be configured to include a keypad, microphone, USB or other port, card scanner, or other device to provide various control functions for system 400. Such control functions can include movement of IR camera 404 along support system 402 to align IR camera 404 with face 406. IR camera 404 can be configured to include a connector (not shown), a transceiver (not shown), or both. Similarly, control device 408 can be configured to include a connector (not shown), a transceiver (not shown), or both. Thus, control device 408 can communicate with IR camera 404 by way of a cable (not shown) or wirelessly. System 400 can further be configured to include pressure or presence detection device 316 that includes a pressure or presence sensor and is configured to communicate with control device 408 either through a cable (not shown) or wirelessly.

It should be understood that IR camera 404 includes a FOV 410 of a certain angle. In an exemplary embodiment, the configuration and position of IR camera 404 is such that FOV 410 is sufficiently large to include most or all of face 406 when a subject 412 is standing at a location of pressure or presence detection device 316. It should be understood that within FOV 410 is a smaller two-dimensional area 414 that corresponds to the area of ABTT terminus 10 and an area directly adjacent or next to ABTT terminus 10.

To operate system 400, subject 412 stands on pressure or presence detection device 316, which initiates or actuates system 400. Pressure or presence detection device 316 can immediately provide the weight of subject 412. In an exemplary embodiment, subject 412 can begin a temperature measurement operation by pressing a key on control device 408. Alternatively, the presence of subject 412 on pressure detection device 316 can initiate a temperature measurement operation. As yet another alternative, a separate electronic device (not shown), such as a cell phone, laptop, tablet, etc., can be configured to communicate with system 400 and to initiate system 400 operation as well as control the functions of system 400.

In an exemplary embodiment, subject 412 either manually moves IR camera 404 to aim toward an eye of subject 412, or uses controls on control device 408 to position IR camera 404 vertically along support system 402. In another exemplary embodiment, IR camera 404 moves along support system 402, scanning for the hot spot represented by ABTT terminus 10. In this latter embodiment, once IR camera 404 identifies the hot spot represented by ABTT terminus 10, IR camera 404 positions itself to acquire temperature signals from ABTT terminus 10. It should be noted that the movement of IR camera 404 also provides system 400 with the ability to measure the height of subject 412, since IR camera 404 can determine the location of the top of a head of subject 412 through its thermal imaging capability. Alternatively, once IR camera 404 has located ABTT terminus 10, system 400 can estimate the height of subject 412 given that the average distance from ABTT terminus 10 to the top of a typical person's head is a previously measured distance.

Once IR camera 404 is positioned to measure the temperature of ABTT terminus 10, acquisition and analysis of temperature data begins, which may be accomplished in control device 408 or in separate electronic device (not shown). The data acquisition process can be configured to include a plurality of time intervals, depending on the type of data analysis required. For simple temperature measurements, the length of data acquisition is typically seconds, e.g., 10 to 20 seconds. For complex measurements, the length of data acquisition can be minutes. Some data acquisition intervals may be very lengthy and it can be beneficial to provide a chair for subject 412.

Figure 71:
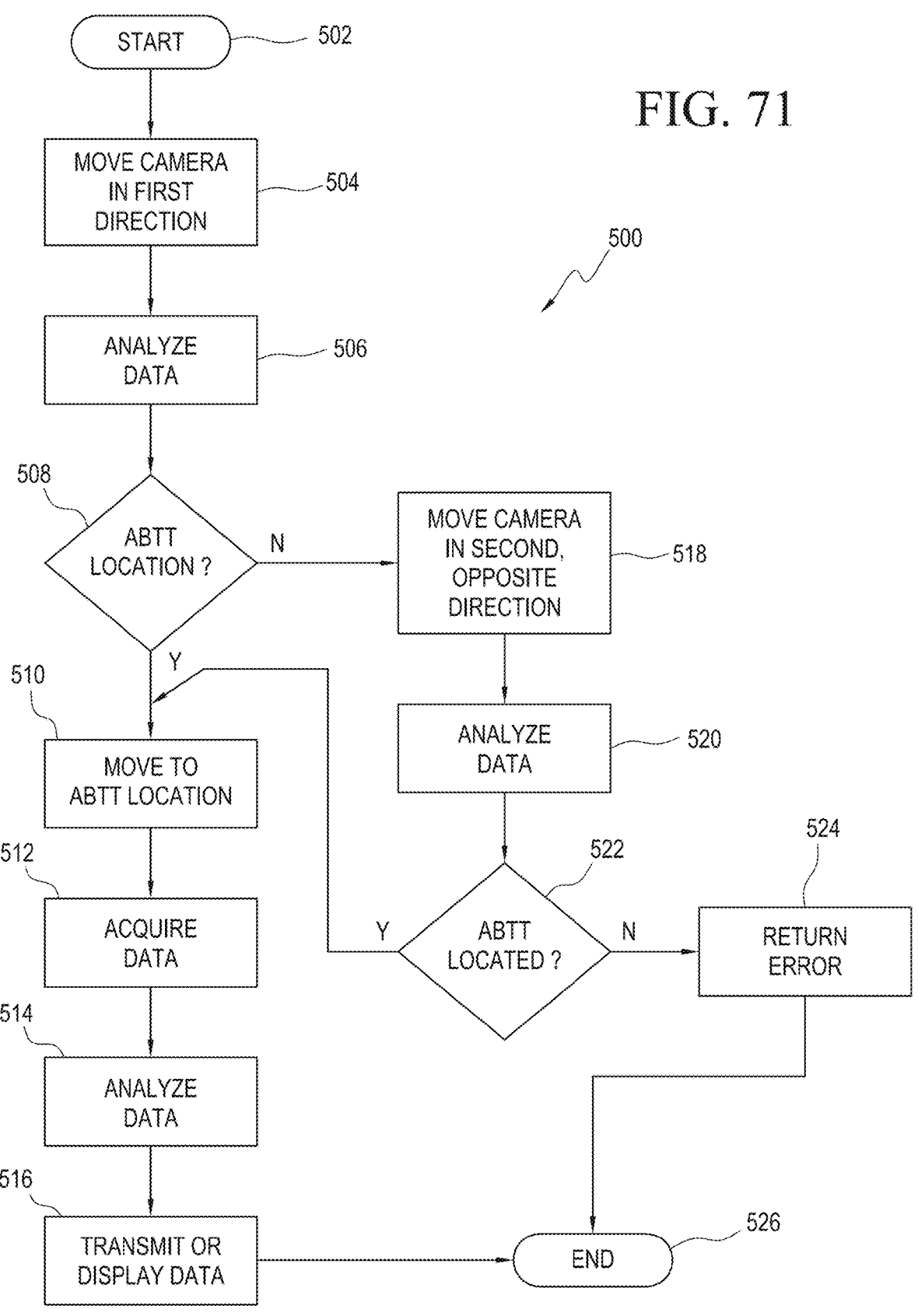
FIG. 71 shows an ABTT acquisition process in accordance with an exemplary embodiment of the present disclosure.

FIG. 71 shows an ABTT acquisition process in accordance with an exemplary embodiment of the present disclosure, indicated generally at 500. The function of process 500 is to drive an IR camera, such as IR camera 306, to a location where the temperature output of ABTT terminus 10 can be measured. Process 500 begins with a start process 502, during which various elements of an ABTT temperature measurement system are powered and initialized. Once the ABTT temperature measurement system is initialized, control passes from start process 502 to a first direction movement process 504.

In first direction movement process 504, the IR camera is moved vertically along a support system. While the IR camera is moving, it is acquiring IR imagery. In an exemplary embodiment, the data from the IR camera is being analyzed, for example at an analyze data process 506, as the data is acquired. In another exemplary embodiment, the data is analyzed after the IR camera reaches a first limit of travel. If the data is analyzed in near real time, as the data is acquired, control moves to an ABTT terminus located decision process 508 once a location of ABTT terminus 10 has been identified. Otherwise, the IR camera is permitted to reach the first limit before control is passed to ABTT terminus located decision process 508.

At ABTT terminus located decision process 508, a decision as to whether ABTT terminus 10 has been located is made. Such a decision may be made if a predetermined temperature of a face is identified, such as a temperature in a range of 97.5 to 106 degrees fahrenheit. In certain circumstances, skin surrounding ABTT terminus 10 may be hotter than ABTT terminus 10. The ABTT temperature measurement systems of the present disclosure are able to handle this situation by recognizing that all temperatures surrounding ABTT terminus 10 are hotter than ABTT terminus 10, thus recognizing that ABTT terminus 10 is cooler than skin surrounding ABTT terminus 10. In a very rare circumstance, the temperature of surrounding skin is approximately the same temperature of ABTT terminus 10, which may require additional measures to cool the surrounding skin to gain valid temperature measurements. If ABTT terminus 10 can be identified, control passes to a move to an ABTT terminus location process 510. If ABTT terminus 10 cannot be identified, control passes to a second direction movement process 518.

In move to ABTT terminus location process 510, the IR camera is driven to the height or location at which ABTT terminus 10 was identified. Once the IR camera reaches the determined location, control passes from ABTT terminus location process 510 to an acquire data process 512.

In acquire data process 512, temperature data from ABTT terminus 10 is acquired for a predetermined period. Such data acquisition can be for seconds to many minutes. A typical range of data acquisition for temperature readings only is approximately 10 to 20 seconds. For more detailed data acquisition to diagnose medical conditions, data acquisition can be from 30 seconds to 20 minutes or even more. Once the predetermined period for data acquisition has been reached, control passes from acquire data process 512 to an analyze data process 514.

The data received in acquire data process 512 is analyzed in analyze data process 514. Once analysis is complete, control moves from analyze data process 514 to a transmit or display data process 516, where the analyzed data is transmitted to an electronic device, such as a laptop, tablet, cell phone, etc., or the data is displayed on a system display, or both. Control then passes to an end process 526, which can place all hardware into a standby mode or an off mode after a predetermined period to permit review of the analyzed data.

Returning to second direction movement process 518, the IR camera is moved vertically along the support system in a second direction that is opposite to the first direction. While the IR camera is moving, it is acquiring IR imagery.

In an exemplary embodiment, the data from the IR camera is being analyzed, for example at an analyze data process 520, as the data is acquired. In another exemplary embodiment, the data is analyzed after the IR camera reaches a second limit of travel. If the data is analyzed in near real time, as the data is acquired, control moves to an ABTT terminus located decision process 522 once a location of ABTT terminus 10 has been identified. Otherwise, the IR camera is permitted to reach the first limit before control is passed to ABTT terminus located decision process 522.

At ABTT terminus located decision process 522, a decision as to whether ABTT terminus 10 has been located is made. Such a decision may be made if a predetermined temperature of a face is identified, such as a temperature in a range of 97.5 to 106 degrees fahrenheit. In certain circumstances, skin surrounding ABTT terminus 10 may be hotter than ABTT terminus 10. The ABTT temperature measurement systems of the present disclosure are able to handle this situation by recognizing that all temperatures surrounding ABTT terminus 10 are hotter than ABTT terminus 10, thus recognizing that ABTT terminus 10 is cooler than skin surrounding ABTT terminus 10. In a very rare circumstance, the temperature of surrounding skin is approximately the same temperature of ABTT terminus 10, which may require additional measures to cool the surrounding skin to gain valid temperature measurements. If ABTT terminus 10 can be identified, control passes to a move to ABTT terminus location process 510, which operates as previously described herein. If ABTT terminus 10 cannot be identified, control passes to a return error process 524.

In return error process 524, a notification is provided to the subject, patient, or other individual that ABTT terminus 10 was not located. Control then passes from return error process 524 to end process 526, which functions as previously described.

While some embodiments herein describe thermal imaging such that an entirety of a face is acquired, it should be apparent that full face imaging is not required to locate and identify a horn-shaped region between the eye and the nose where ABTT terminus 10 is located. Thus, in some embodiments the thermal imaging camera may only need a field of view sufficient to identify the unique location on the face where ABTT terminus 10 is located rather than an entire face.

While various embodiments of the disclosure have been shown and described, it is understood that these embodiments are not limited thereto. The embodiments can be changed, modified, and further applied by those skilled in the art. Therefore, these embodiments are not limited to the detail shown and described previously, but also include all such changes and modifications. Any part of any embodiment can be used in combination to create a single embodiment, and any part of any embodiment can be used as a replacement or addition to another embodiment, and all resultant embodiments are within the scope of the present disclosure.

I claim:

1. A system for locating and measuring a temperature of an Abreu brain thermal tunnel (ABTT), the system comprising:

a support; and a device adjustably attached to the support so that the device is adjustable in a vertical direction to allow for a plurality of positions having different heights, the device comprising:

a temperature sensor sized and dimensioned to detect and measure the temperature of an ABTT terminus of a user, the temperature sensor configured to provide a temperature measurement; and a display configured to receive and display the temperature measurement, wherein the display is arranged directly on top of the temperature sensor such that the user can view the display while the temperature of the ABTT terminus is detected and measured.

2. The system of claim 1, further comprising a mirror including a mirrored surface to allow the user to see a reflection of the user during the measurement.

3. The system of claim 1, wherein the temperature sensor is an infrared camera.

4. The system of claim 3, further including a control device that is configured to communicate with the infrared camera.

5. The system of claim 4, further comprising a pressure detection device that includes a pressure sensor and is configured to communicate with the control device.

6. The system of claim 5, wherein the pressure detection device is configured to inform the control device of the presence of the user to initiate a temperature measurement operation.

7. The system of claim 5, wherein the pressure detection device is configured to allow for the user to stand on it to activate the pressure sensor.

8. The system of claim 7, wherein the pressure detection device is configured to measure a weight of the user.

9. A device for locating an Abreu brain thermal tunnel (ABTT) and measuring a temperature of the ABTT, the device comprising:

a support base;

a sliding mechanism arranged vertically on the support base, the sliding mechanism configured to move in a vertical direction along the support base;

an infrared sensor attached to the sliding mechanism that is configured to acquire a thermal image of a human face and to transmit the thermal image;

a processor configured to receive the transmitted thermal image, to analyze the thermal image to determine a location of an ABTT terminus, and to transmit a result of the analysis of the thermal image; and a display configured to receive the results of the analysis of the thermal image and to display the results of the analysis, wherein the display is arranged directly on top of the infrared sensor such that a user can view the display while the thermal image of the human face is acquired.

10. The device of claim 9, wherein the infrared sensor is configured to automatically move with the sliding mechanism.

11. The device of claim 9, further including a pressure sensor, wherein activation of the pressure sensor causes the device to be actuated.

12. The device of claim 11, wherein the pressure sensor is configured to allow for a user to stand on it to activate the pressure sensor.

13. The device of claim 9, further comprising a card reader and a keypad configured for connecting with a separate electronic device being operatively coupled with the device.

14. The device of claim 13, wherein the separate electronic device is a cell phone.

15. The device of claim 13, wherein the separate electronic device provides height information of a user.

16. The device of claim 13, wherein the card reader is configured to accept a card to allow a function.

17. The device of claim 16, wherein the function is at least one selected from purchasing a measurement or identification of the user.

18. The device of claim 9, wherein the infrared sensor comprises an array of thermopiles.

19. The device of claim 18, wherein the array of thermopiles is separated into a left array for sensing a temperature of a left ABTT of a user and a right array for sensing a temperature of a right ABTT of a user.

* * * * *